US008801918B2

(12) United States Patent
Qin et al.

(10) Patent No.: US 8,801,918 B2
(45) Date of Patent: Aug. 12, 2014

(54) POINT OF CARE HEPARIN DETERMINATION SYSTEM

(75) Inventors: Wei Qin, Plymouth, MN (US); Daniel S. Cheek, Plymouth, MN (US); Christopher Hobot, Brooklyn Park, MN (US); Kelvin Bonnema, Brooklyn Park, MN (US); Randy Meyer, Brooklyn Center, MN (US); Douglas Dean Nippoldt, Centerville, MN (US); Vitally G. Sitko, Medina, MN (US); Qingshan (Sam) Ye, Brooklyn Park, MN (US); Narayanan Ramamurthy, Alpharetta, GA (US)

(73) Assignee: Medtronic, Inc., Minneapolis, MN (US)

( * ) Notice: Subject to any disclaimer, the term of this patent is extended or adjusted under 35 U.S.C. 154(b) by 1138 days.

(21) Appl. No.: 12/748,918

(22) Filed: Mar. 29, 2010

(65) Prior Publication Data
US 2010/0181210 A1    Jul. 22, 2010

Related U.S. Application Data

(62) Division of application No. 11/126,887, filed on May 11, 2005, now Pat. No. 7,699,966.

(60) Provisional application No. 60/572,071, filed on May 17, 2004.

(51) Int. Cl.
| G01N 27/333 | (2006.01) |
| G01N 33/86 | (2006.01) |
| A61M 1/36 | (2006.01) |

(52) U.S. Cl.
CPC .......... *G01N 27/3335* (2013.01); *G01N 27/333* (2013.01); *G01N 33/86* (2013.01); *A61M 1/3675* (2013.01)
USPC ....... 205/792; 204/403.01; 204/411; 204/416

(58) Field of Classification Search
USPC ............ 204/400, 403.01, 405, 409, 411, 416, 204/418; 205/792; 435/13
See application file for complete search history.

(56) References Cited

U.S. PATENT DOCUMENTS

| 2,129,043 A | 9/1938 | Bortsch |
| 2,411,316 A | 11/1946 | Capita |

(Continued)

FOREIGN PATENT DOCUMENTS

| DE | 3 438 221 | 4/1986 |
| DE | 339 613 | 11/1989 |

(Continued)

OTHER PUBLICATIONS

Bakker et al. "Extraction Thermodynamics of Polyanions into Plasticized Polymer Membranes Doped with Lipophilic Ion Exchanges: A Potentionmeteric Study," Macromolecules, 28:5834-5840 (1995).

(Continued)

*Primary Examiner* — J. Christopher Ball

(57) ABSTRACT

Methods and devices for point of care determination of heparin concentration in blood are described. Cartridges including protamine ion sensitive electrodes (ISEs) and reference electrodes and systems for automatically determining heparin concentration in the cartridges are provided. Some systems add blood to a protamine bolus sufficient to bind all heparin, leaving excess protamine. The excess protamine concentration can be determined by measuring the initial slope of the electrode potential rate of change, and comparing the slope to known protamine concentration slope values In some cartridges, an oscillating pressure source moves the blood-protamine mixture back and forth across the protamine ISE. Some systems also use a second blood sample having the heparin removed or degraded to create a blank reference sample. Protamine ISEs can include polyurethane polymer, DNNS ionophore, and NPOE plasticizer. The polyurethane may include hard segments and soft segments, where both hard and soft segments may include cyclic and straight chain aliphatic moieties having essentially no ester or ether groups. Some hard segments may include methylene diphenyl groups. Some reference electrodes have the same polymer, plasticizer, and ionophore as the measurement electrode, but with a different concentration of ionophore.

12 Claims, 36 Drawing Sheets

PROTAMINE INFUSION TIME
(α HEPARIN CONCENTRATION)

(56) References Cited

U.S. PATENT DOCUMENTS

| | | |
|---|---|---|
| 2,850,026 A | 9/1958 | Leatherman |
| 3,038,327 A | 9/1962 | Resnick |
| 3,077,106 A | 2/1963 | Fink |
| 3,129,911 A | 4/1964 | Fitzpatrick |
| 3,302,452 A | 2/1967 | Leslie |
| 3,307,392 A | 3/1967 | Owen et al. |
| 3,450,501 A | 6/1969 | Oberhardt |
| 3,492,096 A | 1/1970 | Hattersley |
| 3,525,254 A | 8/1970 | Milanes |
| 3,560,162 A | 2/1971 | Mittleman |
| 3,560,163 A | 2/1971 | Mittleman |
| 3,587,295 A | 6/1971 | Simons |
| 3,635,678 A | 1/1972 | Seltz et al. |
| 3,650,698 A | 3/1972 | Adler |
| 3,658,480 A | 4/1972 | Kane et al. |
| 3,692,487 A | 9/1972 | Sanz |
| 3,695,842 A | 10/1972 | Mintz |
| 3,699,437 A | 10/1972 | Ur |
| 3,704,099 A | 11/1972 | Sanz |
| 3,713,780 A | 1/1973 | Shapiro |
| 3,719,075 A | 3/1973 | Mandrona et al. |
| 3,741,002 A | 6/1973 | Simons |
| 3,775,339 A | 11/1973 | Kasulin et al. |
| 3,814,585 A | 6/1974 | Bailly |
| 3,836,333 A | 9/1974 | Mintz |
| 3,854,324 A | 12/1974 | Altshuler et al. |
| 3,911,728 A | 10/1975 | Fixot |
| 3,918,908 A | 11/1975 | Moyer et al. |
| 3,923,627 A | 12/1975 | Niedrach et al. |
| 3,932,233 A | 1/1976 | Ruzicka et al. |
| 3,963,349 A | 6/1976 | Albright et al. |
| 3,985,618 A | 10/1976 | Innerfield |
| 3,999,333 A | 12/1976 | Amarantos |
| 4,000,972 A | 1/1977 | Braun et al. |
| 4,026,671 A | 5/1977 | Simons et al. |
| 4,036,231 A | 7/1977 | Dodge et al. |
| 4,040,788 A | 8/1977 | Simons et al. |
| 4,058,367 A | 11/1977 | Gilford |
| 4,067,777 A | 1/1978 | Innerfield et al. |
| 4,074,971 A | 2/1978 | Braun et al. |
| 4,081,242 A | 3/1978 | Girolami |
| 4,115,209 A | 9/1978 | Freiser et al. |
| 4,116,635 A | 9/1978 | Jaeger |
| 4,129,131 A | 12/1978 | Naftulin |
| 4,131,549 A | 12/1978 | Ferrara |
| 4,160,801 A | 7/1979 | Badolato et al. |
| 4,197,735 A | 4/1980 | Munzer et al. |
| 4,210,623 A | 7/1980 | Breno et al. |
| 4,243,671 A | 1/1981 | Harris et al. |
| 4,257,199 A | 3/1981 | Kuboyama |
| 4,285,906 A | 8/1981 | Meltzer et al. |
| 4,332,264 A | 6/1982 | Gortz et al. |
| 4,359,463 A | 11/1982 | Rock |
| 4,362,698 A | 12/1982 | Boosalis et al. |
| 4,390,499 A | 6/1983 | Curtis et al. |
| 4,391,780 A | 7/1983 | Boris |
| 4,443,408 A | 4/1984 | Mintz |
| 4,533,519 A | 8/1985 | Baugh et al. |
| 4,534,939 A | 8/1985 | Smith et al. |
| 4,540,801 A | 9/1985 | Nysted et al. |
| 4,551,308 A | 11/1985 | Mintz |
| 4,599,219 A | 7/1986 | Cooper et al. |
| 4,612,801 A | 9/1986 | Girolami |
| 4,663,127 A | 5/1987 | Jackson et al. |
| 4,671,939 A | 6/1987 | Mintz |
| 4,692,406 A | 9/1987 | Becker et al. |
| 4,720,787 A | 1/1988 | Lipscomb |
| 4,752,449 A | 6/1988 | Jackson et al. |
| 4,770,759 A | 9/1988 | Young et al. |
| 4,780,418 A | 10/1988 | Kratzer |
| 4,782,026 A | 11/1988 | Baugh et al. |
| 4,788,139 A | 11/1988 | Ryan |
| 4,795,703 A | 1/1989 | Folkman et al. |
| 4,797,369 A | 1/1989 | Mintz |
| 4,851,336 A | 7/1989 | Yin |
| 4,871,677 A | 10/1989 | Baugh et al. |
| 4,876,069 A | 10/1989 | Jockimsen |
| 4,960,694 A | 10/1990 | Eckardt et al. |
| 4,986,964 A | 1/1991 | Carr, Jr. et al. |
| 5,064,556 A | 11/1991 | Brandes et al. |
| 5,091,304 A | 2/1992 | LaDuca et al. |
| 5,093,325 A | 3/1992 | Witt et al. |
| 5,165,952 A | 11/1992 | Solomon et al. |
| 5,174,961 A | 12/1992 | Smith |
| 5,183,549 A | 2/1993 | Joseph et al. |
| 5,196,404 A | 3/1993 | Maraganore et al. |
| 5,207,988 A | 5/1993 | Lucas |
| 5,236,670 A | 8/1993 | Iwata |
| 5,246,715 A | 9/1993 | Orevi et al. |
| 5,248,673 A | 9/1993 | Balasubramanian et al. |
| 5,262,325 A | 11/1993 | Zimmermann et al. |
| 5,266,462 A | 11/1993 | Hemker et al. |
| 5,314,601 A | 5/1994 | Hardee et al. |
| 5,314,826 A | 5/1994 | Baugh |
| 5,387,581 A | 2/1995 | Odawara et al. |
| 5,401,377 A | 3/1995 | Shieh et al. |
| 5,417,835 A | 5/1995 | Brown et al. |
| 5,441,892 A | 8/1995 | Baugh |
| 5,453,171 A | 9/1995 | Ma et al. |
| 5,472,852 A | 12/1995 | Smirnov et al. |
| 5,505,721 A | 4/1996 | Leach et al. |
| 5,510,330 A | 4/1996 | Martin et al. |
| 5,525,477 A | 6/1996 | Hassouna |
| 5,525,478 A | 6/1996 | Matschiner |
| 5,563,041 A | 10/1996 | Reers |
| 5,602,037 A | 2/1997 | Ostgaard et al. |
| 5,607,567 A | 3/1997 | Yun et al. |
| 5,607,952 A | 3/1997 | Badore et al. |
| 5,612,369 A | 3/1997 | Bone et al. |
| 5,612,378 A | 3/1997 | Tianbao et al. |
| 5,637,599 A | 6/1997 | Levy et al. |
| 5,674,236 A | 10/1997 | Baugh |
| 5,702,912 A | 12/1997 | Hemker et al. |
| 5,897,758 A | 4/1999 | Musacchio et al. |
| 5,911,862 A | 6/1999 | Chan |
| 5,925,319 A | 7/1999 | Baugh et al. |
| 5,951,951 A | 9/1999 | Lane et al. |
| 5,972,712 A | 10/1999 | Baugh et al. |
| 6,004,442 A | 12/1999 | Choulga et al. |
| 6,010,911 A | 1/2000 | Baugh et al. |
| 2002/0081741 A1 | 6/2002 | Braun et al. |
| 2003/0057108 A1 | 3/2003 | Sridharan |
| 2005/0023153 A1 | 2/2005 | Bakker et al. |

FOREIGN PATENT DOCUMENTS

| | | |
|---|---|---|
| DE | 4 427 921 | 2/1996 |
| EP | 333862 | 9/1989 |
| EP | 0 661 383 | 7/1995 |
| EP | 767 372 | 4/1997 |
| EP | 1 376 123 | 1/2004 |
| JP | 59057 156 | 4/1984 |
| WO | 93/25578 | 12/1993 |
| WO | 01/88520 | 11/2001 |

OTHER PUBLICATIONS

Bakker et al. "Reversible Electrochemical Detection of Nonelectroactive Polyions," J. Am. Chem. Soc., 125:11192-11193 (2003).

Baugh Eta L., "Heparinase in the Activated Clotting Time Assay: Monitoring Heparin-Independent Alterations in Coagulation Function," Anesth. Analg., 74:201-205 (1992).

"Blood Component Therapy, a Physician's Handbook," American Association of Blood Banks (1975).

Brown, ed., "Hematology: Principles and Procedures", pp. 127-127 (1980).

Ceresa et al., "Direct Potentiometric Information of Total Ionic Concentrations," Anal. Chem., 72:2050-2054 (2000).

Dai et al., "Bioanalytical Applications of Polyion-Sensitive Electrodes," Journal of Bioanalytical and Biomedical Analysis, 19:1-14 (1999).

(56) References Cited

OTHER PUBLICATIONS

Demopoulous et al., "Platelet activating factor. Evidence for 1-0-alkyl-2-acetyl-sn-glyceryl-3 phosphorycholine as the active component (A new class of lipid chemical mediators)," Journal of Biological Chemistry, 254:9355-9358 (1979).
Despotis et al., "Monitoring of Hemostasis in Cardiac Surgical Patients: Impact of Point-of-Care Testing on Blood Loss and Trasnfusion Outcomes," Clinical Chemistry, 43(9):1684-1696 (1997).
Fu et al., "Response Mechanism of Polymer Membrane-Based Potentiometric Polyion Sensors," Analytical Chemistry, 66(14):2250-2259 (Jun. 1996).
Grode et al., "Biocompatible materials for use in the vascular system," J. Biomed. Mater. Res. Symposium, 3:201-205 (1972).
Han et al, "Selective Monitoring of Pedtidase Activities with Synthetic Polypeptide Substrates and Polyion-Sensitive Membrane Electrode Detection," The FASEB Journal, 10:1621-1626 (Dec. 1996).
Hartman et al., Mikcrochimica Acta [Wein], 1978, II 235-246.
Heng et al., "Influence of Methacrylic-Acrylic Copolymer Composition on Plasticieser-free Optode Films for pH Sensors", 3:83-90 (2003).
Hirsh MD et al., eds., Hemostatis & Thrombosis, a Conceptual Approach, Second Ed., pp. 1-45 (1983).
Holloway et al., Chem. Abstr., 100(3):18422g, 1984.
J. Coll. Int. Sci., "Plasmon Resonance (SPR) for Heparin Assay. Part I. Protamine as a Heparin Affinity Surface," 193:365-372 (1997).
Lutz et al., "Stabilized Potentiometric Solid-State Polyion Sensors Using Silver-Calixarene Complexes as Additivies within Ion-Exchanger-Based Polymer Films," Fresenius' Journal of Analytical Chemistry, 364(1-2):41-47 (May 1999).
Ma et al., "Electrochemical Sensor for Heparin: Further Characterization and Bioanalytical Applications," Analytical Chemistry, 85(16):2078-2084 (Aug. 1, 1993).
Meyerhoff et al., "Heparin-Responsive Electrochemical Sensor: A Preliminary Study," Anal. Chem., 64:694-697 (1992).
Meyerhoff et al., "Potentiometric Polyion Sensors: New Measurement Technology for Monitoring Blood Heparin Concentrations During Open Heart Surgery" Clinical Chemistry, 41:1355-1356 (1995).
Moorhead et al., "Platelet Involvement in the Activated Coagulation Time of Heparinized Blood," 63(4):394-398 (Apr. 1984).
Osterud et al., "The clotting time of whole blood in plastic tubes: The influence of exercise, prostacyclin and acetylsalicylic acid," 29(4):425-435 (Feb. 15, 1983).
Qin et al., "Enhanced sensitivity electrochemical assay of low-molecular-weight heparins using rotating polyion-sensitive membrane electrodes", Anal. Bioanal. Chem., 377:929-936 (2003).
Ramamurthy et al., "Improved Protamine-Sensitive Membrane Electrode for Monitoring Heparin Concentrations in Whole Blood via Protamine Titration," Clinical Chemistry, 44(3):606-613 (1998).
Ramamurthy et al., "Determination of Low-Molecular-Weight Heparins and Their Binding to Protamine and a Protamine Analog Using Polyion-Sensitive Membrane Electrodes," Analytical Biochemistry, 226:116-124 (1999).
Ramamurthy et al., "Development and Biomedical Applications of an Improved Polycation-Sensitivie Membrane Electrode," Doctoral dissertation, University of Michigan, Ann Arbor (1999).
Roberts et al., Chem. Abstr., 85(11):7452a, 1976.
Shvarev et al., "Pulsed Galvanostatic Control of Ionophore-Based Polymeric Ion Sensors", Anal. Chem., 75:4541-4550 (2003).
Spivak et al., eds., Fundamentals of Clinical Hemodology, pp. 390-391 (1984).
Vander et al., eds., "Human Physiology", p. 377 (1985).
Wahr et al., "A New Method of Measuring Heparin Levels in Whole Blood by Protamine Titration Using a Heparin-Responsive Electrochemical Sensor," Journal of Cardiothoracic and Vascular Anethesia, 10(4):447-450 (Jun. 1996).
Wegmann et al., Mikcrochimica Acta [Wein], 1984, III 1-16.
Windholz et al., eds., The Merck Index, 10th Ed. Merck & Co., Inc. (Rahway), 1983, pp. 672-673, 1133-1134 and 1233.
Yang et al., "A Novel Electrochemical Heparin Sensor," ASAIO Journal, 39(3):195-201 (Jul.-Sep. 1993).
Ye et al., "Rotating Electrode Potentiometry: Lowering the Detection Limits of Nonequilibrium Polyion-Sensitive Membrane Electrodes," Analytical Chemistry, 73(2):332-336 (Jan. 15, 2001).
Yun et al., "A Disposable, Coated Wire Heparin Sensor," ASAIO Journal, M401-M405 (1994).
Yun et al., "Clinical Application of Disposable Heparin Sensors, Blood Heparin Measurements During Open Heart Surgery", ASAIO Journal, 41(3):661-664 (Jul.-Sep. 1995).
Yun et al., "Potamine-Sensitive Polymer Membrane Electrode: Characterization and Bioanalytical Applications,"Analytical BioChemistry, 224(1):212-220 (Jan. 1, 1995).
U.S. Appl. No. 60/485,586, filed Jul. 9, 2003 to Bakker.

PROTAMINE INFUSION TIME
(α HEPARIN CONCENTRATION)

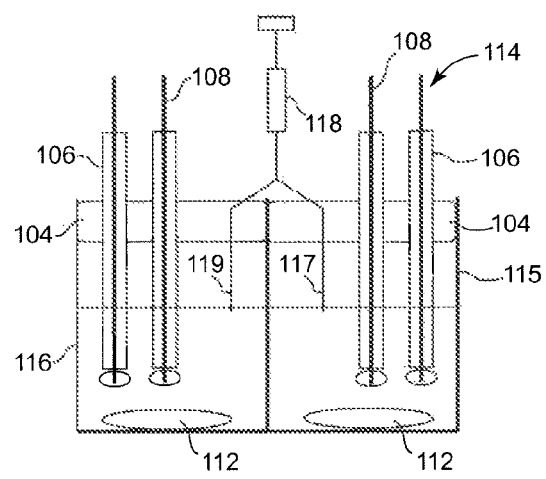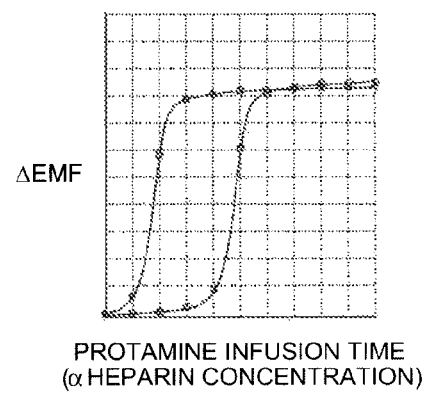
Fig. 3A
Fig. 3B
PROTAMINE INFUSION TIME
($\alpha$ HEPARIN CONCENTRATION)

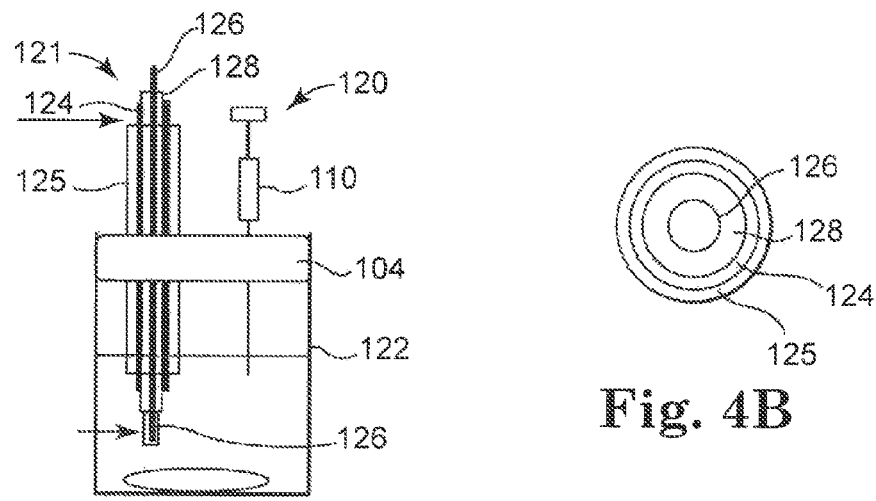
Fig. 4A
Fig. 4B
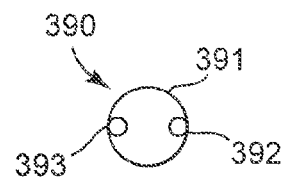
Fig. 4C
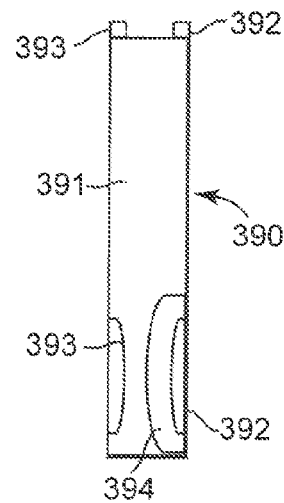
Fig. 4D

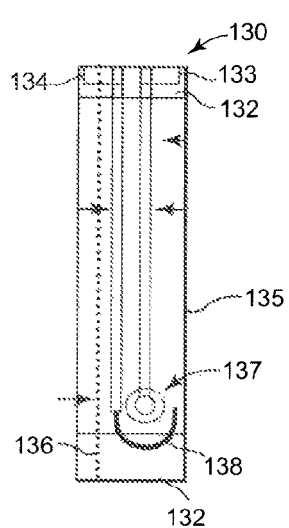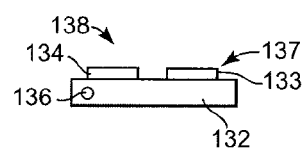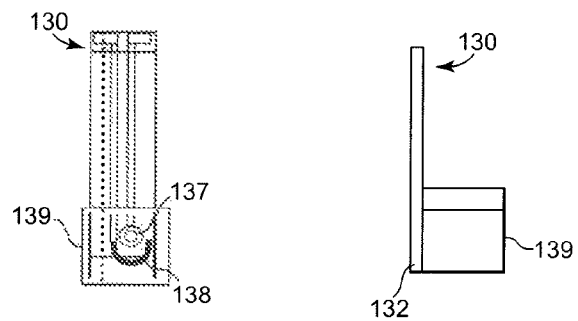
Fig. 5A  Fig. 5B  Fig. 5C  Fig. 5D

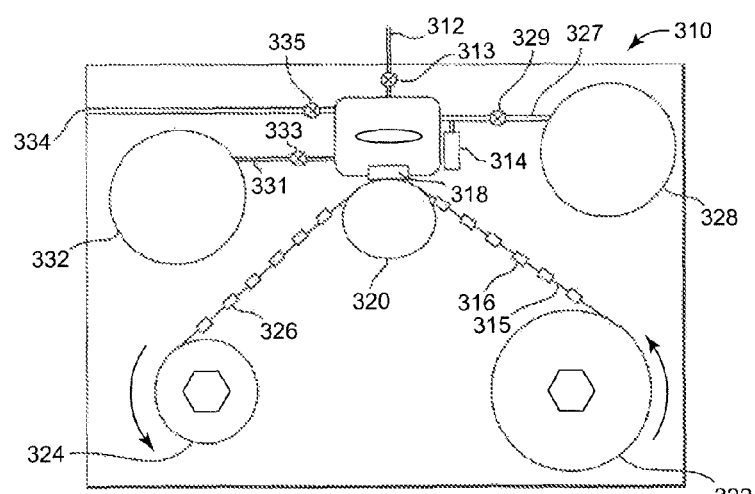
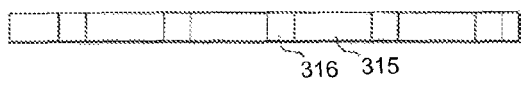
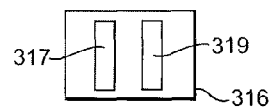
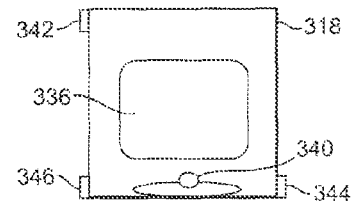
Fig. 13A
Fig. 13B
Fig. 13C
Fig. 13D

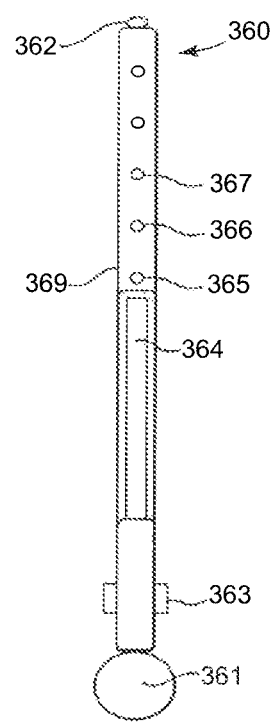
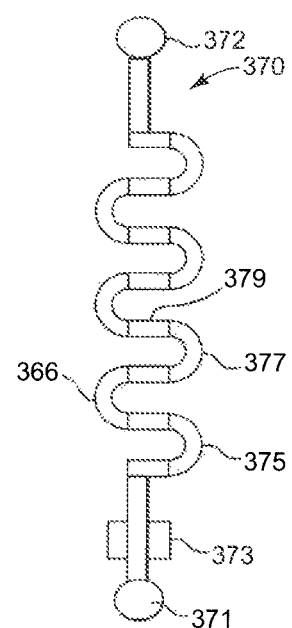
Fig. 14A
Fig. 14B

| | heparin | count | Subtract 0U | Ratio to 1U |
|---|---|---|---|---|
| 5 dps | 0 U | 262 | | |
| | 1 U | 280 | 18 | 1 |
| | 3 U | 370 | 108 | 6 |
| | 6 U | 474 | 212 | 11.8 |
| Adjustable dps | 0 U | 154 | | |
| | 1 U | 193 | 39 | 1 |
| | 3 U | 270 | 116 | 3 |
| | 6 U | 415 | 261 | 6.7 |

"SOFT" SEGMENT

2 DIMER DIISOCYANATE + 2 BUTANEDIOL + 1 DIMER DIOL 2 (1-DECYL-4-NONYL CYCLOHEXYL + 2 BUTANEDIOL + 1 ( 1-DECYL -4- NONYL
DIISOCYANATE) CYCLOHEXYL DIOL)

"HARD" SEGMENT

5 METHYLENE DIPHENYLISOCYANATE + 1 BUTANEDIOL + 3 DIMER DIOL

5 METHYLENE DIPHENYLISOCYANATE + 1 BUTANEDIOL + 3 (1-DECYL-4-NONYL
CYCLOHEXYL DIOL)

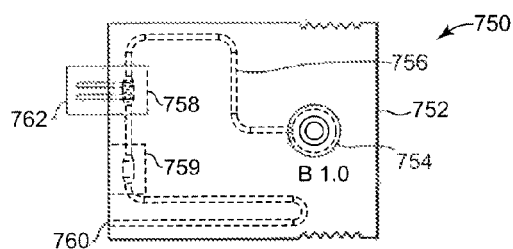
Fig. 29B
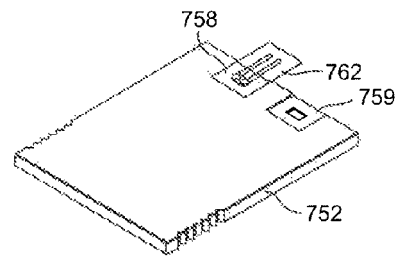 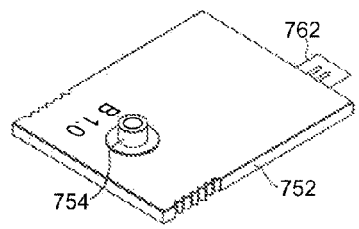
Fig. 29C                    Fig. 29D

POINT OF CARE HEPARIN DETERMINATION SYSTEM

CROSS-REFERENCE TO RELATED APPLICATIONS

This application is a divisional application of U.S. patent application Ser. No. 11/126,887, filed May 11, 2005, now U.S. Pat. No. 7,669,966 which in turn claims the benefit of U.S. Provisional Application No. 60/572,071, filed May 17, 2004, entitled, "Point of Care Heparin Determination System" (the entire contents of which are incorporated by reference herein).

FIELD OF THE INVENTION

The present invention is related generally to medical patient care systems. More specifically, the present invention is related to systems for measuring polyion levels in a solution. Even more specifically, the present invention is related to systems for measuring heparin (including low molecular weight and unfractionated) levels in blood or other fluids such as plasma or buffer.

BACKGROUND

Heparin is an anti-coagulant commonly used in some surgical procedures. Heparin is used in high doses in most open-chest heart procedures. The two most common types of open-chest heart procedures are the arrested heart surgical procedure, in which the patient is put on a heart-lung bypass machine, and the beating heart surgical procedure. The heparin significantly reduces clotting or coagulation of the patient's blood.

At the end of a procedure, the normal clotting of the blood is once again desirable. In order to effectively remove the heparin from the patient's blood, protamine is added. The protamine binds to the heparin, deactivating the heparin. The heparin-protamine complex is then cleared from the body by the liver.

It is necessary to determine the amount of heparin in the patient's blood at several points in time. As some patients may have heparin already in their system, an initial determination of the baseline heparin concentration may be required. After heparin is added, the heparin concentration is determined to insure that the heparin has been properly added. While the patient is heparinized, the heparin concentration is monitored to insure that the heparin concentration is maintained above a threshold level. In order to determine the proper amount of protamine to add to deactivate heparin, the concentration of heparin should be determined. After protamine is added, the heparin concentration may again be determined to insure that the heparin has been properly deactivated.

Several methods of determining or inferring heparin concentrations are currently used. In one method, the patient's blood is drawn and sent to a laboratory. In the laboratory, the heparin may be titrated with protamine until the heparin has been entirely bound to protamine. The concentration of heparin may then be determined as a function of the stoichiometry of the protamine titrant used. The stoichiometry of the protamine may be determined by titration against standard heparin samples. The method is far from ideal for use in providing timely feedback to the treating physician, due to the time lag in obtaining results.

A more commonly used method for heparin measurement in the central lab setting is a colorimetric anti-Factor Xa (FXa) assay. This assay is a standard feature on several analyzers and is performed on plasma samples. It uses the principle of heparin-mediated inhibition of FXa. The drawback of this assay is that it needs to be corrected for hematocrit (since it is performed on plasma) as well as the source of heparin (if it is a variable). This assay is more suited for testing high number of samples and is not conducive for testing a few samples. Another significant drawback is a high turnaround time, since this is a central lab test)

In another method, an Activated Clotting Time (ACT) test is used. In this test, the time required for the patient's blood to clot is measured and used to infer a likely heparin level. This method is indirect, and may produce misleading results, as the ACT values may be affected by hemodilution and hypothermia. This method does not directly measure heparin and has limited accuracy.

In still another method, the heparin concentration is localized to a range using multiple protamine samples by using a property of the heparin-protamine interaction. The time required for the heparin and protamine to bind is minimized when the amount of protamine approximates the stoichiometric amount needed to exactly bind the heparin. Insufficient or excess protamine results in longer clotting times. The HEPCON Hemostasis Management System (HMS) available from Medtronic, Inc. (Minneapolis, Minn.) makes use of this property.

The HMS assay system is based on a protamine titration and uses clot formation for end-point detection. The assay is performed in a cartridge containing four to six channels that contain different amounts of protamine as well as dilute thromboplastin (to accelerate clot formation). The end-point of the titration is the detection of clot formation, which is determined by measuring the rate of fall of a plunger mechanism in each cartridge. The channel containing the smallest quantity of protamine that completely neutralizes the heparin exhibits the shortest clotting time. The heparin concentration is measured from the quantity of protamine in that channel (on the basis of the heparin-protamine stoichiometry). Each Hepcon cartridge thus tests a limited range of blood concentrations.

The HMS system can utilize up to 12 different cartridges having differing, known protamine amounts within. The treating physician can estimate the expected range of heparin and select a limited number of cartridges in this range, nominally two from the range of cartridges. A syringe filled with blood is inserted into a machine that injects the blood into the selected cartridge. Clot formation is used for end point detection. Within a few minutes, the cartridge having the proper amount of protamine is automatically indicated, along with a heparin concentration. Use of this device requires the initial correct estimation of heparin, requires a few minutes to run, and has accuracy limited to a discrete range of heparin concentrations based on the resolution of the protamine titration. Numerous cartridges must be stocked if the entire range of possible heparin concentrations is to be measurable. The cartridges have a limited shelf life and must be discarded if not used within the shelf life.

The titration of heparin with protamine has been studied in academic, laboratory settings, but has not resulted in any patient point of care devices that could be used to provide timely heparin concentrations to a treating physician. Several obstacles should be overcome in order to provide the ideal point of care heparin measuring device. A rapid and accurate measurement sensor, an accurate reference or baseline determining system, suitable disposable cartridges, and systems for handling and analyzing all of the above would be desirable and have not yet been developed.

SUMMARY OF THE INVENTION

The present invention provides methods and devices for automatically determining heparin (including low molecular weight and unfractionated heparin) concentration in fluids such as blood. The devices and methods of the present invention can be used in a point of care device, providing rapid determination of a patient's blood heparin concentration automatically.

Cartridges including protamine ion sensitive electrodes (ISEs) and reference electrodes and systems for automatically determining heparin concentration in the cartridges are provided. Some systems add blood to a protamine bolus sufficient to bind all heparin, leaving excess protamine. The excess protamine concentration can be determined by measuring the initial slope of the electrode potential rate of change, and comparing the slope to known protamine concentration slope values. In some cartridges, an oscillating pressure source moves the blood-protamine mixture back and forth across the protamine ISE.

In one method according to the present invention, a known volume of the blood sample is drawn or injected into a cartridge sample port, where the cartridge has been preloaded with a known quantity or bolus of excess protamine sufficient to bind all the heparin expected in the blood sample. The protamine can be positioned in the sample port or fluid path such that the protamine is mixed with the blood. The mixing is effected in some methods by applying a varying or oscillating pressure to the cartridge fluid path through a pressure port, which may be the same port or a different port as the sample port. This varying pressure can be applied through a motor driven syringe to vary vacuum and/or positive pressure to the fluid path, which can move the blood sample and protamine back and forth in the column to achieve mixing.

The blood-protamine combination can be moved to the protamine ISE region of the fluid path in the cartridge through application of pressure or vacuum, and allowed to wet the protamine ISE. The back and forth movement of the fluid column can be begun again, and the change in EMF measured for about one minute in some methods. A few EMF measurements can be taken starting a few seconds after the renewed fluid movement, and the slope of the EMF vs. time determined. A previous set of calibration values taken for known concentrations of heparin using a similar cartridge and method can then be used to obtain the unknown heparin concentration.

In one method, blood samples having known heparin concentrations have the initial slope measured using the apparatus. A plot of the log of the initial slope vs. the heparin concentration yields a substantially straight line. The higher heparin concentrations leave lower remaining protamine concentrations which produce a smaller protamine ISE EMF rate of change (lower curve slope). A calibration log plot of the initial slopes produces a substantially straight line relating the log of the initial slope to heparin concentration. Thus, taking the log of the initial slope can provide the heparin concentration for an unknown, by using the calibration data.

Protamine ISEs can include polyurethane polymer, DNNS ionophore, and NPOE plasticizer. The polyurethane may include hard segments and soft segments, where both hard and soft segments may include cyclic and straight chain aliphatic moieties having essentially no ester or ether groups. Some hard segments may include methylene diphenyl groups. Some reference electrodes have the same polymer, plasticizer, and ionophore as the measurement electrode, but with a different concentration of ionophore.

In one aspect of the invention, a method is provided for more rapidly performing an automatic titration of heparin with protamine. One such method includes dispensing protamine drop wise at a first rate into a heparin-containing sample while measuring an output from an ion selective electrode responsive to the protamine concentration. The protamine can be dispensed at a second rate that is less than the first rate after the electrode output exceeds a first threshold. The dispensing can be stopped when a stop condition is met, and the total amount of protamine dispensed into the sample determined, typically for a time prior to the stop point time. The heparin concentration can be determined as a function of the total protamine dispensed into the sample. The stop condition is often the determination that an inflection point or maximum rate of change of potential with respect to time has been passed.

One method further includes dispensing protamine into the sample at a third rate that is less than the second rate, after the electrode output exceeds a second threshold. In some methods, a rate of change in electrode output per time is determined and the maximum rate of change is tracked. Once this maximum rate of change has been passed and the rate of change has dropped below a change threshold, below the maximum rate of change, titration can be stopped. In some methods, the dispensing includes dispensing drops of protamine and counting the drops.

In another aspect of the invention, a method is provided for determining an initial heparin concentration in a sample, not requiring titration. In this method, a bolus of protamine is added to the sample sufficient to bind all the expected heparin in the sample. The heparin and protamine can be mixed and allowed to bind to each other. The amount of protamine remaining in the sample can then be determined using the electrical potential from a protamine ion selective electrode. The initial heparin concentration in the sample can be calculated using the protamine binding stoichiometry, the protamine remaining, the protamine consumed, and the initial amount of protamine. The protamine remaining is determined by measuring the slope of the voltage read from the electrochemical sensor, after a suitable time is allowed for stabilization of the sensor membrane EMF.

In another method, the sample can be divided into a plurality of samples, and several different protamine concentrations added to the plurality of samples. The electrode potential from a plurality of ion selective protamine sensitive electrodes in communication with the samples can be obtained. An electrode can then be selected having an intermediate output as between the plurality of electrode measurements. The heparin concentration in the original sample can be determined at least in part as a function of this electrode output. In one method, the electrode is selected that has the closest value to the mid-point between the maximum and the minimum electrode outputs observed.

In yet another aspect of the invention, a more accurate measurement of the heparin concentration is obtained by creating a sample blank using the blood sample to be measured. In this method, essentially all of the heparin in the blood sample is neutralized, bound, or degraded to create a reference sample. The output of a first ion selective electrode pair is measured after exposing the first electrode pair to the reference sample. A second ion selective electrode pair is exposed to the blood sample not having the heparin inactivated, bound, or degraded. In one inactivating method, the inactivating includes binding the heparin to polycations immobilized on to a solid matrix, for example, sepharose beads or magnetic beads.

The original heparin concentration is determined by correcting the second electrode pair output using the first electrode pair output. The original blood sample may be split into two streams, one with heparin and one without, and both measured at about the same time. This method can improve the accuracy of the heparin measurement by correcting for non-heparin contributions to the ion selective electrode. This aspect of the present invention can compensate for matrix related effects (e.g. hemodilution), which could cause variations in the end-points measured by the electrode pair.

In a related method, the second electrode pair is exposed to a subsequent blood sample containing a different blood sample than the first electrode pair. In this method, a reference, baseline signal may be obtained first for the patient's blood having the heparin removed or inactivated, followed by a series of subsequent heparin determining measurements that are corrected using the first, blank sample measurement. Such measurements can include binding the heparin using an immobilized protamine, poly(lysine), polymer A (cross-linked PEI (polyethyleneimine)), or the like (other polycations that are capable of strong binding to heparin such as polybrene). In a variation of this method, the heparin may be degraded using the enzyme heparinase.

In still another aspect of the present invention, an improved reference electrode design is used. A polyion selective electrode pair can be used including a first electrode having an ion sensitive membrane comprising a polymer, a plasticizer, and an ionophore present in a first, non-negligible concentration. A second electrode is also included, having an ion sensitive membrane comprising the polymer, the plasticizer, and the ionophore present in a second concentration that is higher than the first ionophore concentration. The electrode containing the ionophore present in the higher concentration can be used as the reference electrode, and used to correct the potential drift resulted from the sample matrix effect. In some ion selective electrode pairs, the polymer is a polyurethane, the ionophore includes dinonyl naphthalene sulfonate (DNNS), and the plasticizer includes 2-nitrophenyloctyl ether (NPOE).

The improved reference electrode can be used in method including exposing a first electrode to the solution and obtaining a first electrical potential. The second, reference electrode can also be exposed to the solution to obtain a second electrical potential. The polyion concentration can be determined by the potential difference between the two electrodes. There is typically only one electrode potential measured the difference between the working electrode and the reference electrode.

The present invention can include use of an ion selective electrode (ISE) sensitive to protamine that includes alternating hard and soft polyurethane segments. In some polymers, the soft segment includes straight chain aliphatic groups and cyclic aliphatic groups joined by the urethane groups. The straight chain aliphatic groups and the cyclic aliphatic groups preferably have no ether or ester groups, creating a lipophyllic backbone. In one such polyurethane soft segment, the soft segment is formed as a reaction product of dimer diisocyanate, with butanediol and/or dimer diol.

The polyurethane hard segment can include alternating methylene diphenylisocyanate portions and diols, for example, butanediol and/or dimer diol. The hard segment regions between the isocyanate derived groups can thus be either hydrogen or straight chain aliphatic hydrocarbons or cyclic aliphatic hydrocarbons which may have hydrogen or straight chain aliphatic groups pendent from the cyclic portions.

In some embodiments, this polyurethane having the above-described hard and soft segments can be mixed or blended together with one or more other polyurethanes, e.g., Pellethane. A polymer blend may provide improved performance relative to the each of the blended polyurethanes alone. In still another embodiment, a co-polymer formed of the above-described soft segments and hard segments, as well as segments found in one or more other polyurethanes, e.g., Pellethane, can provide a single polymer backbone that has the desired properties.

An ion selective electrode (ISE) that is sensitive to protamine can comprise one or more of the specialized polyurethane polymers described above. Some electrodes may include the plasticizer NPOE and/or the ionophore DNNS.

In yet another aspect of the invention a fluid column agitation and mixing method, and a related cartridge, is used to mix the titrant and the sample across the measuring electrode pair. In one embodiment, an analyte sample cartridge includes a body, a sample chamber disposed within the body, and an ion selective electrode disposed within the body and in communication with the sample chamber. A reference electrode is also disposed within the body and in communication with the sample chamber. The chamber can have a blind cavity disposed on a first side of the sample chamber and containing a compressible fluid. The chamber can further have a port disposed on a second side of the sample chamber opposite the blind cavity. This port can be coupled to an oscillating pressure source. The oscillating pressure source can cause the liquid sample placed between the oscillating pressure source and the blind cavity to move back and forth over the electrodes in the sample chamber responsive to the oscillating pressure source. An air column can be used for the oscillating pressure source. The fluid column agitation can be used to replace the magnetic stirring bar or magnetic stirring beads in some devices according to the present invention. Additionally, the fluid column agitation could be used jointly with a moving mechanical element like a stirring bar or beads in order to increase the amount of stirring activity.

In another aspect of the invention, a protamine titrant dispenser is provided for accurately and repeatedly dispensing the protamine titrant, for example, in a drop-by-drop manner. A flexible pouch containing a protamine solution can be disposed within a rigid housing hermetically sealed about the pouch. A volatile liquid can be disposed within the housing and outside of the pouch. A dispensing tube can be provided that is in communication with the pouch and extending through a gas tight seal in the housing. The volatile liquid will provide a vapor pressure in the hermetically sealed housing against the liquid containing pouch. The vapor pressure of the liquid will be a function of the temperature of the liquid. A controllable heating device for heating the housing can be provided and coupled to a controller. In this way, heating the housing increases liquid vapor pressure, which increases pressure on the pouch, which increases the fluid pressure through the dispensing tube. The measured pressure of the dispensing tube, the pressure within the hermetically sealed housing, and/or the inside or outside temperature of the hermetically sealed housing can be used to provide feedback control to the heating element disposed against the hermetically sealed housing. A controlled pressure can be used in conjunction with a Lee valve to drop wise dispense titrant. Use of such a vapor pressure source can replace syringe pumps currently in use for some titrations.

In one device according to the present invention, numerous several dried protamine aliquots which may each have the same concentration, are provided at several points along a tubular path. Dried protamine may be used as the aliquot. The quantity of dried protamine in each aliquot corresponds to the amount required to neutralize a known amount of heparin (e.g. each aliquot may correspond to 5 ug protamine which is sufficient to neutralize 0.5 units of heparin). The numerous aliquots of protamine can have ion selective electrodes positioned between the aliquots in the path, where the ion selective electrodes are sensitive to protamine. A predetermined volume of blood sample can be forced through the path, encountering in sequence, first a first protamine aliquot and mixing the blood sample (containing heparin) with this protamine aliquot. The blood sample, now having some of the heparin bound to the dissolved protamine, continues over the first protamine measuring electrode pair. The response of the electrode pair is proportional to the concentration of the free protamine in the sample. A negligible electrode response is seen if the quantity of protamine is insufficient to completely neutralize the heparin in the sample. The blood sample can then continue to the second protamine aliquot and mix with the next aliquot, further binding more of the heparin in the blood sample. The blood sample having the initial heparin further bound by protamine from the second aliquot can then continue to a second protamine sensor where the response is again measured. This may continue until the blood sample has flowed through all of the numerous protamine aliquots, mixing with the aliquots, and passing across all of the protamine measuring electrodes, recording the responses of each of the sensors in sequence.

The electrical potentials from all of the numerous protamine sensitive electrodes can be analyzed. The electrode having an intermediate value between the extremely low and extremely high values can be used to approximate the similar point which would be found in the titration of the heparin containing blood sample with sequential aliquots of protamine. In one method, the electrode having the value most closely approximating the mid-point between the highest and lowest electrical potential outputs is used as the inflection point in this "titration."

In another method, the blood sample can be split into numerous equal volume streams in parallel, with each stream each passing through and mixing with a different aliquot of protamine at essentially the same time. Each stream thus encounters a different, sequentially increasing, known predetermined amount of protamine. In some methods, this protamine is dried protamine that has been preloaded into the flow channels of the measurement cartridge. Each flow channel, after mixing with the respective protamine aliquot, then encounters an electrode pair disposed within the respective flow channel. The values from all the numerous protamine sensitive electrode pairs can be analyzed in parallel, with the electrode pair having an intermediate value between the extremely high and extremely low values used to approximate the potential at the titration "inflection point." The amount of protamine within this flow channel can be used to determine the initial heparin concentration in the sample through the normal heparin-protamine stoichiometric relationship known for that protamine sample heparin type.

In still another method, a device having a single electrode pair and numerous protamine aliquots along a tortuous path is used. Each of the protamine aliquots has the same concentration. A heparin-containing sample can be admitted through a sample port and pushed/pulled (e.g. through application of positive/negative pressure) to advance across the electrode pair. After a baseline reading is measured, the sample can be advanced across a first protamine slug, with back and forth movement to help mix in the protamine in the sample. The dissolved protamine from the slug neutralizes the heparin in the sample having the first protamine slug dissolved within and is retracted to the electrode pair and measured again. A potentiometric response is noted to the extent of free protamine in the sample. If the amount of protamine is insufficient to neutralize the heparin in the sample, no change from the baseline response is seen. This is repeated for each subsequent protamine slug, and stopped when the last slug is reached, until the inflection point is reached, or until a plateau is reached, depending on the method used.

In one method, dried protamine is preloaded into the sample chamber. Heparin containing fluid is later added and the initial change in electrical potential between the working ISE and the reference electrode is measured. A linear relationship between heparin concentration in the sample and the logarithm of the change in electrical potential/time i.e. log (dEMF/dt), can be used to determine the amount of heparin in the sample. The system can be calibrated by using samples containing known amounts of heparin and measuring the change in differential electrical potential with time, using similar electrode pairs to those that will be used to measure the unknown samples.

Some electrode pairs according to the present utilize a different protamine ISE composition. The membrane can include heparin in the polymeric material of the working ISE. Heparin binds very efficiently to protamine and can be used instead of the DNNS. Also, protamine can be used in a heparin ISE to bind the heparin and generate an electrical potential in response. The protamine and heparin can be used as ion exchangers for polyanion and polycation assays, respectively. The protamine and heparin can be immobilized in the polymeric matrix, and may be coupled to the polymeric backbone, for example, to polyurethane, in some embodiments.

DESCRIPTION OF THE DRAWINGS

FIG. 3A is a side view of a heparin concentration point of care determination device including two, tubular sealed vessels, each including a protamine ion selective electrode, a reference electrode, and a protamine syringe, where one of the two cartridges has had the heparin removed or inactivated to create a blank sample;

FIG. 3B is a prophetic plot similar to that of FIG. 2B, having differential EMF versus protamine infusion time for a heparin containing sample and a blank sample having the heparin removed;

FIG. 4A is a side view of another point of care heparin concentration determination device including a coaxially disposed protamine selective electrode and reference electrode, together with a protamine syringe;

FIG. 4B is a top, cross sectional view through the coaxial electrode pair of FIG. 4A;

FIG. 4C is a top, cross sectional view of an alternate configuration of 4A, with a side-by side electrode pair;

FIG. 4D is a side view of the electrode pair of FIG. 4C, showing the insulation removed over each electrode, with the working electrode covered with a protamine selective ISE membrane;

FIG. 5A is a front view of a screen printed planar protamine ion selective electrode, including a protamine ion selective membrane and a reference electrode, both printed on a substrate and extending to a bottom sample exposure region;

FIG. 5B is a transverse cross sectional view of the electrode pair of FIG. 5A, showing a protamine delivery channel disposed within the substrate;

FIG. 5C is a front view of the electrode pair of FIG. 5A incorporated into a cartridge having a sample well at bottom;

FIG. 5D is a side view of the cartridge of FIG. 5C;

FIG. 13A is a top view of a heparin concentration determination system including a tape bearing multiple ion selective electrode pairs extending from a sensor spool to a take up spool;

FIG. 13B is a front, detail view of the tape of FIG. 13A bearing the numerous protamine ion selective electrode pairs;

FIG. 13C is a detail view of one ion selective electrode pair from FIG. 13B;

FIG. 13D is a detail view of the sensor head of FIG. 13A;

FIG. 14A is a front view of a sensor having a single protamine electrode and multiple protamine aliquots;

FIG. 14B is a front view of another sensor, having a single protamine electrode, multiple protamine aliquots, and a serpentine path;

FIG. 29B is a top view of the two sensor cartridge of FIG. 29A;

FIG. 29C is a bottom perspective view of the two sensor cartridge of FIG. 29A;

FIG. 29D is a top perspective view of the two sensor cartridge of FIG. 29A;

DETAILED DESCRIPTION

Figure 1:
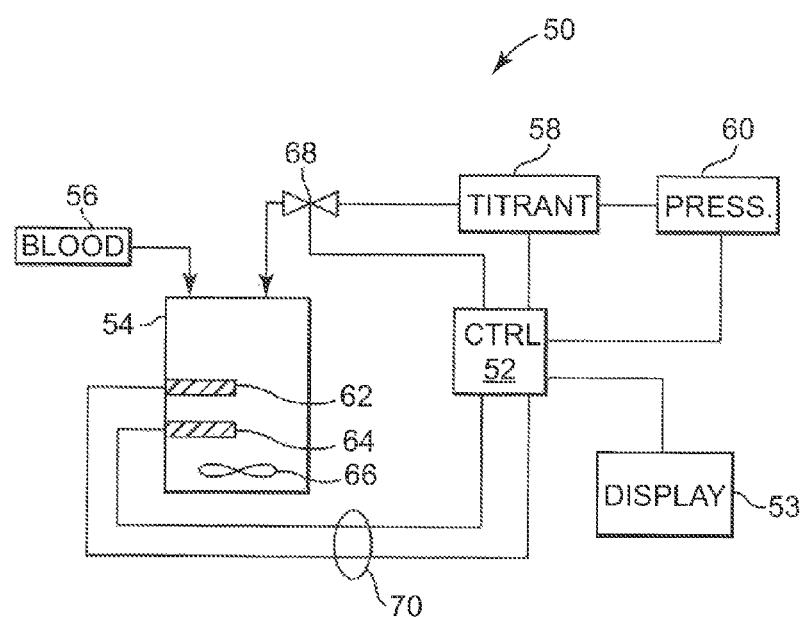
FIG. 1 is a schematic diagram of an automatic, point of care heparin concentration determination system including generally a controller, a titrant delivered using a pressure source, and a cartridge including a protamine ion selective electrode pair and a mixing element.

FIG. 1 illustrates generally a system 50 for measuring the heparin concentration in blood using a protamine titrant. System 50 can be implemented as a point of care system, which can provide rapid, non-clotting based methods for directly determining the heparin concentration in blood or other bodily fluids. This method is also broadly applicable to samples devoid/deficient of clotting factors (e.g. aqueous, platelet poor plasma etc.) and not measurable by clotting assays as well as colored or turbid samples (e.g. blood), which are not measurable by colorimetric assays. System 50 will vary according to the embodiment of the invention, as is discussed for the various embodiments below.

System 50 includes a controller 52 coupled to a display device 53. Controller 52 can be a hard-wired, electronic device formed of discrete analog and digital components in some embodiments. In other embodiments, controller 52 is a microprocessor-based, programmable device having at least one microprocessor therein. In yet another embodiment, controller 52 is a general purpose computer, for example, a desk top computer, running control algorithms to implement the present invention. One such controller is a general purpose computer executing the Lab View® computer program. Display 53 can be a dedicated, special purpose display on the device or it can be a general purpose computer display, for example, a CRT or LCD monitor. Various other input devices, for example, buttons, switches, knobs, keyboards, cursor control devices, and the like may also be coupled to controller 52, but are not shown in FIG. 1.

System 50 includes a cartridge 54 which may also be viewed as a sample chamber or a reaction chamber. Cartridge 54 is preferably a single use, disposable cartridge that can be readily coupled to the non-disposable portions of system 50. System 50 also includes a titrant source 58, a titrant control valve 68, and a titrant pressure source 60. The titrant is commonly protamine used at a pre-determined, fixed concentration. Valve 68 is a Lee® valve (or any such precision fluid dispensing valve) in some embodiments. In other embodiments, a syringe pump or other precision fluid-metering device may be substituted for titrant pressure source 60, and titrant source 58. Cartridge 54 typically contains a measurement electrode 62, a reference electrode 64, and a mixing element 66. Electrodes 62 and 64 as well as mixing element 66 can be electrically coupled to controller 52, for example, by wires 70. One component coupled to controller 52 is a high input impedance buffer amplifier, which enables it to perform a potentiometric measurement of the difference in the electromotive force (EMF) between the measurement electrode 62 and the reference electrode 64. A blood source 56 is also illustrated, to be fed into cartridge 54. For the purpose of titration, it is normally important that the volume of the blood sample be constant.

In one, highly diagrammatic use of one embodiment of the invention, a known, weight or volume of blood is injected into cartridge 54. The blood may be mixed with other, non-titrant chemicals such as sodium citrate, and disodium EDTA (ethylenediamine tetra-acetic acid). These two chemicals are anticoagulant chemicals to prevent the blood sample from clotting, useful when heparinized fresh whole blood is used as the sample, typically in liquid form. Mixing element 66 can be activated to mix the blood and the non-titrant chemicals, as well as the titrant, to be added later.

In a protamine titration of heparin, controller 52 can regulate the addition of protamine titrant at a fixed rate through valve 68, and monitor the difference in potential output from electrodes 62 and 64. In a general heparin-protamine titration, the protamine can be added until the inflection point in the sigmoidal titration curve has been passed. The amount (concentration) of protamine added at the inflection point of the titration curve can be determined by knowing the titrant (protamine) concentration, its infusion rate, and the sample volume. The amount of protamine required to reach the inflection point of the titration and neutralize the heparin is a function of the amount of heparin in the original sample. Since protamine binds to heparin with a fixed stoichiometry, the heparin concentration in the sample can be calculated from the protamine concentration required to reach the inflection point. Therefore, knowing the amount of protamine required to neutralize the heparin allows the calculation of the heparin in the sample.

In common practice, the titrant can be added at a constant rate, until the inflection point in the electrical potential has been passed and surpassed. To enable a rapid measurement of heparin in the sample, a gradient infusion of protamine may be employed. In such a method, the protamine titrant may be added rapidly until a first level of potential is reached, followed by a slower addition rate above that potential threshold.

In another such method, the protamine titrant is added at a third, even slower rate after a second threshold has been surpassed. By using slower protamine infusion rates close to the end-point of the titration, better resolution of heparin concentrations may be achieved. In addition, it allows a more rapid determination of the heparin concentration in the sample.

Heparin measurement in clinical samples may be "absolute" or "differential." In the absolute measurement of heparin levels, only one titration is performed with the sample. No correction is applied for any non-heparin contributions (matrix effects) to the end-point. In the "differential approach", the blood is split into at least two streams, with one stream having the heparin completely removed, neutralized or bound prior to entering a cartridge. A blood "blank" can thus be titrated in parallel with the blood still having the heparin, allowing for the potential to be corrected for non-heparin contributions. Different methods, described below, offer variations on the general method described above. In one method, pressure source 60 is a controlled, gas pressure source used to force titrant 58 through a valve at a known pressure and therefore a known rate, often in drop wise fashion. In some systems, the liquid is pushed through a narrow orifice. In one method, pressure source 60 is a vapor pump, formed of a titrant in a closed bladder disposed within a rigid canister having a volatile liquid-vapor mixture disposed outside of the bladder but within the rigid structure. Controlling the temperature of the rigid structure thus controls the vapor pressure of the liquid-vapor mixture and controls the pressure brought to bear on the bladder, which controls the pressure source of the titrant.

In some methods, mixing element 66 is a magnetically driven bead or other element. In some methods, mixing element 66 is an air column mixing device, described further below.

In one method, different from the titration method previously described, a bolus of titrant is added to cartridge 54, sufficient to totally neutralize the expected heparin in the blood. The concentration of protamine remaining is determined from electrodes 62 and 64, with the consumed protamine calculated and used to determine the initial amount of heparin present in the blood. This bolus method is described in greater detail below.

Cartridge Designs

Figure 2A:
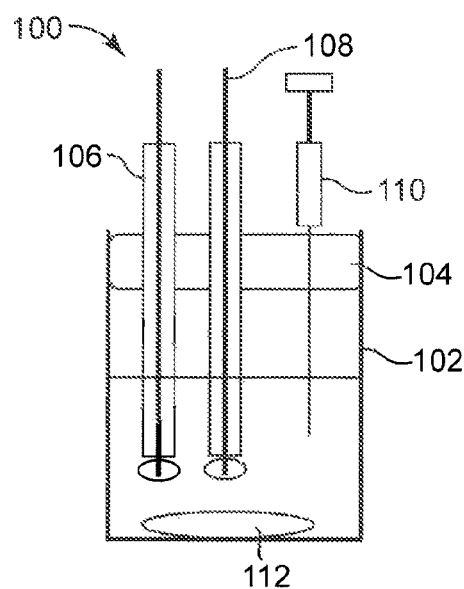
FIG. 2A is a side view of a heparin concentration measurement cartridge including a vessel sealed using a puncturable seal, a protamine ion selective electrode, a reference electrode, and a protamine syringe needle all in a vacutainer tube.

FIG. 2A illustrates one cartridge 100 that can be used to determine the heparin concentration using either the titration or bolus methods. Cartridge 100 includes a cartridge body 102 and a cartridge stopper or septum 104. Cartridge body 102 can be formed of glass, while stopper 104 can be formed of silicone rubber or Kraton®. Cartridge 102 can be formed within a vacutainer tube. The tube can be coated with EDTA, well known to those skilled in the art. Cartridge 100 can have a protamine sensor 106 and a reference electrode 108. Protamine sensor 106 may be composed of a protamine-sensitive polymeric membrane that is coated, e.g., dip-coated or drop-coated, over a silver (Ag)/silver chloride (AgCl) lead. The preferred composition of the protamine-sensitive membrane is described in other sections. The reference sensor 108 can consist of an Ag/AgCl lead that is directly exposed to the sample. A protamine syringe 110 is illustrated piercing stopper 104.

In use, the cartridge can be formed of a vacutainer tube of fixed volume and having a sensor and reference electrode embedded in the cap or septum and into the body. The blood sample can be delivered by piercing the cap using a needle. The vacuum can draw in the exact sample volume through suction. The cartridge can be placed in the instrument such that the electrodes make contact with the system and mixing initiated with a mixing element 112 to mix the heparin, protamine, and blood mixture. The protamine syringe can then pierce the cap and protamine injection commences the titration. In cartridge 100, the protamine pressure source previously discussed is the protamine syringe 110.

Figure 2B:
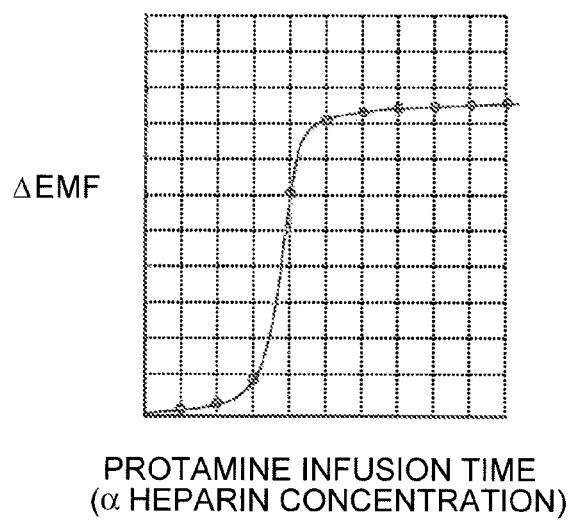
FIG. 2B is a prophetic plot of differential electrical potential between the working and reference electrodes versus time as protamine is infused into a heparin-containing sample.

FIG. 2B illustrates the differential electrical potential between the working electrode and the reference electrode over time as the protamine is injected into the sample.

FIG. 3A illustrates another cartridge 114. Cartridge 114 has electrodes 108 and 106 as previously described with respect to FIG. 2A. Stopper 104 and mixing element 112 can also be as previously described. Cartridge 114 includes a first portion 116 ("sample chamber") in which heparin will be present and a second portion 115 ("blank chamber") in which the heparin will be removed. The heparin can be removed from second portion 115 using heparinase or any other heparin degrading enzyme. In another method, an immobilized substrate, e.g., protamine, poly-lysine, poly-arginine, polybrene, or combinations thereof, can be used to bind essentially all the heparin prior to the blood being injected into "the blank chamber" cartridge second portion 115. In either case, the resulting fluid residing within cartridge second portion 115 will be substantially heparin-free, providing a control or blank which can be used to account for contributions from non-heparin contributions (such as matrix effects including hemodilution or other drugs). A protamine syringe 118 may be seen, having a first portion 119 inserted into cartridge first portion 116 and a second portion 117 to be inserted into cartridge second portion 115. As previously discussed, in some embodiments, two different channels of injection may be used, with one injection channel having heparinase or bound protamine to effectively bind or inactivate the heparin prior to the blood entering cartridge second portion 115.

FIG. 3B illustrates the differential electrical potential between the working electrode and the reference electrode over time for both the blank (the left curve) and heparin containing sample (the right curve) as the protamine is injected into each chamber. The end point of the blank chamber curve at left corresponds to the matrix effect. The end point of the sample chamber curve at right corresponds to the matrix effect plus the heparin, which prolongs the end point.

FIG. 4A illustrates another cartridge 120 having a coaxial, tubular protamine sensor and reference electrode. Cartridge 120 includes protamine syringe 110 and stopper 104 as previously described. Cartridge 120 also includes an EDTA coated vacutainer tube 122 having a coaxial measurement and reference electrode together in a single tubular electrode pair 121. Electrode pair 121 includes a protamine sensing electrode lead 126 disposed within an insulator 128 which is disposed within a tabular reference electrode 124 disposed within an insulator 125. The insulator layers 125 and 128 may be selectively stripped to expose the reference lead and the protamine sensor leads. A protamine sensitive polymer membrane may be selectively dispensed or coated onto the tip of the exposed protamine sensor lead 126 at bottom. The electrode pair 121 can offer the advantage of ease of manufacture, as both are incorporated in the same electrode cable.

FIG. 4B illustrates a transverse cross section of electrode 121. Proceeding from out to in, outer insulator layer 125 is followed by Ag layer 124 to be used as the reference electrode, followed by insulator layer 128, followed by Ag conductor 126 to be used for the working electrode. Proceeding from top to bottom, outer insulator 125 can be stripped to form the reference electrode, followed by inner insulator layer 128 which can be stripped to form the working electrode after coating with the ion selective electrode (ISE) membrane.

FIG. 4C illustrates a top, transverse, cross-sectional view of another an alternative version of the coaxial design with the electrode pair 390 having an insulator 391, a reference electrode lead 393, and a measurement lead 392. As shown in FIG. 4D, leads 392 and 393 can extend in parallel within insulator 391, with the insulator stripped off near the end. Reference lead 393 can have an ISE membrane coating 394 or remain uncoated, depending on the embodiment. Sensor lead 392 can have an ISE membrane coating 394.

FIGS. 5A-5D illustrate a planar protamine sensor and cartridge design. FIG. 5A illustrates a screen printed planar protamine sensor 130 from a top view. Sensor 130 can be made using screen printing or other depositing or layering technologies well known to those skilled in the art. Referring both to FIG. 5A and FIG. 5B, the sensor and reference leads as well as the protamine channels are incorporated in a substrate (base) material, which can be a thermoplastic polymer, polycarbonate, acrylic, or any other suitable substrate material. Substrate 132 can have a protamine delivery channel recessed into the substrate material, shown at 136. In some embodiments, channel 136 is a needle or a lumen. The protamine delivery channel 136 opens to the surface at the bottom of the substrate. The protamine channel 136 interfaces with the protamine delivery mechanism, for example, a syringe pump, to deliver protamine into the sample.

Continuing upward, conductive metallic strips may be deposited on the substrate, with a first conducted strip 133 deposited for the protamine sensitive electrode and a second electrically conductive strip 134 deposited for the reference electrode. Electrically conductive strips 133 and 134 may be formed of silver/silver chloride. The conductive strips may be deposited by appropriate techniques such as screen-printing, sputtering or chemical vapor deposition. An insulating layer 135 can be deposited over the electrical strips to electrically isolate them. The leads can be left exposed for electrical contacts 133 and 134 to interface with the data acquisition equipment. A protamine-sensitive polymer membrane 137 can be deposited over conductor 133 to serve as the working electrode. The portion 138 can be left as Ag/AgCl over conductor 134 to serve as the reference electrode.

In practice, sensor 130 may be incorporated as a side of an enclosed receptacle or sample chamber 139, illustrated in FIGS. 5C and 5D. The chamber is filled with blood (or sample) to a level above the two electrodes (137 and 138) and the protamine delivery channel 136. During measurement, protamine is delivered through delivery channel 136. Similar devices not having the protamine delivery channel as illustrated in FIGS. 5A and 5B may be used. In these, similar devices, protamine may be delivered using a different method such as a separate needle or channel incorporated elsewhere in the cartridge.

Figure 6:
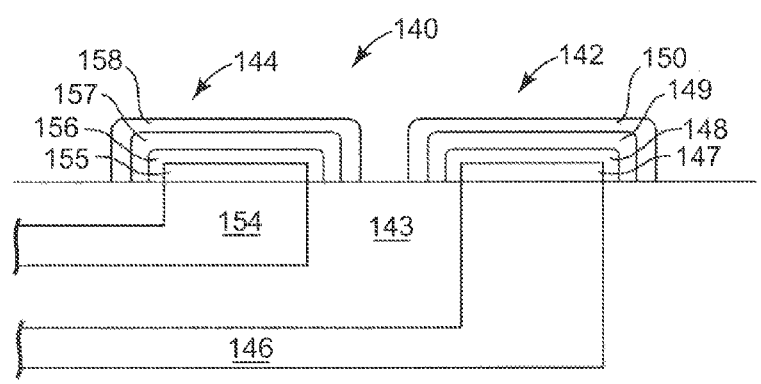
FIG. 6 is a side, transverse, cross sectional view of a protamine ion selective electrode including a protamine ion selective electrode and a reference electrode on a substrate.

FIG. 6 illustrates an electrode pair 140 including a measurement electrode 142 and a reference electrode 144. Electrode pair 140 includes a substrate 143 having a conductor path 146 for the measurement electrode and a second conductor path 154 for the reference electrode. Conductor paths 146 and 154 can be formed of silver or any other suitable electrical conductor. Measurement electrode 142, in the embodiment shown, includes a first layer 147 formed of silver chloride. A second layer 148 including a hydrogel is disposed over the silver chloride layer. Hydrogel layer 148 can be used in some embodiments to maintain the electrode in a moistened, hydrated condition, not requiring any hydrating prior to use. A third layer 149 includes the ISE layer. As is discussed below, one ISE layer includes a polymer, a plasticizer, and an ionophore to enable selective response to a specific analyte in the sample. As is discussed below, some electrodes use a lipophilic polyurethane having essentially no ether or ester groups in the backbone of the polymer. The polymer can include linear and cyclic aliphatic portions of the backbone as well as aromatic portions of the backbone, between the urethane groups. One set of electrodes utilizes DNNS as the ionophore for detecting protamine. Some electrodes utilize NPOE as a plasticizer. A top layer 150 may also be included, forming a protective layer over the other layers. The protective layer can be designed to have a high molecular weight cutoff, to allow only molecules below a threshold molecular weight to come in contact with ion selective electrode layer 149.

Reference electrode 144 varies with the various embodiments of the present invention. In the embodiment illustrated in FIG. 6, reference electrode 144 includes a first layer 155 formed of silver chloride, a second layer 156 formed of a hydrogel, a third layer 157 formed of a polymer, and a fourth layer 158 formed of a protective material. Layers 155, 157, and 158 can be similar to layers 147, 149, and 150, previously described. Polymeric layer 157 can, in some embodiments, be formed of the same polymer as ISE layer 149 and measurement electrode 142. Reference electrode 144 can have polymeric layer 157 be substantially similar to measurement electrode 142, but with polymeric layer 157 not having an ionophore while ISE layer 149 does have the ionophore. In some embodiments, protective layer 150 and 158 can have pores formed into the layers, to allow for diffusion of large molecules to the layer beneath. The various layers described in FIG. 6 can be deposited onto a substrate using many technologies well known to those skilled in the art, for example screen printing, casting, sputtering, chemical vapor deposition, plasma deposition, and/or drop wise deposition. Some such technologies utilize ink jet printing technologies which utilize specialized inks, dyes and/or chemicals. This ink jet-type printing can be used to repeatedly deposit materials in layers upon a substrate fed through the printing or layering device.

Some embodiments of the invention have no membrane or polymeric layer over the AgCl layer in the reference electrode. Some embodiments of the invention do include an ionophore in a membrane or polymer layer over the AgCl layer in the reference electrode, but in a substantially different concentration than present in the measurement electrode, as is discussed in more detail below.

Figure 7A:
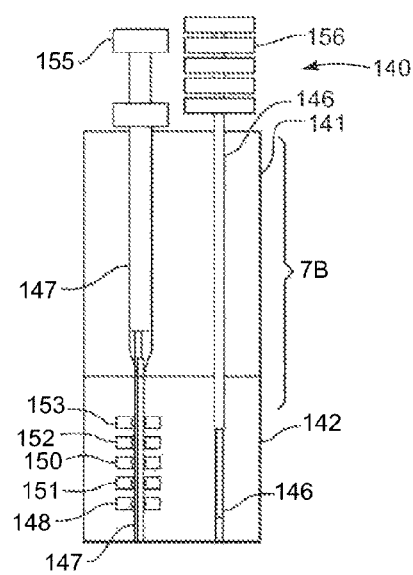
FIG. 7A is a front view of a protamine titration sensor including a bottom region having multi-analyte sensing capability.
Figure 7B:
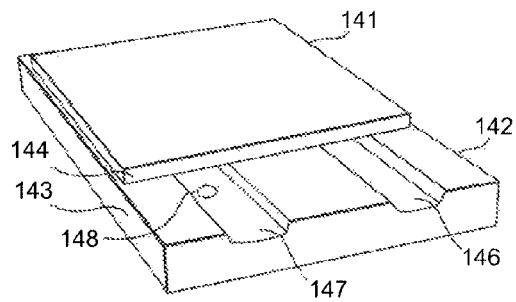
FIG. 7B is a fragmentary, perspective view of the bottom region of FIG. 7A, having a protamine entry channel and a multiple sensor channel.

FIGS. 7A and 7B illustrate a protamine sensor 140 having multi-analyte sensing capability. Sensor 140 includes generally an upper portion 141 which may have flow channels within and be enclosed, and a lower portion 142 which may have the flow channel exposed to a cartridge or sample chamber portion, as discussed with respect to FIGS. 5A-2DD. FIG. 7B illustrates part of top portion 141 and bottom portion 142, in a perspective view, showing an exposed calibrant delivery channel 147 and an exposed protamine delivery channel 146. The sample may be introduced to the sample chamber and bottom portion 142 using a needle or a delivery channel, as previously discussed. A protamine sensor 148 is shown in channel 147, where the reference electrode and other sensors (shown in FIG. 7A) may also be disposed in channel 147. Channels 146 and 147 may be formed in a substrate, as previously described, having here a bottom portion 143 and a top portion or cover 144.

Sensor 140 is a multi-analyte sensor. In the example illustrated, sensor 140 includes a reference electrode 150, a pH sensor 151, a sodium sensor 152, a potassium sensor 153, and protamine sensor or electrode 148. Other analyte sensors and electrodes can also be included in sensor 140. The sensors can be deposited in a cavity, in calibrant channel 147. The sensors other than the protamine sensor can be previously calibrated for their response slope prior to use.

Sensor 140 can include an actuator 155 to deliver the calibrant through calibrant channel 147, and a protamine actuator 156 to deliver protamine through protamine channel 146. The other protamine delivery sources discussed elsewhere in the present application may be used to deliver protamine in some systems.

In use, prior to sample introduction, a calibrant solution, containing known concentrations of each ion having a sensor, can be delivered through calibrant channel 147 and passed over the sensors. The volume of the calibrant solution can be much less than the sample volume, for example, less than 5% of the sample volume. This can serve to establish a baseline response for the sensors, Once the sensors have reached a steady reading, the sensor values can be noted and recorded.

Sample can then be introduced into the cartridge to contact the bottom portion 142 of the sensor, with mixing using methods and devices described elsewhere in the present application. The sensor output changes, other than the protamine sensor, are based on the analyte concentrations, with the response change being proportional to the analyte concentration, such that the Nernst equation can be used to calculate the analyte concentration. The response of the protamine sensor, and any other polyion sensors, can be analyzed as described elsewhere in the present application. Protamine titration (or bolus infusion) can be initiated, and the response of the protamine sensor output analyzed to determine the protamine concentration as before. Sample mixing should be continued during titration, to ensure the mixing of the protamine from channel 146 with the sample, to be sensed in the region of the sensors.

Figure 8B:
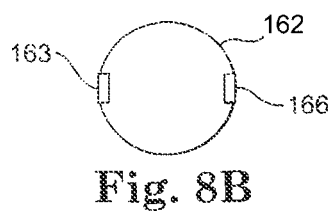
FIG. 8B is a top, transverse, cross sectional view of the planar electrode of FIG. 8A after the flexible substrate has been formed into a tube.
Figure 8A:
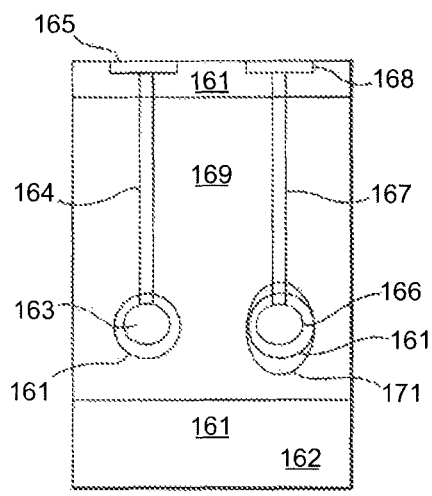
FIG. 8A is a side view of a planar sensor having a screen printed protamine ion selective electrode and reference electrode.
Figure 8C:
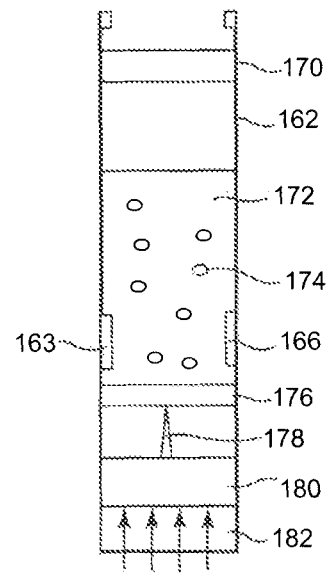
FIG. 8C is a side view of the tubular electrode of FIG. 8B incorporated into a cartridge having a sample within and a protamine injection device below.

FIGS. 8A, 8B, and 8C all demonstrate a planar sensor along with its substrate material that has been formed into a tubular receptacle to hold a sample. FIG. 8A illustrates a substrate 162 having a sensor lead 164 and reference lead 167 deposited on a substrate, including contracts pads 165 and 168, and reference pad 163 and ion, e.g., protamine, sensing pad 166. The leads can be deposited using screen printing or other methods described elsewhere in the present application. A dielectric layer 169 can be deposited over the leads, except for the regions indicated by reference numeral 161. An ion sensitive membrane such as a protamine sensitive membrane can be deposited to faun a pad 171 over pad 166.

FIG. 8B illustrates substrate 162 rolled into a tubular shape, with sensor electrode 163 and reference electrode 166 disposed on the inside of the tube wall.

FIG. 8C illustrates the tube of 8B from the side, showing again substrate 162 bearing electrodes 163 and 166. From top to bottom, a top seal 170 may be seen, followed by a sample solution 172 carrying several EDTA coated magnetic beads 174 within (EDTA coated magnetic beads may already be incorporated in the tube before sample introduction). The coated magnetic beads can be used to mix or stir the sample. A bottom plug 176 is also shown, which can be formed of Kraton®. Kraton can be used as the plug material to ensure that the cartridge can be completely sealed to form a vacuum to draw in the sample. Kraton is easily pierced by a needle and forms a tight seal around the needle, thereby preventing the sample from leaking out. A needle 178 may be seen for puncturing plug 176. A protamine source is highly diagrammatically illustrated at 180, being forced through needle 178 by a pressure source 182. Pressure source 182 can be a linear actuator, such as a syringe. At the completion of the titration, the needle may be pulled out.

Figure 8D:
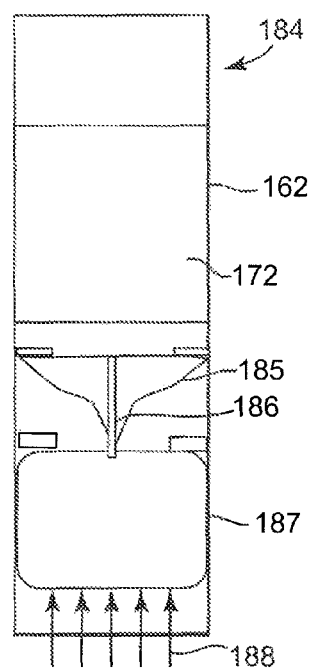
FIG. 8D is a diagrammatic side view of a cartridge similar to that of FIG. 8C, but having a protamine pouch advancing toward a needle to puncture the pouch to inject the protamine into the sample.

FIG. 8D illustrates a cartridge similar to that of FIGS. 8A-8C, having substrate walls 162 containing sample solution 172 as previously discussed. The electrodes, etc, of FIGS. 8A-8C are not shown in FIG. 8D. A hollow barb or needle 185 having a lumen 186 within is shown, disposed against a protamine containing pouch 187, which can be made of Kraton. A linear actuator 188 is diagrammatically illustrated, for pushing pouch 187 against needle 185. Needle 185 can have a gauge of 31 or higher (smaller diameter).

In use, upon initiation of titration, linear actuator 188 can push pouch 187 into barb 185, puncturing the pouch. The protamine can be expelled as a function of the needle gauge and the pressure exerted against the pouch. The pouch should have a reasonable thickness to prevent it from bursting.

Figure 9:
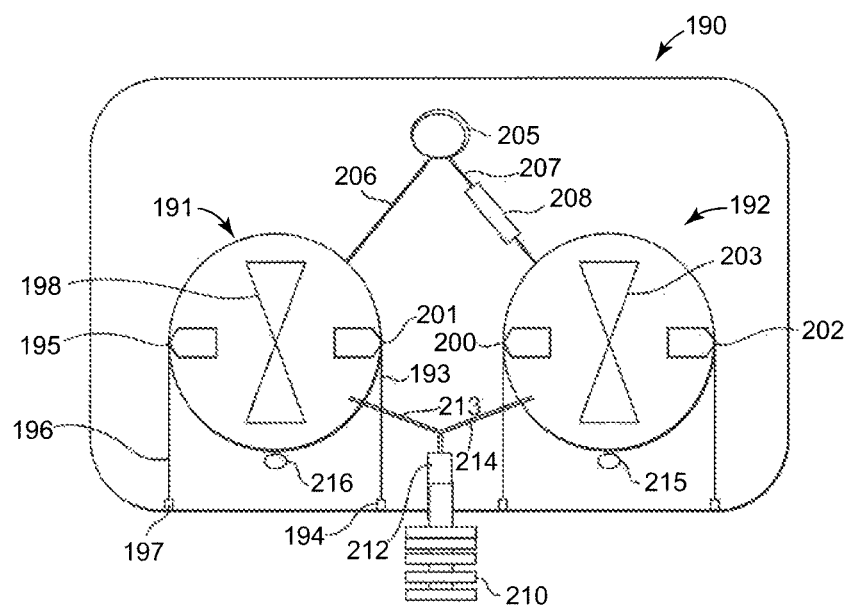
FIG. 9 is a top view of a differential planar sensor design with rotary stirrers, having a first chamber for heparin containing blood and a second chamber for blood devoid of heparin.

FIG. 9 illustrates a heparin-protamine sensor system 190 including a planar sensor design coupled with rotary or planar stirrers. System 190 includes a first sample chamber 191 to contain blood having heparin and a second sample chamber 192 to contain a blank sample, blood not having heparin. First chamber 191 includes a protamine sensor electrode 195 coupled to a conductor 196 coupled to a pad 197. Sample chamber 191 also includes a reference electrode 201 coupled to a conductor strip 193 coupled to a pad 194. A planar stirrer 198 is disposed within sample chamber 191 for stirring the sample chamber contents. The rotary stirrer may be a shaped magnetic stirring element that can be rotated to mix the contents of the chamber.

Similarly, second sample chamber 192 includes a protamine sensor 200, a reference sensor 202, and a rotary or planar stirrer 203. Chamber 191 and 192 can each be vented through Teflon® membrane plugs 216 and 215, respectively. This design allows for a self-regulating method for sample fill. As the user pushes the sample through the air or gas in the sample chamber, the air or gas is vented through the Teflon plug. When the liquid sample hits the plug, further introduction of liquid is made difficult due to the nature of the plug. The Teflon plug is typically in the form of a thin membrane or tape. In this configuration, it is typically microporous and functions as a good gas vent. The low wettability of Teflon and its small pore size prevents liquid from going through. By contrast, solid Teflon does not have this property.

A blood entry port 205 is coupled through a first channel 206 feeding first sample chamber 191 directly. A second channel 207 extends from blood entry port 205 through a heparin removal or inactivating chamber 208 which leads to the second sample chamber 192. Heparin removal or inactivating chamber 208 can include bound heparinase, mobile heparinase, bound poly(lysine) or bound protamine, polyarginine, polybrene or other heparin-binding polycations, which can all remove, inactivate, degrade, or neutralize the heparin prior to the entry of blood into second sample chamber 192. The heparinase or poly(lysine) may be immobilized on a suitable support, for example, cellulose or other suitable porous matrix that offers low resistance to sample flow.

A protamine solution source 212 is similarly coupled to the first sample chamber through channel 213, and second sample chamber through channel 214. In another embodiment, there is no tee coupling, having instead a separate protamine infusion channel from each pressurized protamine source. A linear actuator or other pressure source 210 can be used to force the protamine solution into the first and second sample chambers. Such differential measurement techniques employing a blank sample in conjunction with a heparinized sample provides a more accurate measure of the heparin concentration in the sample, because it accounts for the sensor response variations caused by matrix effects. The use of the heparin containing blood sample chamber and the blank sample chamber can be used to provide more accurate heparin measurements by adjusting the electrode potentials for the non-heparin contributions.

Figures 10A, 10B:
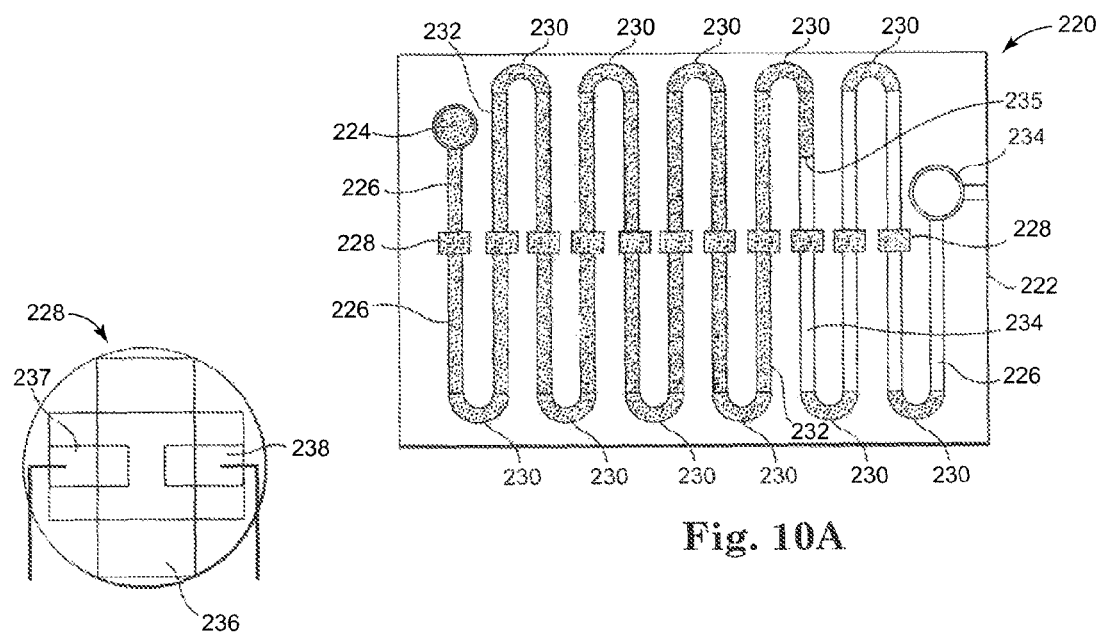
FIG. 10A is a top view of a serial protamine sensor having several protamine ion selective electrodes disposed between several protamine aliquots.
FIG. 10B is a top, detail view of a protamine ion selective electrode pair of FIG. 10A.

FIGS. 10A and 10B illustrate a heparin measurement system 220 utilizing multiple electrodes and multiple dried protamine contributions aliquots. System 200 includes a substrate 222 having a blood source or port 224 coupled to a serpentine flow channel 226 that is ultimately coupled to a sample withdrawal or suction port 234. Blood sample flow channel 226 extends through numerous protamine measuring electrode pairs or sensors 228. Protamine aliquots 230 (each preferably having the same concentration) may be disposed between the sensors 228. System 220 may be seen to have blood containing channel regions 232 leading up to a leading front 235 with essentially non-blood containing regions 234 thereafter. In some examples of the invention, protamine containing regions 230 contain dried protamine that can mix with the advancing blood flow and be carried to the subsequent protamine measuring sensors 228 downstream. In some embodiments of the invention, flow channel 226 relies on normal mixing of the blood and protamine resulting from flow. In other examples, flow-enhancing contributions such as turbulent inline mixers, sonication, or magnetically moved beads can be used to enhance the mixing.

FIG. 10B illustrates one protamine measuring sensor 228 in greater detail, including blood flow channel 236 having a protamine ion-sensitive electrode 237 and a reference electrode 238, previously described.

System 222 may be viewed as performing a stepwise titration of the blood sample with aliquots of protamine. In this stepwise titration, the initial protamine aliquots will be likely totally consumed in binding to the heparin. The electrical potential across the initial protamine sensors should thus be very low. As more protamine aliquots are added, at some point the protamine added will exceed that needed to bind to the heparin and will result in a rise in the electrical potential from the protamine measuring sensor. Further additions of protamine will result in progressively higher responses of successive protamine sensors and will finally result in essentially a plateau of the measurements response changes from the protamine sensors. Measurements from the protamine sensors having an intermediate value may be used to bracket the heparin concentration in the blood. While the inflection point of the titration or the maximum change in potential with time may not be located exactly, this location may be localized to within one or two segments of the multiple segment sensor system. The amount of total protamine added from the several aliquots prior to the protamine sensor having the intermediate potential value may be used to determine the total protamine entered up to that point. The stoichiometric binding ratio of the protamine may then be used to determine the heparin concentration in the initial sample.

In use, a fixed volume of sample can be introduced into the sample inlet port. The volume of blood may be controlled with a suction device in conjunction with valves. The blood sample is advanced over the first sensor pad. The response difference between the working and reference electrode is noted. The response of the first sensor pad is the baseline response, as no protamine is present in the blood sample at this point. In some methods, the sample is moved back and forth over the first sensor pad to allow the sensor to be exposed to a more representative sample.

The sample may then be advanced over the first protamine slug. The protamine can dissolve in the sample and neutralize any heparin present, to the extent possible by the limited amount of protamine present. Again, the sample may be moved back and forth over the slug to obtain better mixing. The sample can then be advanced over to the second sensor pad, and the differential response between working and reference electrode noted. The sample may be moved back and forth over any or all protamine slugs or sensor pads, depending on the embodiment. This advancement of the sample can be repeated until the sample is past the last sensor, until saturation is noted, or until an inflection point is found, again depending on the embodiment.

Figure 10C:
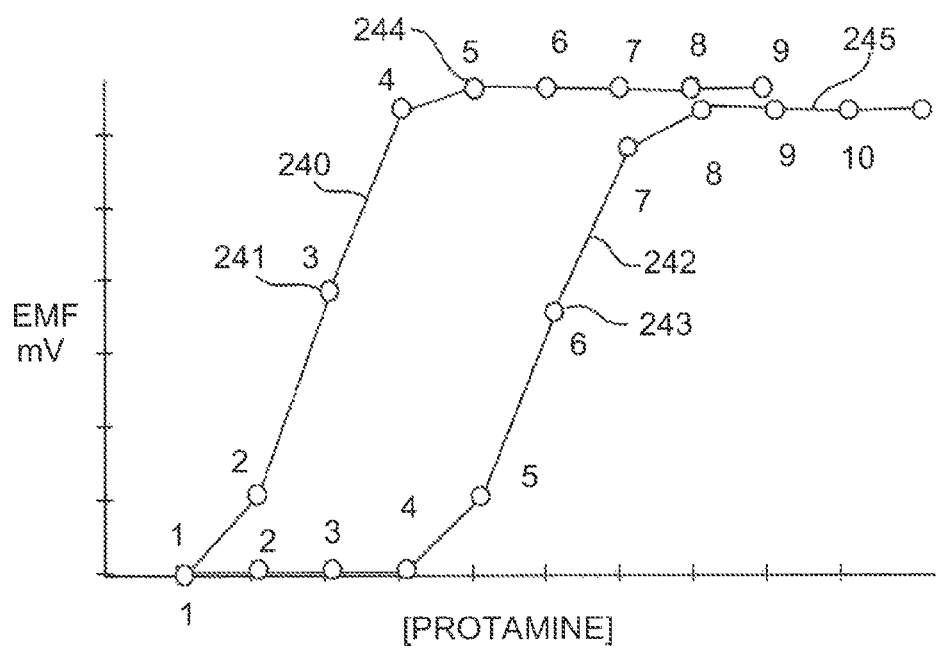
FIG. 10C is a plot of electrical potential versus sensor number from FIG. 10A, showing prophetic results for a low heparin concentration blood sample and a high heparin concentration blood sample.

FIG. 10C illustrates a prophetic example of a result of a titration from the sensor of FIGS. 10A and 10B for two samples having low and a high heparin concentrations. The individual points are labeled with the sensor number, with sensor #1 being the first sensor, positioned before the first protamine aliquot. The titration curve for a first blood sample having a low heparin concentration curve 240 may be seen in 240, having a low heparin concentration. In this example, the third protamine sensor in series has registered an intermediate value having a large rate of change of potential with respect to time, seen at 241. The total protamine in the two aliquots added prior to the third sensor may be used to determine the heparin concentration within a bracketed range. Continued protamine addition may be seen to result in a plateau at 244.

The titration curve for a second blood sample having higher heparin concentration may be seen at in 242. The lack of a response in the sensors 1 through 4 indicates that all protamine is utilized to neutralize heparin. The observation of a response at the fifth sensor indicates that the protamine introduced in aliquot 5 is in excess after neutralizing all the heparin in the sample. At the fifth sensor, some protamine remains. A maximum slope at the sixth protamine sensor is seen at 243. Subsequent protamine addition causes the responses from sensors 8-10 to be saturated and essentially results in the plateau seen at 245. The heparin concentration in the sample is proportional to the sensor near the greatest rate of change of differential potential versus sensor number. System 220 may allow disposing of eliminates the need for a syringe pump as sample advance may be accomplished by suction applied downstream of the sensors. In some systems, both positive and negative pressures may be used to move the sample back and forth over the sensors.

Figure 11:
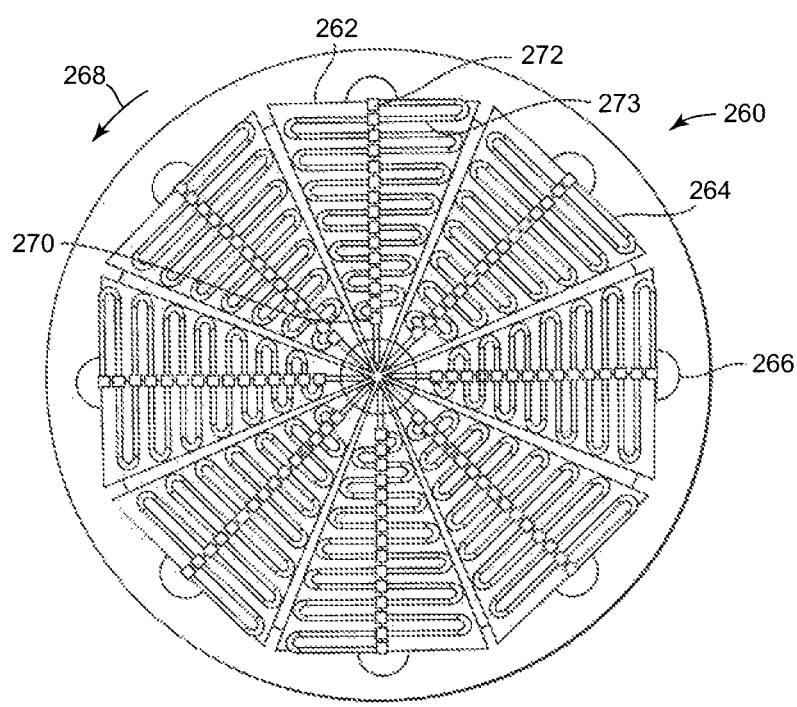
FIG. 11 is a top view of a multiple array sensor device including several serial protamine sensors similar to that of FIG. 10A.

FIG. 11 illustrates another sensor system 260 that includes multiple sensor systems such as that illustrated in FIG. 10A. Sensor system 260, in the example shown, shows eight systems somewhat similar to that illustrated in FIG. 10A. System 260 includes a first sensor pad array 262, a second sensor pad array 264, and a third sensor array 266. The eight sensor pad arrays can each include a serpentine or coiled mixing and measurement flow path 273 having a first end 272 and a second end 270. Once the measurement is complete, the sensor array can be rotated to expose the next sensing array and the sample process repeated. Such rotation is indicated at arrow 268. The multiple measuring sensors and multiple protamine aliquots are illustrated, as previously described with respect to FIG. 10A.

Figure 12A:
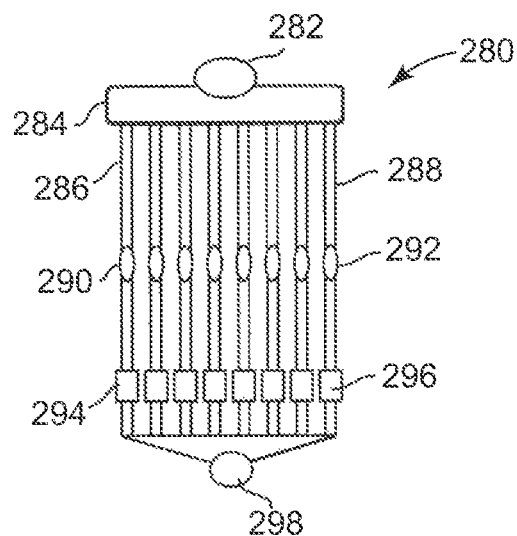
FIG. 12A is a front view of a parallel protamine ion selective sensor array having several flow channels in parallel, with each flow channel having a protamine aliquot upstream of a protamine ion selective electrode.

FIG. 12A illustrates another multiple sensor system 280 which shares some similarities with the system illustrated in FIG. 10A. System 280 operates in parallel while the system 220 of FIG. 10A operates serially. System 280 includes a sample entry port 282, a sample distribution manifold region 284, and multiple paths leading to a sample suction or withdrawal port 298. System 280 in FIG. 12A includes eight sample flow channels 286 through 288. Eight protamine aliquots 290 through 292 may also be seen. The number of channels eight, is only representative. In practice this could very well be more than that. Each of the multiple protamine contributing regions 290 through 292 can include increasing amounts of protamine. Finally, eight protamine measuring sensors 294 through 296 are also illustrated in FIG. 12A. The protamine measuring sensor from the array of sensors between 294 and 296 that registers an intermediate electrical potential value may be used to bracket the inflection point of the protamine "titration" of heparin.

Figure 12B:
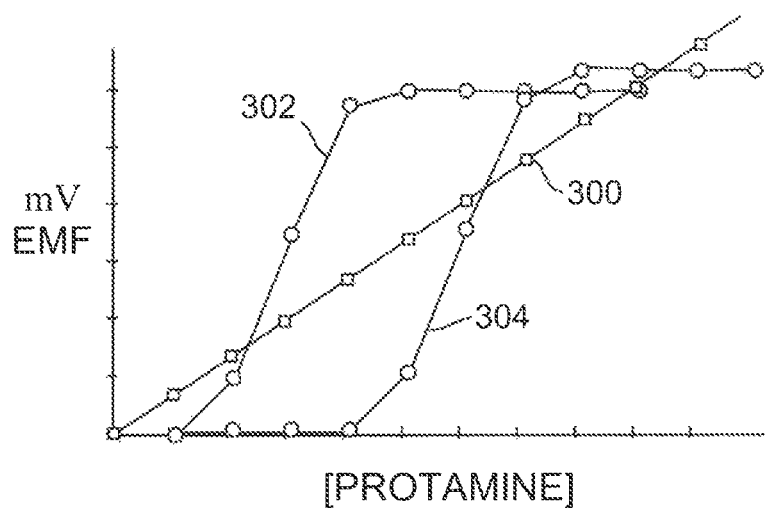
FIG. 12B is a plot of electrical potential from the protamine ion selective electrodes versus sensor number, show a prophetic result for both a low heparin concentration blood sample and a high heparin concentration blood sample.

FIG. 12B illustrates a prophetic result of using a multiple sensor array similar to the one shown in FIG. 12A, except that in this case the multiple sensor array has more than eight channels in parallel. FIG. 12B includes a plot of the protamine concentration versus sensor number at 300. Each sensor is exposed to a blood sample that has been mixed with an increasing concentration of protamine. The titration curve for a first blood sample having a low concentration of heparin is illustrated at 302, with the third lowest protamine concentration resulting in the electrical potential having the greatest rate of change. A second blood sample having a higher heparin concentration is shown at 304, with the sixth lowest protamine concentration channel having the greatest rate of change. A multi-sensor array system 280 may require more blood than system 220 of FIG. 10A. However, the parallel array system of FIG. 12A may benefit from having less sample loss by adhesion to the walls of the tubes and may also avoid cumulative problems of sensor wet-up times, as the sensors are arrayed in parallel rather than in series. A parallel design can allow the sample to be measured in a relatively short time period relative to a serial design.

FIG. 13A illustrates yet another multiple sensor system 310 for measuring heparin concentration using protamine addition. System 310 includes a sample inlet 312 for admitting blood samples coupled through a valve 313, a protamine reservoir 314, and a measurement chamber 318 containing a sensor window 336. A suction or positive pressure port 334 coupled through a valve 335 may be used to advance the blood sample from the sample inlet 312 through measurement chamber 318. A sensor tape 315 includes numerous new sensors 316 passing the sample chamber 318 and becoming used sensors 326. A sensor spool 322 can feed tape 315 bearing the sensors and be taken up by a take-up spool 324. A capstan 320 may be seen for carrying tape 315 past measurement chamber 318.

A wash reservoir 328 may be seen which can contain wash fluid used to clean measurement chamber 318 in-between samples and between use of the advancing new sensors 316. A waste reservoir 332 can be used to hold the used wash fluid from wash reservoir 328.

Figure 13E:
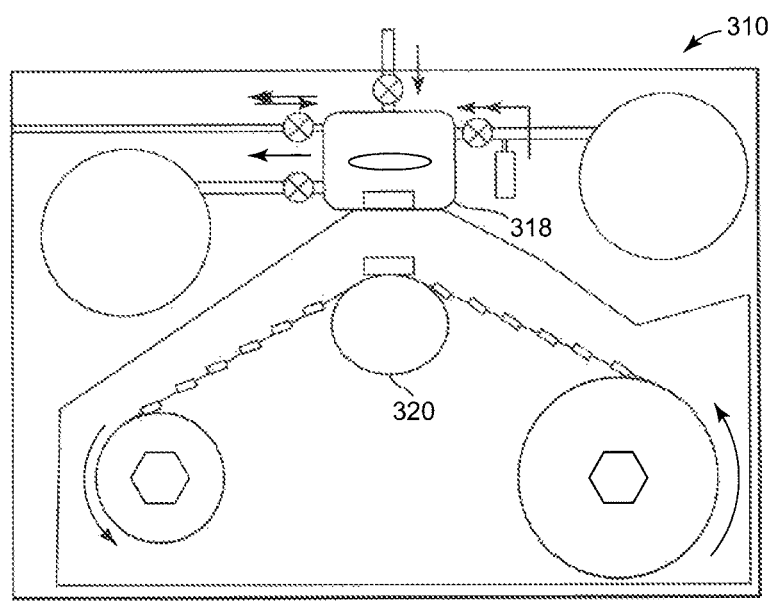
FIG. 13E is similar to FIG. 13A, but having the sensors and sample port pulled away from each other.

FIG. 13B shows tape 315 carrying numerous protamine measuring sensors 316. FIG. 13C illustrates one protamine measuring sensor 316 including a protamine sensitive electrode 317 and a reference electrode 319, as previously discussed. FIG. 13E illustrates measurement chamber 318 and capstan 320 retracted away from each other, allowing spools 322 and 324 to rotate to remove spent sensors 326 and advance unused sensors 316 to measurement chamber 318.

FIG. 13D illustrates measurement chamber 318 in greater detail. Measurement chamber 318 can include a sample port 340 (which is coupled to inlet 312 of FIG. 13A) coupled to a suction port 342 (which is coupled to port 334 of FIG. 13A) to draw the blood sample into the chamber 318. The blood sample is drawn into the chamber past the window 336. The sample chamber includes a sensor window 336 where the sensor may be positioned and held by the capstan 320 during sample measurement. A wash and protamine entry port 344 (which is coupled to 327 of FIG. 13A) may be seen coupled to a waste port 346 (which is coupled to 331 of FIG. 13A). Measurement chamber 318 is supplied with protamine from the protamine reservoir 314 for determining the heparin concentration through use of sensor 316, followed by a wash fluid to clean the sensor head, supplied from wash reservoir 328.

In one embodiment, sample inlet port 340, waste port 346, and titrant/wash port 344 are all located in bottom part of the sample chamber. Sample manipulation port 342 is located in the top part of the sample chamber. Electrical contact with the sensors may be made from the back of the sensors, with the electrical interface contained in the capstan mechanism 320, which also helps position the sensors 316 over the window 336.

In use, prior to starting the assay, the sensors can be positioned in the sample chamber window and the chamber window is sealed. In some devices, the seal is effected with the sensor tape being pushed into the window by capstan 320. Protamine sensor 316 is shown pressed against the window 336. The sample inlet valves and suction/blowing valves can be opened to actuate the sample.

Suction can be initiated through the suction port to draw the sample into the sample chamber. The sample volume can be controlled by the valve open time, metering, suction volume, or other suitable methods. The valves can be closed after the sample is drawn into the chamber. The valve on the titrant/wash port can then be opened to begin protamine titration. The linear actuator or other source dispenses protamine into the sample chamber and performs the titration. Once the titration is complete, the valve on the titrant/wash port can be closed. The tested sample solution can then be pushed to waste reservoir 332. This can be done by opening valves on the waste and suction/blowing ports and purging the sample chamber. Pressure can be applied from the blowing port to push the sample out of the chamber. Valves on suction/blowing port and titrant/wash ports can then be opened to wash the chamber. Suction can be applied through the suction port to draw wash solution into the sample chamber. The stir bar or other mixing element may be turned on to help in the wash process. The sample chamber may then be purged of the wash solution and dried by performing the same actions used to purge the sample chamber, with the wash solution being pushed into the waste reservoir 332. The sensor interfacing mechanism can then retract, thereby pulling the sensor away. The sensor spool can then advance to position the next sensor pad in the window to seal the chamber.

The suction/blowing port 334 of FIG. 13A can also be used (as shown in FIG. 13E) to alternately provide suction to pull blood through measurement chamber 318, followed by a positive pressure used to blow the wash fluid from measurement head 318. Thus, suction and positive pressure may be used sequentially to provide blood flow to the measurement head, wash, and blow dry the measurement head for a subsequent sample.

System 310 can thus provide a reusable well for containing sample and an advancing spool that contains single use sensors. A cassette can hold the wash and waste solutions and can be activated by a suction or blowing mechanism actuated by valves that open sequentially. This design is adaptable for inline sampling and multiple sample handling. Sensor capabilities can also be extended as necessary.

FIG. 14A illustrates still another system 360 for measuring heparin concentration using dried protamine aliquots. System 360 is similar to system 220 of FIG. 10A, with multiple slugs 365, 366, 367, etc, of the same concentration of protamine along a channel 369. However, the difference is that there is only one sensor pad 363 for making measurements. Further in this case, the sample 364 is moved back and forth between the sensor 363 and the protamine slugs, rather than being advanced in the same direction. The sample can be introduced through inlet port 361 and moved back and forth by positive/negative pressure being applied between inlet 361 and a second port 362.

In use, sample is introduced in the sample port 361. A fixed volume of sample is drawn into channel 369. Sample flows over the sensor pad 363 and a measurement, baseline response, is taken. Sample 364 is advanced to the first protamine slug 365, where the protamine dissolves in the sample. Protamine neutralizes any heparin in the sample (if present). The sample slug may be manipulated appropriately to ensure good mixing. The sample is pushed back to sensor pad 363 and a measurement is taken. If the amount of protamine is more than the amount of heparin in the sample, the sensor may show a response above the baseline. The sample is then advanced to the second protamine slug 366 and mixed. The process is repeated and the sample is brought back to the sensor pad for measurement. The process of pull/push is repeated. At every slug, more protamine dissolves in the sample. Eventually the protamine exceeds the heparin in the sample. The titration curve plots the response (dE) vs. the number of slugs that the sample has been exposed to. The titration curve for this design is similar to that of system 220 of FIG. 10A, except that the x-axis corresponds to the number of the slug, rather than the number of the sensor.

FIG. 14B illustrates system 370 for measuring heparin concentration using protamine addition. System 370 includes a first, sample port 371, a sensor pad 373, a tortuous channel 379, a second port 372, and protamine slugs 375, 376, 377, etc. System 370 is similar to system 360 of FIG. 14B, but having a tortuous channel. System 370 can be used in the same way as system 360.

Figure 15B:
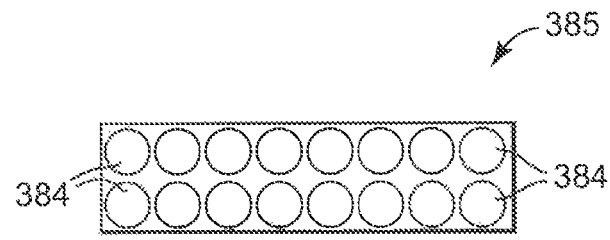
FIG. 15B is a top view of the sensor of FIG. 15A.
Figure 15A:
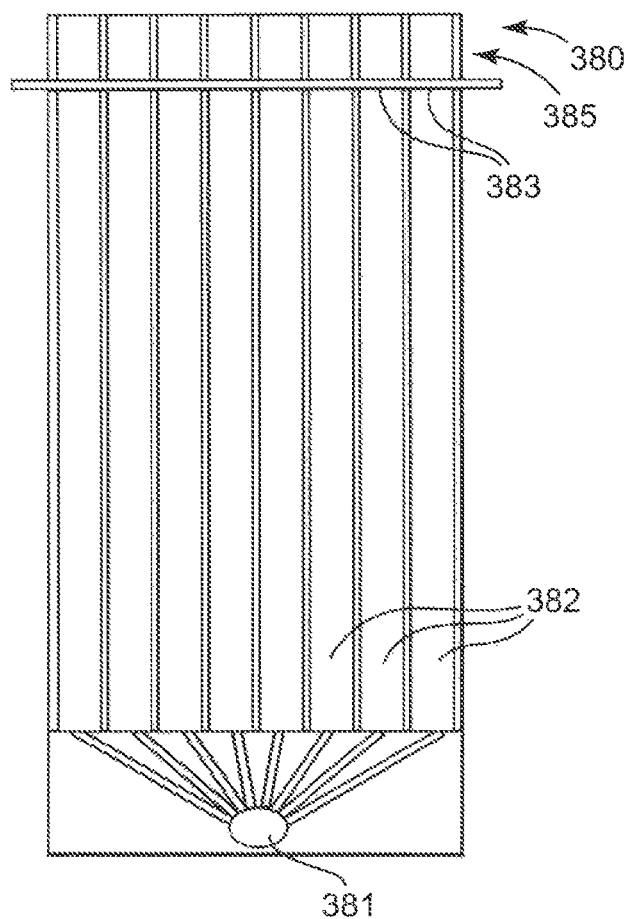
FIG. 15A is a front view of yet another sensor having a single protamine electrode and multiple protamine aliquots disposed in channels having individually addressable, controlled sample entries.

FIGS. 15A and 15B illustrate another system 380 having a sample port/sensor pad 381 in fluid communication with several channels 382 each having a protamine slug within. The channels have an increasing amount of protamine in each channel. The resulting method can be faster than a previous method because the protamine in all the channels is dissolved at the same time (as opposed to each being sequentially dissolved). Most of the analysis time in a measurement is spent in dissolving the sample and advancing it back and forth to the sensor. That process is not involved here which makes it faster.

In a first step, sample introduction and mixing step, all the channels are filled with a fixed volume of the sample which dissolves the protamine aliquots in each channel in the sample. In a second step, there is the sequential passage of the sample over the sensor. In this process the "protamine-dissolved" sample from channel-1 is first passed over the sensor and the response is recorded. Following this, the sample from channel-2 is passed and its response measured and so on. The order of passage of the samples is in the order of increasing protamine concentrations. As with the previous designs, once the protamine aliquot in a certain channel exceeds the heparin in the sample, the sensor shows a response corresponding to the free protamine in that channel (and increasing responses for the subsequent channels). This process is akin to the addition of incremental amounts of protamine to the sample.

Each channel can also have a gas permeable vent 383 which may include Teflon. The top of system 380 can include a valve manifold 385 having several individually addressable and controllable valves 384, so allow sample to be pulled into an individual channel to contact a protamine aliquot. System 380 is similar to system 280 of FIG. 12A, with the feature that it enables the protamine aliquots to be dissolved in parallel instead of in series. However, there is only one sensor instead of multiple sensors. In this feature it is similar to system 360 of FIG. 14A.

In system 380, the protamine slugs increase in concentration across each channel. The cartridge may be designed to have a vent plug that is gas permeable but liquid impermeable. A Teflon film could achieve this effect. This feature ensures that a fixed volume of sample is filled in each channel. Alternatively, the pump may be used to draw sample into each channel. Each of the channels is individually addressable using a system of valves (in the instrument). Suction/pressure can be used to manipulate the sample. A single sensor pad 381 is present at the confluence of these channels. This contains a protamine sensor and a reference electrode.

In use, the sample is dispensed in the sample inlet port 381. A fixed volume of the sample is drawn (or pushed) into each channel. The sample mixes with protamine in each of the channels. Mixing may be enhanced with appropriate aids. Each channel is individually addressed to push the sample over the sensor pad. The channels are pushed in order of increasing protamine concentration. The response of the sensor is recorded. The titration is performed by successively pushing each (protamine dissolved) sample over the sensor and measuring the response. Plotting the sensor responses vs. the channel gives the titration curve. The heparin in the sample corresponds to the channel at which the inflection point is observed. This method enables the sample to be measured in a relatively short period of time.

Figure 15C:
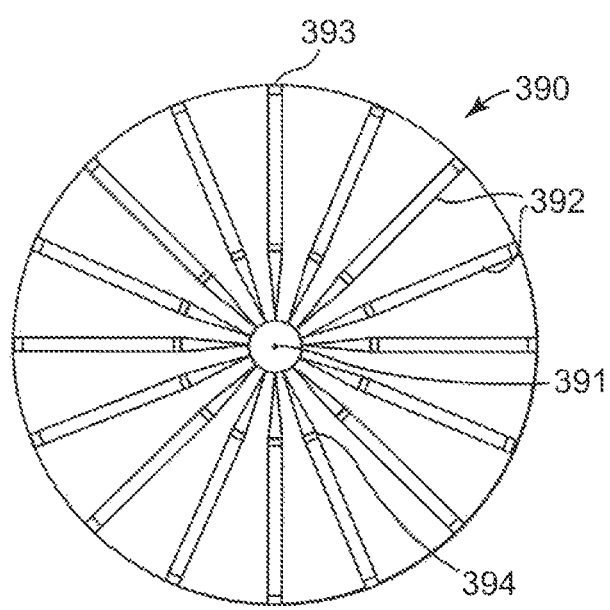
FIG. 15C is a top view of yet another sensor having a single protamine electrode and multiple protamine aliquots disposed in channels oriented as spokes radiating outward from a sample port, having individually addressable, controlled sample entries.

FIG. 15C illustrates another system 390 similar to system 380 of FIG. 15A, but circular. System 390 includes a central sample port/sensor pad 391, coupled to multiple channels 392 each having an increasing protamine aliquot in each channel 394, and individually addressable valves 393.

Protamine Bolus Method

As previously discussed, heparin can be measured in blood by using protamine to titrate heparin with the protamine-binding followed by using a protamine sensitive electrochemical sensor to monitor the titration endpoint. In this detection method, protamine is gradually introduced into the sample solution, with stirring sufficient to ensure a homogenous binding between the introduced protamine and the heparin in the sample. A relatively complex system would be required to infuse/dispense the protamine titrate, mix the heparin and protamine, and follow the titration progress.

In an alternate method, a bolus of protamine is preloaded into a cartridge. This protamine bolus should include a sufficient amount of protamine to completely neutralize the maximum expected heparin in the blood sample. The protamine bolus can be preloaded into a sealed cartridge, for example, and a known quantity of blood injected through the seal and shaken or otherwise mixed. After a suitable time period, the heparin-protamine containing solution can be injected into a second cartridge including a protamine sensitive electrode. The mixing and reaction can thus be done apart and away from the ion selective electrodes used to measure the protamine concentration.

Calibration can be accomplished using methods described elsewhere in the present application. For example, time to maximum rate of change of differential electrical potential, maximum rate of change of electrical potential, and the log of the initial rate of change of electrical potential can be used in conjunction with previously obtained calibration values for samples having known concentrations of protamine or heparin, depending on the method.

Thus, the starting protamine concentration, the final remaining protamine concentration, and the known stoichiometry of the protamine solution can be used to determine the heparin that bound the initial protamine. This bolus method can also be used where the mixing member is near the protamine sensitive electrode, by preloading or injecting a known excess quantity of protamine into the cartridge holding the protamine ion sensitive electrode.

With the use of preloaded dry protamine, the complex protamine infusing/dispensing system can be eliminated, thus dramatically simplifying the instrumentation. This method may also provide improved sensitivity. Since the sensor response depends on diffusion, a bolus of analyte will contribute more diffusion flux than small incremental analyte additions in more typical titrations. Thus applicants believe the bolus method will be more sensitive.

With the improvement of sensitivity, as long as an excess of high concentration of protamine remains after the heparin is neutralized, there would be enough flux into the sensor to provide a meaningful signal even without sample stirring. Therefore the stir system may be eliminated, thus further miniaturizing the sensor system.

This method can also be used to conduct multiple tests on the same cartridge and therefore on board calibration and parallel tests can be performed. If a stir bar or stir element is removed from the design, then any need to control each stir bar the same for each chamber may be removed. The reduced chamber or channel size may make parallel tests more practical.

Fluid Column Agitation

Figure 16A:
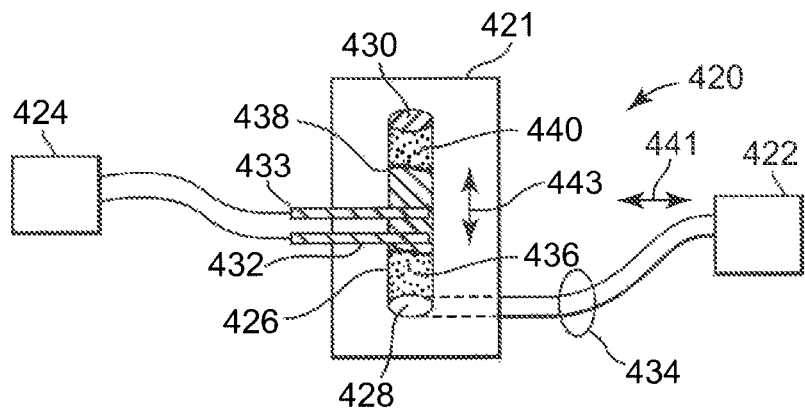
FIG. 16A is a schematic, top view of a heparin concentration determination cartridge having fluid column agitation.
Figure 16B:
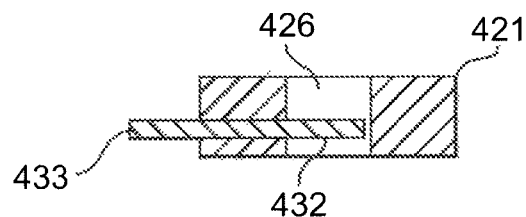
FIG. 16B is an end, transverse, cross sectional view of the sample cartridge of FIG. 16A.
Figure 16C:
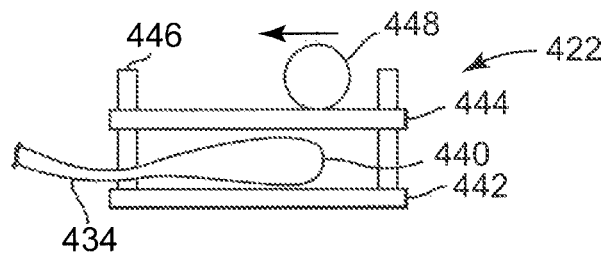
FIG. 16C is a diagrammatic, side view of one oscillating fluid pressure source for use with FIG. 16A including a rotating cam or eccentric bearing against a bladder containing air.

FIGS. 16A-16C illustrate a system for mixing and agitating a solution across the measurement electrodes. Magnetic stir bars and magnetic stir plates have been used to mix heparin protamine mixtures during protamine titration of heparin. However, this mixing method can limit miniaturization of the system. The present invention includes an oscillating fluid column for mixing the heparin and protamine mixtures, which can eliminate the need for a magnetic stirring member within the sample, chamber containing the electrodes. This may also allow for further miniaturization of the sample measuring cartridge.

FIG. 16A illustrates a system 420 including a sample measuring cartridge 422, an oscillating fluid pressure source 422, and an electrode measuring system 424. Cartridge 422 includes a sample chamber 426 within, containing electrode pair 432 that is coupled through wires 433 to measurement system 424. Sample chamber 426 may be seen to include three portions, a compressible fluid or gas filled portion 440, a liquid analyte containing portion 438, and an oscillating pressure portion 436. Oscillating pressure source 422 is coupled through a tube 434 to a port 428 in communication with the oscillating pressure portion 436 of sample chamber 426. The oscillating pressure source 422 may comprise air, which can be delivered with varying pressure through tube 434 to sample chamber portion 436. The compressible fluid or gas in sample chamber portion 440 may be air. A sample introduction port 430 may be seen which can be used for injecting the blood sample and the protamine into sample chamber 426. Protamine titrant can be infused through port 430 in some applications. Portion 440 is in effect a blind cavity which, being full of compressible fluid or gas, will shrink and expand in size in response to the varying pressure delivered through tube 434. A varying pressure is indicated at arrow 441 that causes the movement. Any fluid, gas or other compressible material not adversely affecting the measurement of electrodes and analyte can be used in portion 440.

Constant Pressure Titrant Source

Titration systems using a solenoid valve based liquid dispenser require an accurate pressure source to provide the driving force to dispense the liquid. Under the same valve opening parameters and constant pressure, accurate liquid droplet volumes down to the nanoliter can be dispensed. An easy to use, low maintenance, and low cost pressure source would be valuable for this application. In the present invention, this system can be used in heparin titration by precisely controlling the amount of protamine titrant that is dispensed. Current devices or titration volume dispensing often use a syringe pump. Others have used a liquid containing titrant pouch in a pressurized gas chamber, where the gas pressure is maintained by a gas pump. An easier to use, lower cost and easier to control titrant pressure source would be advantageous. In particular, a system not requiring a controlled syringe pump would be beneficial.

Figure 17A:
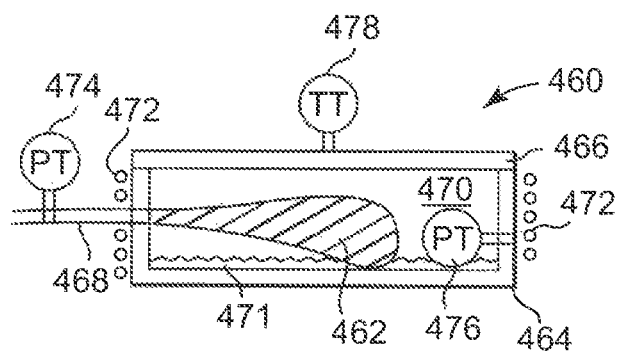
FIG. 17A is a side, transverse, cross sectional view of a titration constant pressure source including a protamine pouch in a hermetically sealed chamber having a volatile liquid and liquid vapor within.

FIGS. 17A and 17C illustrate a system 460 utilizing a chemical vapor pump. A chemical vapor pressure driven fluid source is presently being used in the Isomed® implantable drug delivery system, manufactured by Medtronic (Minneapolis, Minn.).

FIG. 17A shows system 460 including a hermetically sealed container including a bottom portion 464 and a top lid 466 threadably secured to bottom portion 464. A fluid filled, titrant containing pouch 462 is disposed within the hermetically sealed container. A volatile liquid, for example, the fluorocarbon FC87 (available from 3M, Minneapolis, Minn.) can also be included within the hermetically sealed housing. The volatile liquid is shown at 471 in a liquid phase and at 470 in the gaseous phase. The pressure delivered by the volatile liquid and brought to bear upon pouch 462 is a function of the temperature of the liquid within the hermetically sealed housing. The temperature of the housing and of the liquid within can be provided by heating coils 472 wrapped about housing portion 464. The pouch contents can be delivered outside of the hermetically sealed housing through a delivery tube 468 hermetically passed through the housing.

The pressure within tube 468 can be controlled directly or indirectly in several ways, depending on the embodiment of the invention utilized. A pressure transmitter or pressure transducer 474 can be used to directly measure the pressure of the titrant being delivered. Alternatively, a pressure transducer 476 can be disposed within the hermetically sealed housing to directly measure the pressure within the hermetically sealed housing. The pressure signal can also be passed hermetically through the housing. In yet another method, the temperature either inside the housing or of the housing itself may be measured by a temperature transducer 478. In any case, the delivery rate of the titrant should be used to calibrate the system, whether pressure or temperature measurements are used to control the delivery rate. It is expected that a drop wise delivery system for the titrant can be used in conjunction with system 460.

Figure 17B:
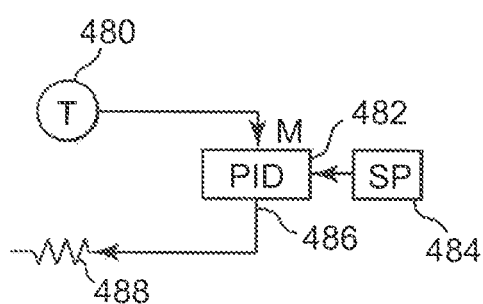
FIG. 17B is a schematic representation of a system for controlling the constant pressure device of FIG. 17A.

FIG. 17B shows a highly diagrammatic control system for controlling the pressure source to titrant delivery to 468. A transducer 480, which can be either a pressure or a temperature transducer, can deliver a measurement signal to a controller 482, which can be, for example, a PID controller. Controller 482 can accept a set point 484 given the desired pressure or temperature. Controller 482 can then output a control signal 486 that is used to control the heating through a resistance heater at 488 around the hermetically sealed housing.

A saturated vapor pressure can be generated by heating a liquid reservoir above its boiling point. The saturated vapor will reach equilibrium with its liquid phase in the same chamber. Self adjustment of the vapor volume will occur if the volume to be dispensed from the liquid pouch is reduced by dispensing. Hence a constant driving pressure is always present.

Reference Electrode Design for Polyion Electric Chemical Sensors

Potentiometric sensors have been widely used in clinical laboratories to measure potassium, sodium, chloride, and ph, etc. Sensor performance, such as precision, accuracy, and useful life depends very much upon the reference electrode. In particular, the stability and useful life of the reference electrode. When applying potentiometric sensors in whole blood tests, protein absorption on both working electrode and reference electrode will cause potential drift on both electrodes, even though the potential difference is measured between the working electrode and the reference electrode, and both electrodes will normally be different in material and design. However, the potential drift will not be cancelled out. For a polyion potentiometric sensor, even though it is a special type of potentiometric sensor, good performance depends very much upon the reference electrode performance.

The signal via differential measurement between the working electrode and the reference electrode will be a combination of the contribution by the true analyte activity/concentration difference and also by the contribution from the unmatched protein absorption, cell adhesion, and electrode hydration, etc. This contribution by protein absorption and cell adhesion is generally uncontrollable and irreproducible in most situations.

In another aspect of the present invention, this unmatched drift component between working and reference electrode is considered and at least in part accounted for by taking advantage of the unique response mechanism of the polyion potentiometric sensor. Surprisingly, the polyion sensor response time will be significantly different if the ion selective membrane is doped with a different amount of ion exchanger. The higher the ion exchanger concentration, the more time delay is observed in response to the same amount of polyion analyte in the sample solution. In prior art systems, if we start with a pair of identical sensor substrates, for example, two identical silver/silver chloride traces on polyester in current practice, only the working silver/silver chloride electrode contains the ion sensitive polymer membrane containing the ion exchanger.

In this aspect of the present invention, both the working and the reference electrodes are coated with the same polymer cocktail, but contain different concentrations of the ion exchanger. The reference electrode is preferably coated with the solution that has a higher concentration of ion exchanger, which will therefore be significantly delayed in response to the same amount of analyte in sample solution. Since by doing this, surface material of the working and reference electrode will be almost identical, i.e., having the same polymer and plasticizer, protein absorption and cell adhesion will be almost identical, and they can be cancelled out. The sensor hydration process will also be similar for both working and reference electrodes using this design. For comparison, under the previous design and fabrication, a significant potential drift will result owing to surface material difference between working and reference electrodes. Another property of this aspect of the invention is that any variation or variables in fabrication, especially in polymer membrane deposition, will likely be cancelled out by depositing the similar polymer cocktail on both electrodes.

In various embodiments, the ionophore concentration in the reference electrode is at least four, five, or ten times the concentration in the working or measurement electrode, depending on the embodiment.

Digitized Titration and Control Example for Protamine Sensitive Sensor System The present invention provides an automatic, digitized titration control system for automatically determining the heparin concentration in a blood sample through titration with protamine using a protamine ion selective electrode to determine the titration end point. In one embodiment, the present invention provides an automatic heparin protamine titration system having a reduced titration time while maintaining or improving accuracy. This system may be visualized with respect to FIG. 1, previously discussed. Instead of using a syringe pump to continuously deliver protamine into a disposable cartridge, digitized titration is realized by replacing the syringe pump with a liquid micro dispenser (Lee valve), which is capable of discretely shooting protamine solution in droplet form (less than 30 nanoliters per drop in this example) into the sample. The volume of every liquid drop can be controlled via the solenoid valve opening times and back pressure exerted on the protamine reservoir. FIG. 1 illustrates the pressure 60 on the protamine reservoir 58 supplying the valve 68 that is under control of controller 52. The control of this Lee valve is simple and the dispensing unit cost is significantly less than that of a syringe pump. The total amount of protamine dispensed for each test can be controlled on the sensor response and can be determined by a counter monitoring the valve opening pulses.

Figure 18:
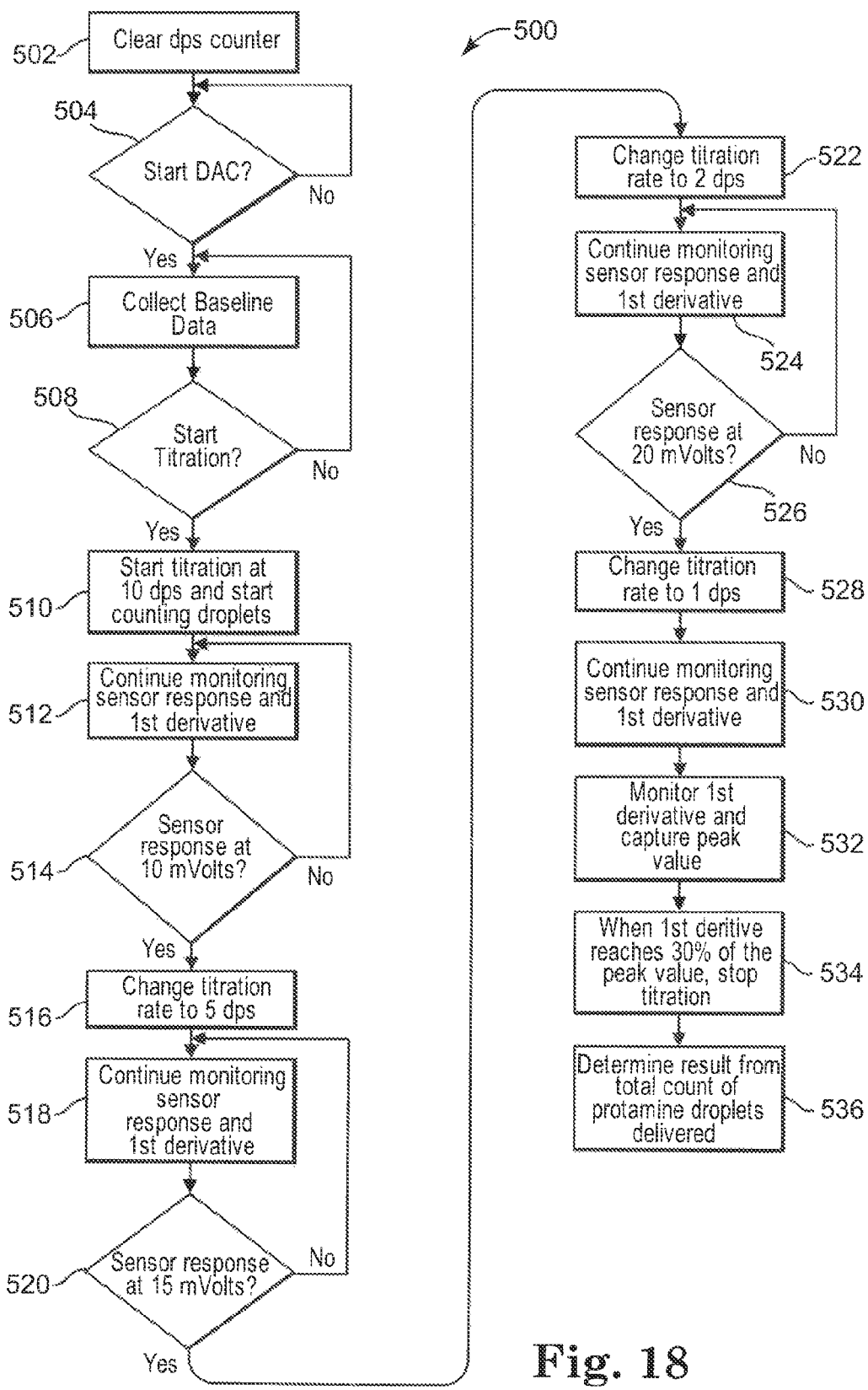
FIG. 18 is a flow chart of a method for titrating heparin with protamine using an adjustable droplet dispensing rate dependent on the potential received from the protamine sensitive electrode.

FIG. 18 illustrates one method that can be used to perform the automatic titration. This method can be implemented using a system similar to that illustrated in FIG. 1. Method 500 illustrated in FIG. 18 can be implemented in discrete analog and/or digital components, as firmware executable on a dedicated microprocessor control instrument, and/or as a computer program executed on a general purpose computer. Method 500, in this case, was executed as a Lab View executable program on a general purpose computer.

Beginning at step 502, the DPS (drops per second) counter is cleared. In step 504, if the data acquisition is to start step 506 is executed, otherwise the program loops at step 504 waiting for data acquisition to start. In step 506, baseline data is collected, for example, the beginning flat portion of the electrical differential plot.

Proceeding to step 508, titration is started if indicated. In one example, after a preset time has elapsed, for example 5 seconds, then titration may be begun. With execution proceeding to step 510, titration is started, for example at 10 drops per second, and the DPS counter begins counting droplets. In step 512, monitoring of the differential electrical potential between the working or measurement electrode and the reference electrode is monitored. The rate of change of the differential potential is tracked as well. Thus, both the absolute differential measurement and the rate of change of the differential measurement with respect to time are tracked. Proceeding to step 514, if the sensor response indicates a differential potential of at least 10 millivolts, then the titration rate is slowed at step 516 to 5 drops per second. If the differential electrical potential is not yet at 10 millivolts, then step 512 is executed again. In step 518, monitoring is continued, both of the differential electrical potential and the rate of change with time. At step 520, if the differential potential is at least 15 millivolts, then the titration rate is further dropped to 2 drops per second, otherwise step 518 is executed again.

In step 524, monitoring is continued, both of the differential electrical potential and the rate of change.

At step 526, if the differential electrical potential is at least 20 millivolts, then the titration rate is decreased to one drop per second at step 528, otherwise step 524 is executed again. At step 530, monitoring of the sensor response and the rate of change of the sensor is continued. The rate of change of the differential electrical potential can be monitored and stored, in various ways. In one, potentially noisy method, the rate of change is taken as the rate of change over two successive points. In another, less noisy method, a sliding window can be slid over a number of successive points, with the rate of change taken to be the rate of change from the first point in the window to the last point in the window over the time length of the sliding window. A number of filtering algorithms may be used as well. At some point, the rate of change will peak and then decrease. The maximum rate of change can be stored in memory. When the current rate of change has dropped to a threshold value below that of the maximum rate of change, the titration can be stopped. Capturing the peak or maximum rate of change is seen at 532. In step 534, when the rate of change reaches 30% below the peak value, the titration is stopped. In step 536, the time at the peak rate of change can be used to determine the total amount of protamine added at this peak time. In one method, the total number of drops is stored at each time interval along with the differential measurement for that time slot as well as the rate of change of measurement with time for that time slot. Given the total amount of protamine at the peak rate of change, the stoichiometry binding properties of the protamine may be used to determine the heparin bound at that peak. This determines the amount of heparin in the sample.

Figure 19:
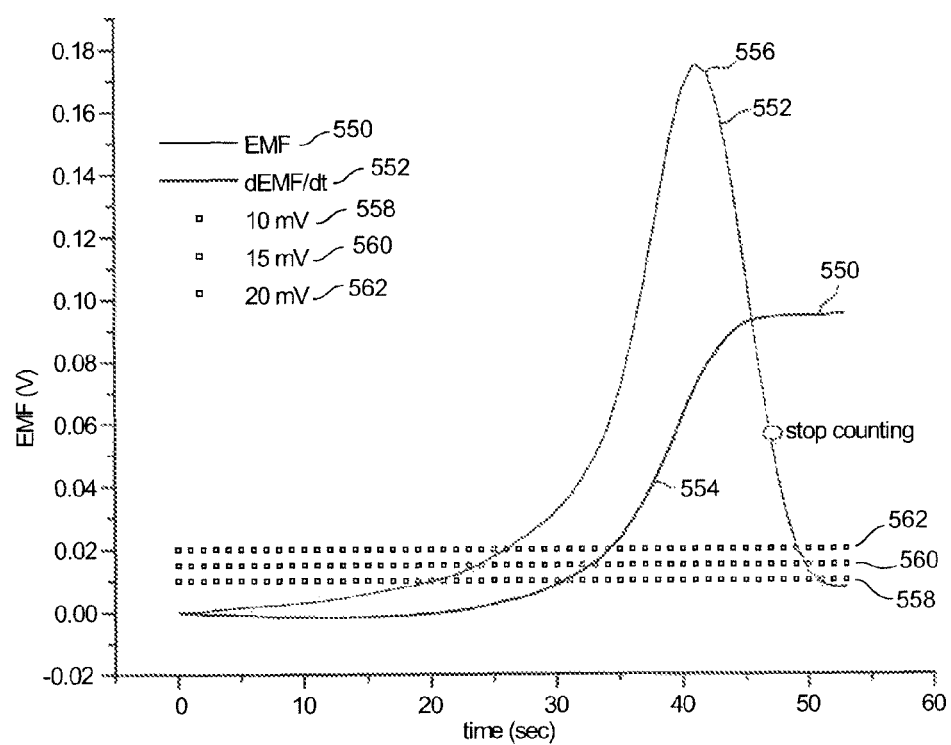
FIG. 19 is an experimental result, a plot of potential versus time and rate of change of potential per time versus time, for the adjustable droplet dispensing method of FIG. 18.

FIG. 19 shows a plot of the electrical potential between the measurement electrode and the reference electrode for the protamine ion selective electrode pair with respect to time. The differential potential is plotted at 550 with the maximum rate of change indicated at 554. The rate of change with respect to time of the differential electrical potential is plotted at 552, with the maximum rate of change indicated at 556. The rate of change may sometimes be referred to as the "first derivative", although it is typically measured using discrete points. The first differential potential threshold is shown at 558, which in the present example, is 10 millivolts. As previously discussed with respect to FIG. 18, when the differential potential reaches 10 millivolts, the titration rate drops from 10 drops per second to 5 drops per second. When the differential electrical potential reaches the second threshold at 560, which is 15 millivolts, the titration rate is dropped from 5 drops per second to 2 drops per second. When the third threshold at 562, 20 millivolts, was reached, titration rate was dropped to one drop per second. This allows a rapid infusion until threshold is reached, with a slower titration in order to more accurately capture the maximum rate of change of potential with respect to time at point 554.

Figure 20:
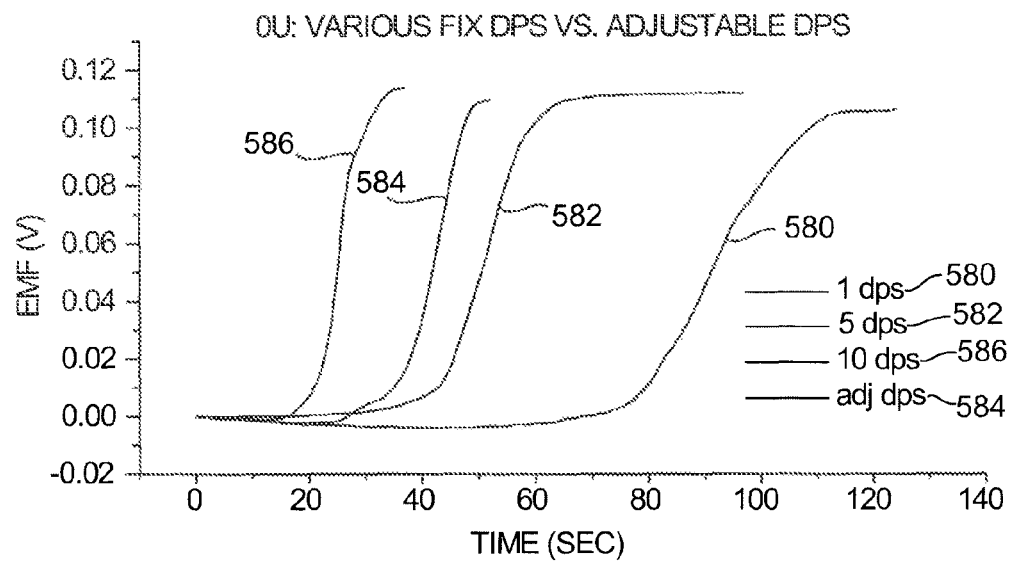
FIG. 20 is an experimental result, a plot of potential versus time, for various constant droplet dispensing rates, and the adjustable dispensing rate method of FIG. 18, where no heparin is present.

FIG. 20 illustrates an experimental result showing a protamine ion selective electrode response to protamine infusion in a sample having no heparin present. The plot of differential potential versus time for one drops per second is indicated at 580. As expected, this takes the longest time to reach the maximum rate of change and to plateau. The plot for 5 drops per second is seen at 582 and that for 10 drops per second seen at 586. The plot for the adjustable rate described in method 500 of FIG. 18 is seen at 584. The addition of 10 drops per second plateaued first and reached the peak rate of change first as expected. However, as the peak rate of change was approached more slowly, this point could be determined with more accuracy.

Figure 21:
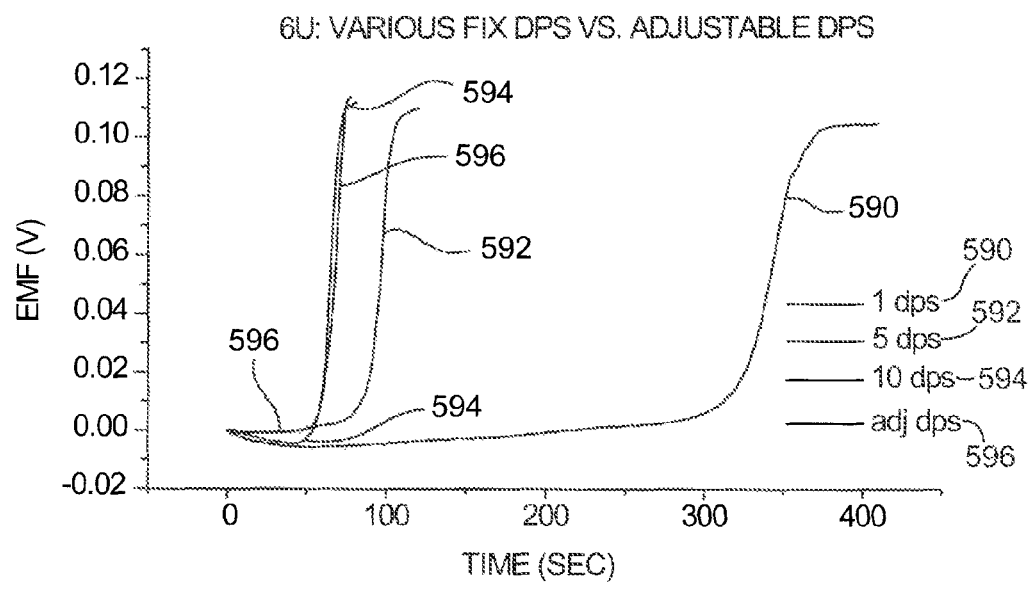
FIG. 21 is an experimental result, a plot of potential versus time, for various constant droplet dispensing rates and the adjustable method rate of FIG. 18 when 6 units of heparin are present.

FIG. 21 illustrates the protamine ion sensitive electrode response for titrating 6 units of heparin with protamine. The plot of one drop per second may be seen at 590, 5 drops per second at 592, 10 drops per second at 594, and the adjustable titration rate of Method 500 at 596. The adjustable rate achieves a result similar in time to that of 10 drops per second.

Figures 22, 23:
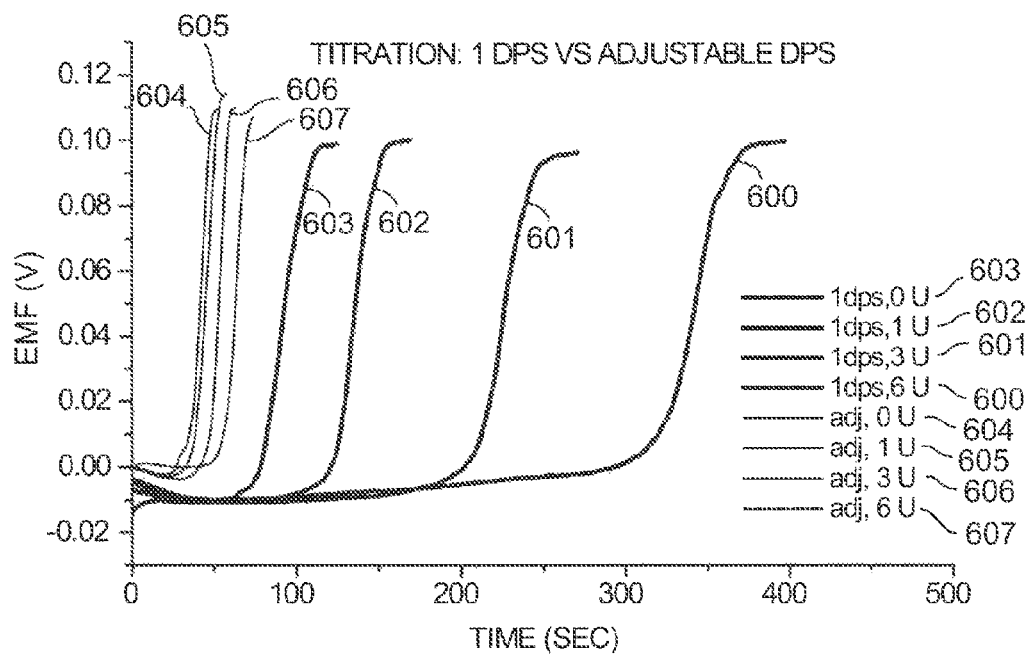
FIG. 22 is an experimental result, a plot of potential versus time, for titrating various amounts of heparin with both a slow, constant droplet dispensing rate, and the adjustable dispensing rate method of FIG. 18.
FIG. 23 is a table containing the experimental results of FIG. 22, showing a comparison of droplet counts for fixed versus adjustable droplet dispensing methods.

FIG. 22 illustrates another experimental result, showing the electrical potential versus time for various heparin amounts using one drop per second versus the adjustable method of FIG. 18. The plot showing the titration using one drop per second for zero units of heparin is indicated at 603, for 1 unit of heparin at 602, for 3 units of heparin at 601, and for 6 units of heparin at 600. The plots using the adjustable titration rate method may be seen for zero units of heparin at 604, 1 unit of heparin at 605, 3 units of heparin at 606, and 6 units of heparin at 607. As seen in FIG. 22, the adjustable rates shortened the test time significantly. For example, for 6 units of heparin present, the peak rate of change was located around 6 minutes using one drop per second while the corresponding peak rate of change was located around one minute using the adjustable method.

FIG. 23 illustrates the experiment results for the adjustable dispensing rate versus a 5 drops per second fixed rate to titrate 1 unit, 3 units, and 6 units of heparin. The adjustable rate dispensing method produced results having higher accuracy. FIG. 23 shows that for zero units of heparin, 262 drops were required to reach the peak rate of change compared to only 154 drops using the adjustable method. An overshoot or a reduced accuracy may be inferred from this result, in cases having non-zero units. For the zero unit case, this may be due to the ion flux provided being different, not an indication of overshoot or reduced accuracy. In the third column, the number of drops for the 1 unit, 2 units, and 6 units of heparin have been corrected by the number of drops required for the zero units of heparin. In the fourth column of FIG. 23, the ratio of the number of drops required for 3 units and 6 units relative to that for 1 unit is shown, which represents that the adjustable titration rate gives a truer ratio compared to the fixed fast dispense rate i.e. the numbers 1, 3, and 6.7 are closer to the 1 U, 3 U, and 6 U of heparin compared to the numbers 1, 6, and 11.8.

By using the present system, the titration of heparin at high concentration can be done within two minutes. Data analysis and display is simplified by correlating the sensor response, micro dispenser dispensing rate, and by counting the number of drops dispensed. By comparing the results obtained with the fixed high rate dispensing rate, the varied dispensing rate scheme can provide more accurate results.

Protamine Ion Sensitive Electrode

Figure 24A:
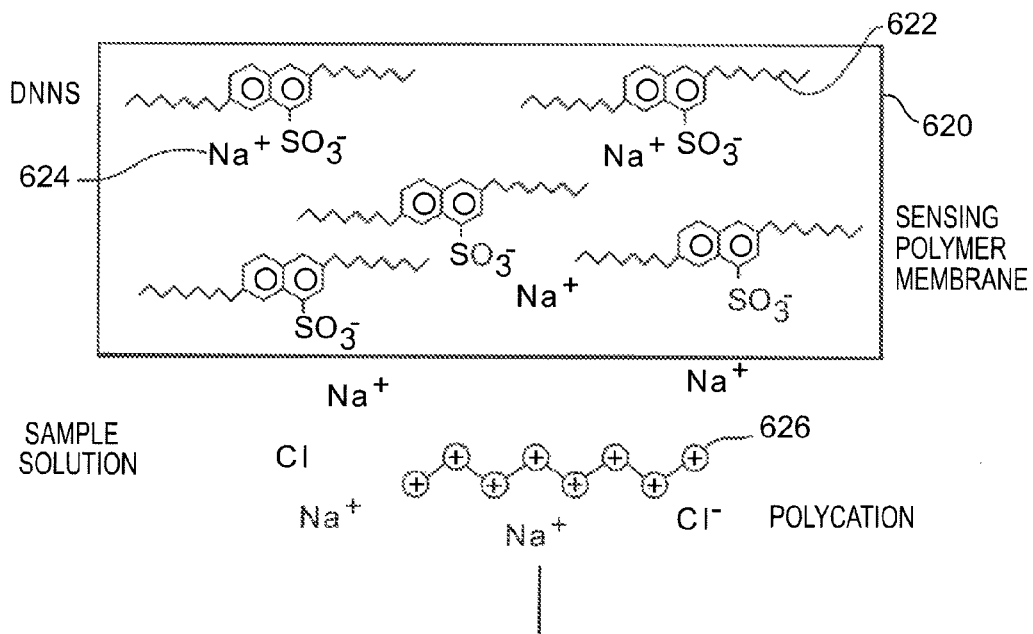
FIG. 24A is a diagrammatic representation of the protamine ion selective electrode membrane, including the ionophore DNNS before diffusion of the protamine polycation into the membrane.
Figure 24B:
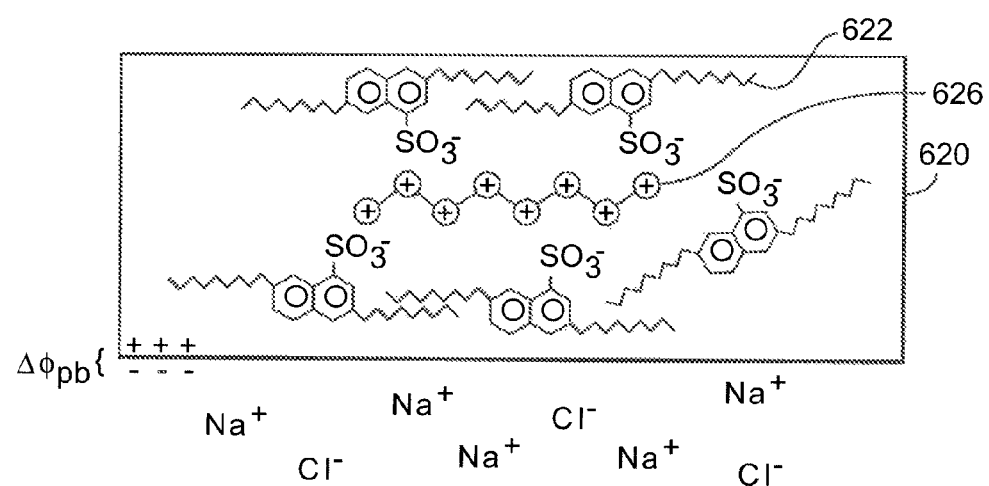
FIG. 24B is a diagrammatic representation of the protamine ion selective electrode membrane, including the ionophore DNNS after diffusion of the protamine polycation into the membrane.

FIGS. 24A and 24B illustrate a protamine ion sensitive electrode at 620 including numerous ionophore or ion exchange molecules at 622. FIG. 24A illustrates the membrane before protamine binding, and 24B after protamine binding. The preferred ionophore is DNNS, having $SO_3^-$ pendent groups. The DNNS ionophore may be seen complexed with sodium ions at 624. A polycation, such at protamine, may be seen at 626. At the bottom of FIG. 24B, membrane 620 may be seen having ionophores 622 complexed with protamine 626 which results in a positive electrical potential, either measured directly from the positive charge of membrane 620 or by driving off sodium ions 624 which then increase the electrical potential of a conductor and cause current flow through the measuring circuit.

Potentiometric Polyion Sensors Using Immobilized Polyions

Currently, for polyion sensors, the polymer membranes are doped with appropriate lipophilic anion or cation exchangers, such as tridodecylmethylammonium (TDMA) for polyanions and dinonylnapthalene sulfonate (DNNS) for polycations. The sensor response is based on the electrostatic interactions between DNNS or TDMA and polyions inside the membrane. However, these bindings are not effective, and the total voltage change is relatively small. One aspect of the present invention includes a new kind of ion-exchanger. Immobilized polyions such as protamine and heparin, for example, in the backbone of the polymer matrix molecule, can be used as ion exchangers for polyanion and polycation assays, respectively, which increase the total potential change and decrease the detection limit.

Compared with DNNS or TDMA, this new type of ion-exchanger may offer several features. First of all, the interaction between immobilized protamine or heparin and other polyions are very strong with high binding constants. This would increase the total potential change of the polyion sensor. Secondly, since the ion exchanger is immobilized in the polymer matrix, the diffusion coefficient of ion-pair in the membrane will be decreased so that a low detection limit can be obtained. Due to the large binding constants, this new kind of sensor will show a high voltage change and increase the signal to noise ratio for polyion measurement in whole blood samples.

Calibrating a Protamine ISE

In previous methods, various amounts of heparin were first spiked separately into 1 milliliter of phosphate buffer in disposable cups containing protamine sensitive sensors. Then protamine titrations were done by using drop by drop protamine injection into the cups. In the new method, various amounts of protamine were mixed with 1 milliliter of phosphate buffer in disposable cups first, then the sensors were put into the cups. This mimics a real application scenario, where a known amount of protamine will mix with the sample containing an unknown amount of heparin first, then the sensor is applied to measure the reduction of the protamine in quantity. This is referred to elsewhere as the bolus method in the present application.

Figure 25:
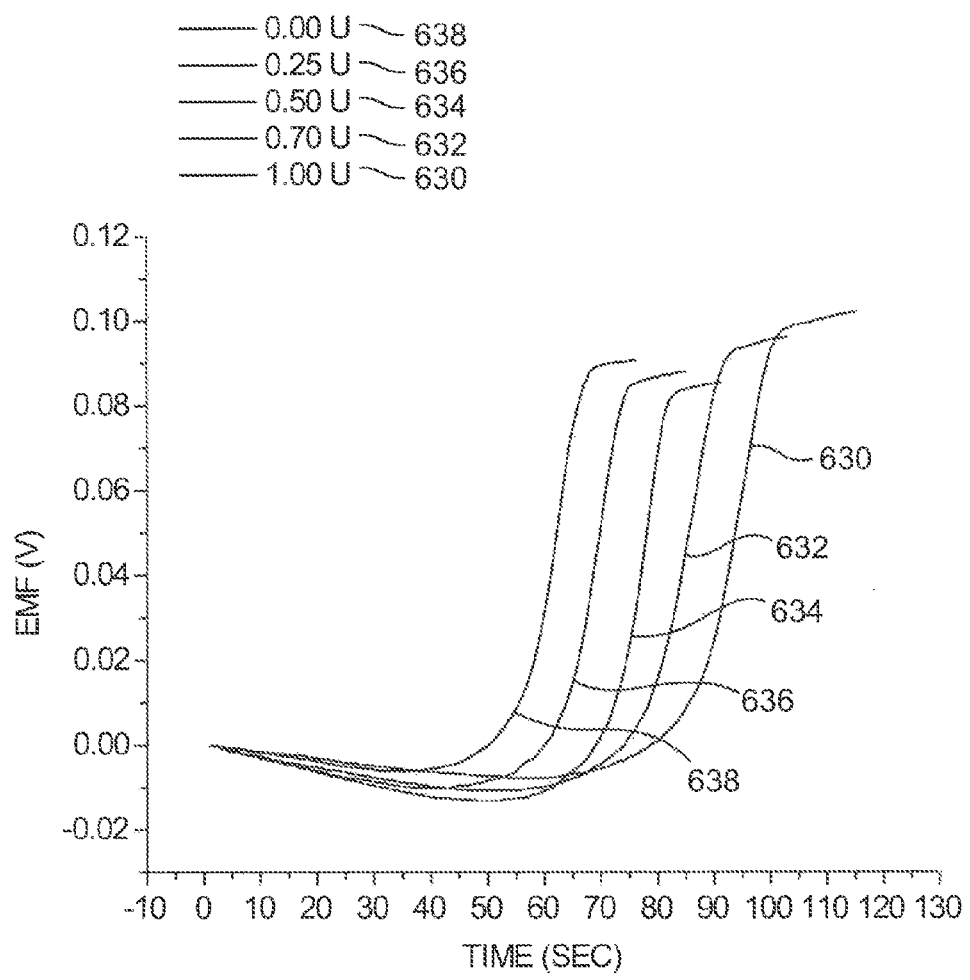
FIG. 25 illustrates the experimental results of titrating various amounts of heparin with protamine, shown as a plot of potential versus time.

FIG. 25 illustrates the experimental results obtained with the previous method, discussed above. The changes in electrical potential with time are shown for various amounts of heparin. The x-axis of FIG. 25 is labeled time but may also be viewed as the cumulative amount of protamine added, rather than time. This assumes a constant titration rate for the protamine infusion. The increase in potential with time for zero units of heparin is indicated as 638, for 0.25 units at 636, for 0.50 units at 634, for 0.70 units at 632, and for 1 unit at 630.

FIG. 26 illustrates experimental results using the new method. In this new method, a fixed amount of protamine is added to the cup, and varying amounts of heparin are added. In FIG. 26, the same amount of protamine is present in all of the sample cups for all of the heparin concentrations shown. Various amounts of protamine were put in 1 milliliter of phosphate buffer. 5 micrograms of protamine were put in 1 milliliter of phosphate buffer, with the results indicated at 660. 6 micrograms, 7 micrograms, 8 micrograms, 10 micrograms, and 14 micrograms, were also put into 1 milliliter of phosphate buffer, with the results indicated at 658, 656, 654, 652, and 650, respectively.

Figure 26A:
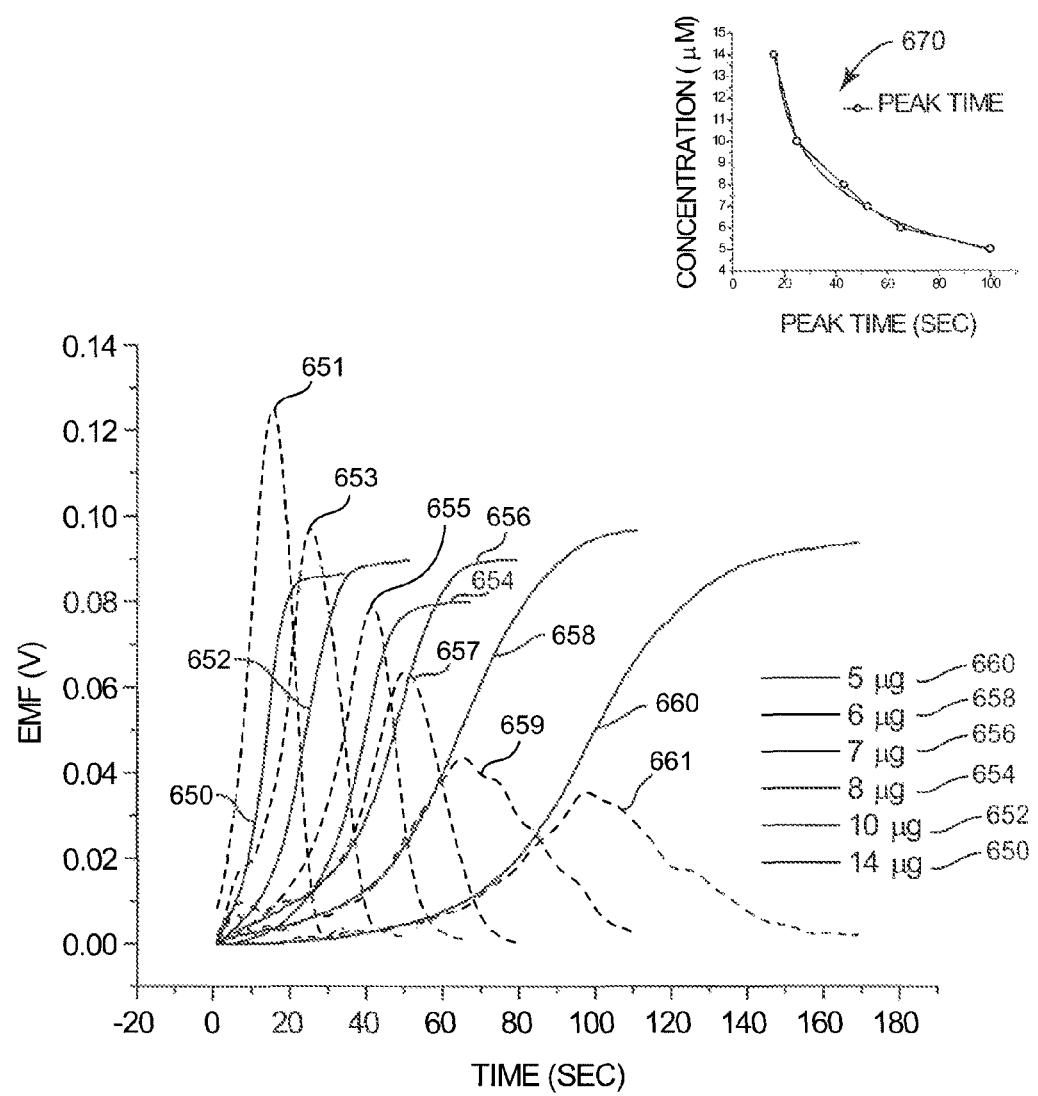
FIG. 26A shows the experimental results of exposing a protamine ion sensitive electrode to varying concentrations of protamine, to determine the time of peak rate of change of potential versus time, which can be used to calibrate protamine ion selective electrodes for the so-called "bolus" method.

FIG. 26A illustrates the results of varying protamine concentrations of a test system. The results of FIG. 26A can be used in interpreting the output of the bolus method electrodes. The results obtained for FIG. 26A are only the results of varying concentrations of protamine being exposed to the protamine sensitive electrodes, with the change in potential measured over time. The X-axis of FIG. 26A is thus purely time, and includes no infusion amount of anything or cumulative infusion of any other substance. FIG. 26A may be viewed as simultaneously inserting similar protamine ion sensitive electrodes into different protamine standards and the results noted.

The highest concentration protamine, 14 micrograms in 1 milliliter of phosphate buffer, is seen at 650. This achieves the most rapid rise in electrical potential. The slowest rise in electrical potential is seen with the protamine ion sensitive electrode inserted into the most dilute protamine sample of 5 micrograms per 1 mil. of phosphate buffer, seen at 660. The 14 microgram, concentrated protamine sample may be seen to achieve a maximum rate of change at about 15 seconds, with the most dilute, 5 microgram protamine sample achieving the maximum rate of change at about 100 seconds.

The peak rate of change is also shown on FIG. 26A, with 651 representing the rate of change or first derivative of plot 650, for 14 micrograms of protamine per milliliter of phosphate buffer. The potential rate of change plots for 10 micrograms may be seen at 653, for 8 micrograms at 654, for 7 micrograms at 656, for 6 micrograms at 658, and for 5 micrograms at 661.

An inset plot 670 may be seen in FIG. 26A, showing a plot of protamine concentration versus peak time in seconds. Thus, the protamine concentration of a sample may be derived from the time required to achieve the peak rate of change of electrical potential versus time. In another method, the protamine concentration of a sample may be derived from the maximum slope of the curve, i.e. the slope at the inflection point. For example, inspect the "first derivative" plots, the odd numbered plots from 651 through 661, taking note of the peak height variation with protamine concentration.

This method, for determining protamine concentration, can be used to determine heparin concentration. This can be done using the "bolus" method of the present invention. A known bolus of protamine can be added, sufficient to completely bind the heparin expected in a sample, sufficient to leave excess protamine in solution.

The protamine ion selective electrode can be exposed to the excess protamine and the time to peak potential rate of change noted. This time can be used in conjunction with a calibration curve such as 670 to obtain the remaining protamine in the sample. Using the initial, known protamine, and the stoichiometric binding of the known protamine to the heparin, the heparin concentration in the sample can be calculated. This method would require no titration. This method could also be used in conjunction with a sample cartridge having a known protamine amount preloaded into a cartridge, ready to receive a heparin sample injected into the cartridge.

Log (dEMF/dt) Bolus Method

Figure 26B:
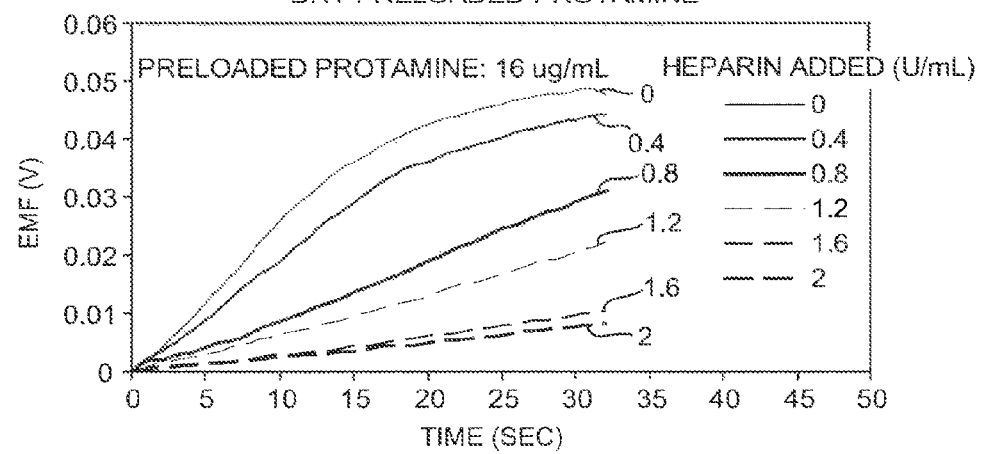
FIG. 26B shows the experimental results of exposing a protamine ion sensitive electrode to varying amounts of heparin added to an excess protamine bolus, to determine the initial rate of change of differential electrical potential for various heparin sample concentrations, which can be used to calibrate protamine ion selective electrodes for the "bolus" method.
Figure 26C:
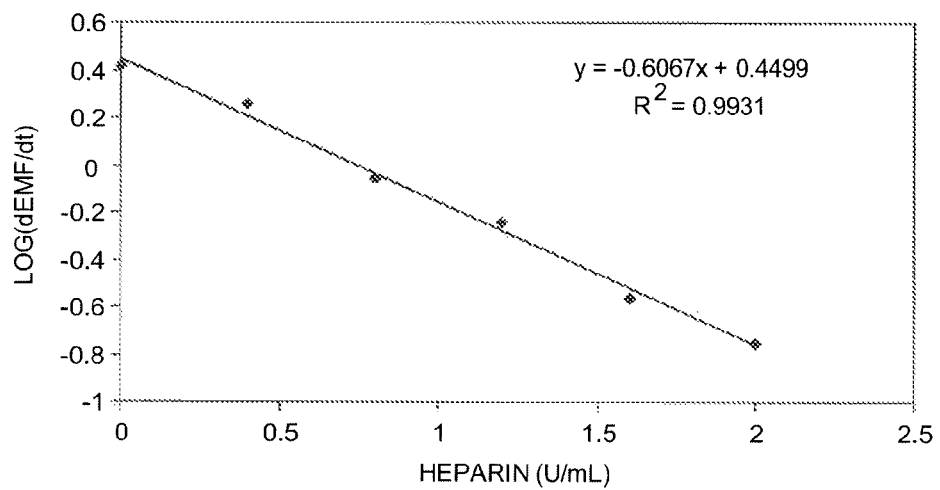
FIG. 26C shows the log of the dEMF/dt versus heparin concentration results from FIG. 26B, illustrating a linear relationship that can be used in some embodiments to determine heparin concentration in a sample, for the "bolus" method.

FIGS. 26B and 26C illustrate experimental results and a method that can be used with the bolus method to determine the heparin concentration in a sample.

By way of introduction, detection of heparin can be accomplished with automated potentiometric titrations of heparin, using continuous addition of a standard protamine solution into a sample solution using a dispensing system, for example having a pressure pump and a micro-valve. However, the instrumentation is complex and may not easily be miniaturized.

To eliminate the dispensing system, applicants developed a method including pre-loading a fixed amount of dry protamine in the cartridge to neutralize heparin in the sample, and measuring the electrode potential response of the extra free protamine. In this method, the response process is recorded and the time required to achieve the maximum response rate is used for heparin quantization. However, this quantitative method may be time consuming, in order to get enough of the response curve, especially for samples containing high concentrations of heparin. In addition, there is no linear relationship between the endpoint time measured and the heparin concentration in the sample (see FIG. 26A).

Here we describe a new quantitative method for the dry protamine bolus concept. In this method, the initial potential response rate (dEMF/dt) is measured (see FIG. 26B) and a good linear relationship between heparin concentration and the logarithm of dEMF/dt is used for heparin calibration (see FIG. 26C).

With this method, there is no need to wait for the whole response process; but only the initial response may need to be recorded, so the whole analysis can be rapidly completed. In addition, applicants believe that the optimum linear range for heparin measurement can be readily adjusted by changing the sample stir rate. Higher stir rates show a narrow linear range, but with a high resolution, for low concentrations of heparin, which is suitable for use in a Catheter Lab; while low stir rates show a wide linear range with a relative low resolution and can be used in CVOR.

Example Heparin Assay Cartridge System Using Bolus Method

Figure 29A:
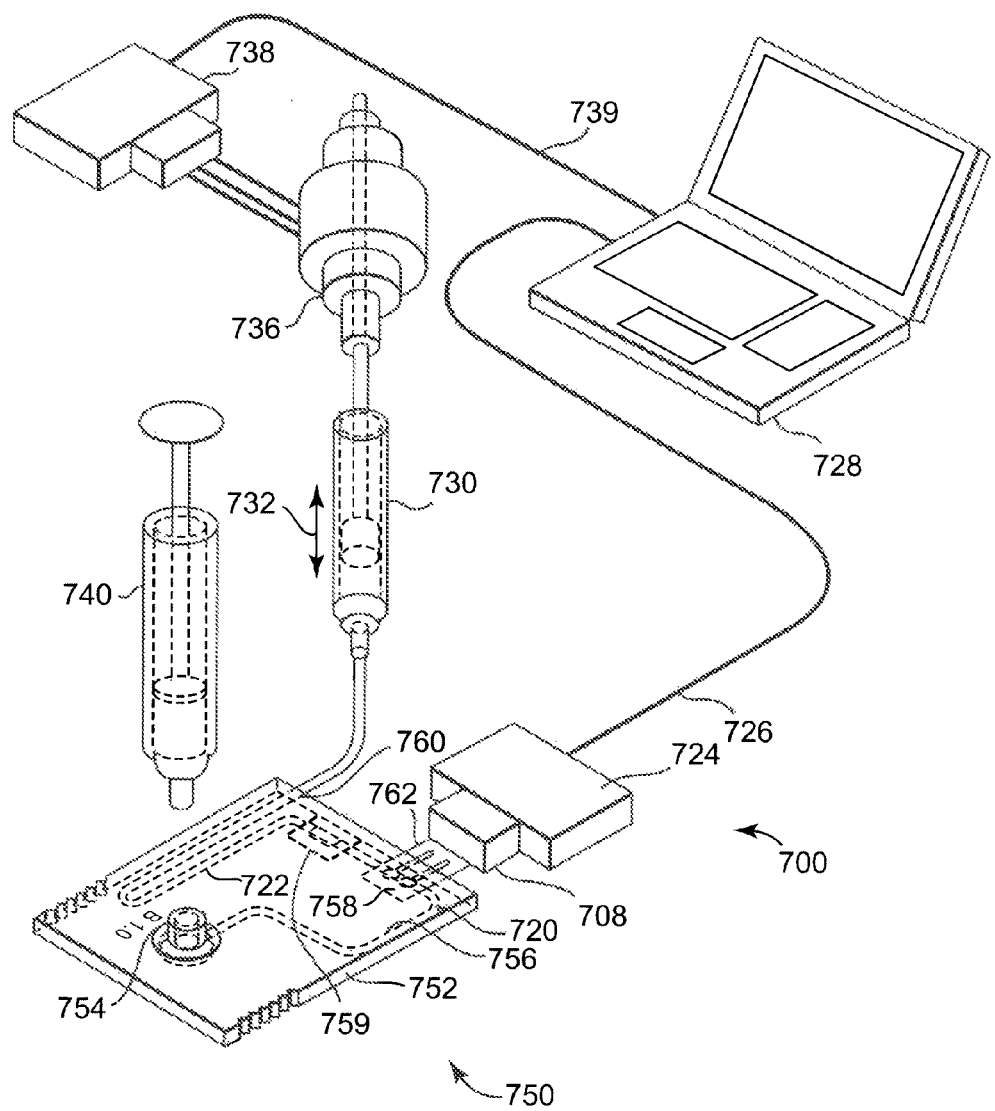
FIG. 29A is a pictorial diagram of a cartridge-based system using a positive-displacement reversible fluid pump with a two sensor cartridge having a simple fluid path.

FIG. 29A shows a diagram of the primary elements of a cartridge-based system 700 using a positive-displacement bi-directional fluid pump 730 for fluid transport and stirring. System 700 includes a cartridge 750, a sample applicator 740, and a controller/analyzer represented by a computer 728.

Cartridge 750 includes a cartridge body 752 containing a fluid path 756. Fluid path 756 extends from a sample chamber or sample port 754, past a first sensor chamber 758, past an optional second sample chamber 759, to a pressure port 760. Fluid path 756 includes a first portion 720 disposed between sample port 754 and sensor chambers 758 and 759, and a second portion 722 disposed between the sensor chambers and pressure port 760. A first sensor 762 is shown inserted into sensor chamber 758 to bring the ISE or ISEs into contact with fluid path 756. In some systems, the ISE is screen printed on a polyester substrate, and the sensor chamber is initially open to the bottom. The ISE can be adhesively applied to the sensor chamber bottom, sealing the sensor chamber. The ISE may include a protamine ISE and a reference ISE, and may includes a second ISE and corresponding reference ISE, where the second ISE may be used to measure a different analyte. Sample chamber 758 may contain an amount of dried protamine sufficient to neutralize the largest amount of heparin anticipated to be in the sample.

Bi-directional pump 730 may be attached through a pressure line 734 to pressure port 760 at the most distal point of the fluid path. The bidirectional pump may be controllable in discrete increments of linear travel, indicated at 732, by a pump motor 736. Pump motor 736 can be controlled by a motor controller circuit 738, which is in turn connected by a motor controller cable 739 in some systems, to a lab instrument interface circuit installed in computer 728.

Sensor chamber 758 may be located midway through cartridge fluid path 756, and may contain a protamine-sensitive sensor 762. The sensor may be connected through a sensor connector 708 to a sensor amplifier 724, which can buffer and amplify the signal from the high-impedance sensor. Sensor amplifier 724 may be connected by a sensor amplifier cable 726 to a lab instrument interface circuit installed in computer 728. Computer 728 is used to represent a data acquisition and control device generally. Such a device can be used to drive pump 730 and monitor sensor 762. Any suitable dedicated device, programmable device, or microcontroller may used as this device.

A metered volume of sample containing heparin can be introduced into sample chamber or port 754 using a sample applicator 740. The bidirectional pump 730 may be activated to repeatedly draw the sample from the chamber into fluid path 756, and then push the sample back into the chamber, in order to agitate and dissolve the protamine into the sample. This action could be started either automatically by a sensor, or by a user's key press.

After the protamine is dissolved into the sample, bidirectional pump 730 may draw the sample into sensor chamber 754. The sample may be stationary in the sensor chamber for approximately 30 seconds to "wet" the sensor membrane in sensor 762, with the computer monitoring the sensor signal. Bidirectional pump 730 may then move the sample in a back-and-forth oscillation across the sample chamber 758 while the computer continues to monitor the sensor signal. The oscillation facilitates the diffusion of ions into the sensor membrane while the computer measures the sensor response, and the heparin concentration may be determined from the slope of the response curve to free protamine within the first minute or two after oscillation begins.

One Example of Bolus Method

One procedure for heparin measurement using a cartridge system with preloaded dry protamine and citrate bolus is given below. This example utilized a Labview program running in a computer program interfaced to a bread boarded, prototype embodiment according to the present invention. A system similar to that of FIG. 29A was utilized.

1. When the blood sample (0.15 mL) is added to the sample reservoir, the operator can click "Start Measurement" on the keyboard to start the program. The piston of the syringe pump can draw the sample into the cartridge channel and move the sample back and forth for about 1 min to mix with dry protamine and citrate preloaded in the channel.

2. Then the resulting sample solution can be drawn into the sensor chamber and the Labview program will be activated to record the potentials of sensor membrane (measuring every second). The sample solution will be held on the sensor surface for a wetting period of 30 sec.

3. After wetting, the pump starts oscillation, and the membrane potentials increase dramatically due to the rapid protamine diffusion into membrane phase.

4. The oscillation takes 30 sec, and then the measurement is finished.

5. The pump piston will be reversed to its original position for the next measurement.

6. The initial response rate (dEMF/dt, the slope of the linear curve) can be calculated by using 5 potentials measured at 33, 34, 35, 36, and 37 sec. In some methods, the initial response slope is measured in the portion defined by three points in which the line segments on either side of the middle point are closest to the line between the two outer points, or the minimum distance between the middle point and a line drawn through the two points on either side of the middle point. In other methods, the average of the slope of the line segments between the measured points is used as the initial slope.

Figure 30A:
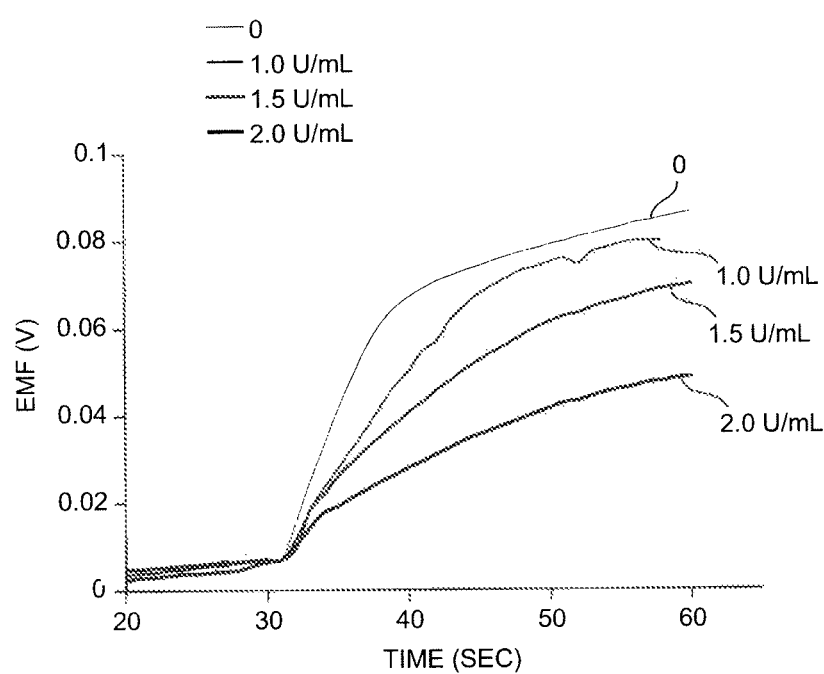
FIG. 30A illustrates the experimental results of EMF vs. time using a system similar to that of FIG. 29A with various heparin concentrations in a bolus method.
Figure 30B:
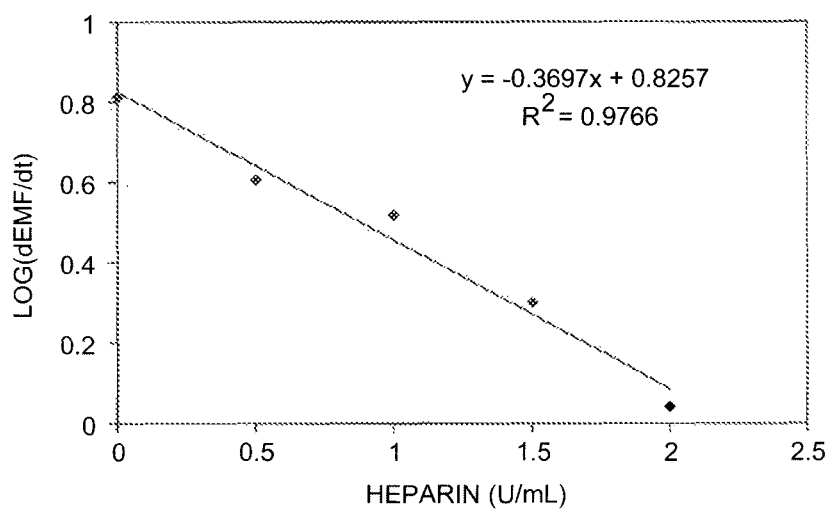
FIG. 30B illustrates a log plot of the initial slope vs. sample heparin concentration from the experimental results of FIG. 30A.

7. Higher concentrations of heparin in blood neutralize more protamine in the cartridge, and therefore show less response. See FIG. 30A. After logarithm conversion of dEMF/dt for each concentration, a linear calibration curve can be obtained (See FIG. 30B).

Two Sensor Cartridge

FIGS. 29B-29D further illustrate cartridge 750 having two ISE sensor chambers. FIG. 29B is a top view, 29C a bottom perspective view, and 29D a top perspective view of the cartridge. Cartridge 750 includes body 752 having first sample chamber or sample port 754 coupled to fluid path 756 which includes first sensor chamber 758, second sensor chamber 759, and can terminate in either a blind cavity or a pressure port 760. First sensor 762 may be seen inserted into first sensor chamber 758, which, in this embodiment, is open at the bottom.

Viscosity Compensation Method

An advantage to the bidirectional pump system over a rotationally-stirred sample chamber is that the pump system is positive-displacement, and should be relatively insensitive to changes in viscosity of whole blood due to varying hematocrit and hemodilution. If viscosity must be taken into account for greatest precision, this could be done by using an additional separate sensor and fluid path, where the fluid path dimensions cause capillary flow of the sample, and the time for the sample to travel a known fluid path length to reach the sensor is measured and used to calculate the relative viscosity of the sample.

Alternate Embodiments for the Heparin Assays Cartridge System

Several methods can be used to enhance the performance of the Heparin Assay Cartridge System.

A method could be incorporated into the cartridge to automatically meter the sample volume. This could be implemented by using a gas-permeable vent in combination with the bidirectional pump. Alternatively, an arrangement using valves or two pumps could be used to isolate and transport a metered volume.

An anticoagulant such as sodium citrate or disodium EDTA can be combined into the sample to increase the sensitivity of the system when used with whole blood. This can be done either prior to introduction of the sample into the sample chamber, or as an initial step within the sample chamber.

Two separate settings for bidirectional pump speed could be used for optimizing sensitivity vs. range for the differing requirements of the Cardiovascular Operating Room (CVOR) and the Cardiac Catheterization Laboratory. These could be used in combination with cartridges containing two different amounts of protamine, and could be selected either automatically by a code on the cartridge, or manually by the user. Alternatively, an adaptive algorithm could be used to monitor the initial slope, and then automatically change the pump speed setting for best combination of sensitivity and range.

Separate settings could be selected by the user to apply different slope-to-concentration algorithms for different types of low-molecular-weight heparin as well as unfractionated heparin. For low-molecular-weight heparin, the results could be displayed in various units including anti-Xa correlation. Alternatively, an algorithm could be selected to measure the combined effect of multiple heparin types contained within the sample.

The sample chamber could contain liquid protamine instead of dried protamine. The protamine could be held within the chamber by a thin-stretched film over the chamber top, and the sample applicator could be used to simultaneously penetrate the film and introduce the sample into the chamber.

Direct Heparin Sensor

The above embodiments make use of a protamine sensor to measure the amount of heparin through stoichiometry. A heparin sensor has also been developed that responds directly to the heparin in the sample. When a heparin sensitive electrode is used in the heparin assay cartridge system, there is no need to place protamine in the cartridge, and accurate sample volume may not be required. The heparin is directly measured and the response slope can be directly converted into the heparin concentration. The use of a sample blank, having the heparin inactivated, may be useful in this method.

Test Strip with Current-Driven Ion Exchange

Another embodiment of the heparin assay disposable and its instrument interface would produce a low-cost laminated test strip with no moving part required in the instrument. This embodiment uses a direct heparin sensor in combination with disposable designed to produce capillary flow of the sample to the sample chamber after the user deposits the sample on the disposable. Additionally, this embodiment does not require a bidirectional pump to stir the sample across the sensor. Instead, a voltage is applied to the sensor to facilitate ion exchange across the sensor membrane. This method might use alternating time periods of current drive and sensor monitoring, or a compensated sensor circuit might be devised to provide simultaneous current drive and sensor monitoring.

Enhanced Sensitivity

Unlike many other electrochemical potentiometric sensors, protamine ion selective electrode sensors have a unique response that is not a typical Nernst response. Instead, it relies on the non-equilibrium steady state ion exchange process occurring at the interface between the sensor's polymer membrane and the sample solution. The protamine sensitive sensor response is determined by both the protamine diffusion in the sample phase and the diffusion of the protamine-ion exchange complex inside the polymer membrane phase. The sensor's low detection limit can be significantly improved by rotating the sensor at a high speed, for example, 3,000 RPM, which may or may not be practicable when used in conjunction with various embodiments of the present invention.

In one method according to the present invention, diffusion is enhanced inside the polymer membrane by changing the boundary condition from constant concentration change/flux (as in a previous method) to a constant concentration. Diffusion enhancement inside the membrane phase is confirmed by theoretical simulation. Specifically, a theoretical simulation shows that in a constant boundary concentration case, there is a higher analyte concentration inside of the membrane phase than that in the constant flux case. This means a higher potential change of the sensor, which means improved sensitivity.

Figure 27:
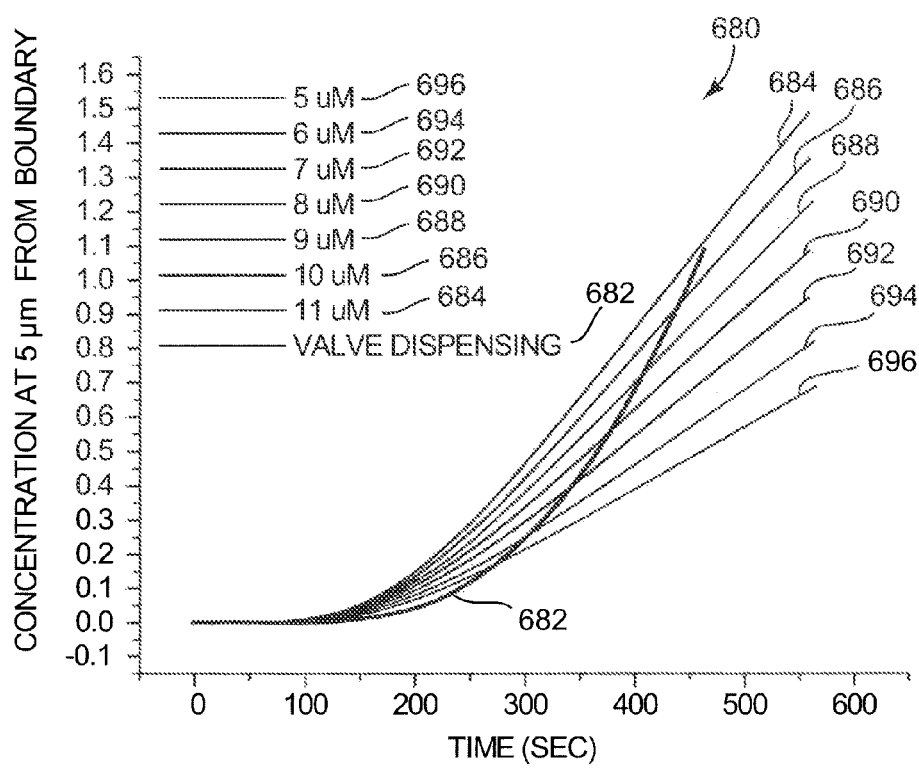
FIG. 27 shows a theoretical simulation plotting concentration immediately inside the ion selective electrode membrane versus time for both the conventional protamine valve dispensing in titration of heparin, and for the immediate exposure of the membrane to varying concentrations of protamine.

FIG. 27 shows a theoretical plot indicating a concentration at 5 micrometers from the boundary, inside the membrane. Plots 684-696 indicate the concentration at 5 micrometers inside of sensor membrane boundary. Various amount of protamine are presented in the aqueous sample phase as constant concentration (684-696) versus continuous dispensing of protamine in the aqueous phase (682). In this theoretical plot, within the time frame of 250 seconds, when the ion exchange membrane is exposed to a high concentration of protamine, the concentration within the membrane rises the most rapidly, as seen at 684. Conversely, the concentration of protamine within the membrane rises the most slowly when exposed to a lower concentration of protamine, seen at 696. The results for varying concentrations of protamine, specifically, 5, 6, 7, 8, 9, 10, and 11 micromolar concentrations of protamine seen respectively at 696, 694, 692, 690, 688, 686, and 684. The theoretical concentration of protamine 5 micrometers within the membrane using the previous valve-dispensing method is shown at 682. Thus, at 300 seconds, the old method would show about 0.2 concentration (arbitrary units) of protamine while the 10 micromolar concentration of protamine in the constant concentration case would show almost double that concentration (arbitrary units) within the membrane.

Thus, compared with the previous titration method, the new bolus method is more sensitive and doesn't need protamine to be dispensed during the test. Hence, instrumentation can be simplified. Also, simultaneous calibration can be possible after filtering or otherwise removing heparin from the sample separately, since multiple tests can be done on the same disposable cartridge without using multiple dispensing units. Lower detection limits and improved resolution can enable this sensor to monitor therapeutic level heparin (both high and low molecular weight heparins).

Ion Selective Electrode Polymer

The present invention can utilize generally a polymeric membrane forming an ion selective electrode that is selective for protamine. Generally, this ion selective electrode may include a polymer, an ionophore or ion exchanger that preferentially binds protamine, and zero, one or more plasticizers that facilitate or enhance diffusion of protamine into the membrane. Various polymers, ionophores, and plasticizers and/or additives, if so desired or necessary, can be used, with varying degrees of success, in the present invention. In one embodiment of the invention, a specialized polyurethane is used as at least one polymer in the polymeric matrix. This specialized polymer includes alternating blocks of so-called "soft" or rubbery segments (having easy segmental rotations at ambient temperature) and "hard" (crystalline, semi-crystalline or glassy) segments. The hard and soft segments may separate from each other, thereby forming hard and soft segment micro-domains. The first step of synthesis of this specialized polymer, which is a thermoplastic elastomer, is the production of a pre-polymer in which the ends of the polymer chain is terminated by isocyanate groups (—N=C=O) or hydroxyl groups (—OH). The production of the prepolymer may involve the use of a preformed chain terminated by hydroxyl groups, for example a polyester glycol, polyether glycol, hydrocarbon glycol, polydimethylsiloxane glycol, or a polycarbonate glycol. The glycol chain is then reacted with one or more diisocyanates, for example methylene-4,4'-diphenyl isocyanate (MDI), dimer isocyanate, methylene-4, 4'-dicycloxyl isocyanate (H12-MDI), hexylmethylene diisocyanate, or any other suitable diisocyanate. The resulting pre-polymer is then reacted with one or more diols and/or diamines, for example ethylene diamine and/or butane diol, to link the ends of the prepolymer chains together and thus generate the polymer chains of the thermoplastic elastomer.

Figure 28:
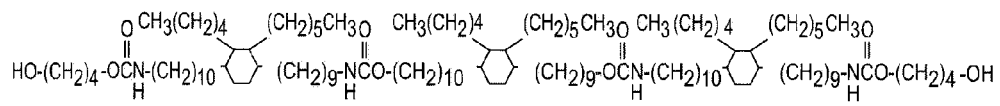
FIG. 28 is a chemical structure of one polyurethane that can be used in the protamine ion selective electrode, including linear aliphatic and cyclic aliphatic regions between the urethane groups.
Figure 28:
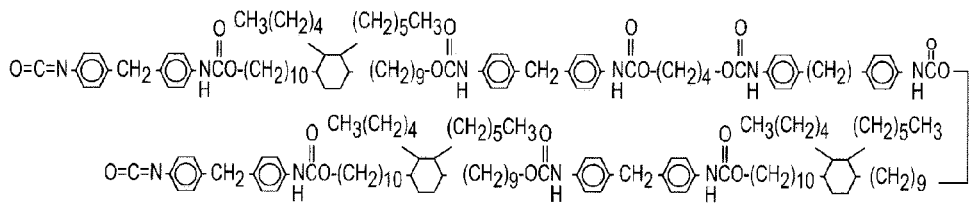

One polyurethane used according to one embodiment of this invention is illustrated in FIG. 28 as having a combination of soft segments and hard segments. The soft segments are generally formed by the reaction of dimer isocyanate, for example 1-decyl-4-nonyl cyclohexyl diisocyanate (having a pentyl group at ring position 2 and a hexyl group at position 3), with either butane diol and/or dimer diol, for example 1-decyl-4-nonyl cyclohexyl diol (having a pentyl group at ring position 2 and a hexyl group at position 3).

FIG. 28 shows one example of the soft segment that may be formed in the reaction product of dimer diisocyanate, dimer diol and butane diol when reacted in a molar ratio of 2:1:2, respectively. In general, the soft segments contain both straight chain aliphatic and cyclic aliphatic regions between the urethane groups. The cyclic aliphatic regions may have straight chain aliphatic groups pendent therefrom. In the example shown in FIG. 28, the cyclic aliphatic groups are shown to have pentyl and hexyl aliphatic linear groups at the 2 and 3 positions of the ring, respectively, however many other isomers for dimer isocyanate and dimer diol are possible. Applicants do not believe that the length of the straight chain aliphatic regions, such as the butane diol, is critical. Applicants believe that either straight chain aliphatic or cyclic aliphatic groups may be used to form the ion selective electrode soft segment region however other hydrophobic moieties may also provide acceptable polyurethanes.

FIG. 28 also shows one example of a polyurethane hard segment that may be formed as the reaction product of methylene diphenylisocyanate, dimer diol (for example 1-decyl-4-nonyl cyclohexyl diol), and butane diol when reacted in a molar ratio of 5:3:1, respectively. The hard segments thus contain alternating regions of methylene diphenylisocyanate with either cyclic aliphatic regions or straight chain aliphatic regions, as described above with respect to the soft segment.

Polyurethanes that can be used in the present invention are described in U.S. Pat. No. 4,873,308, herein incorporated by reference in its entirety.

Example of Protamine Sensor Preparation

One example of how to prepare an ion selective electrode polymer solution to be used in the production of a protamine sensor follows:

Combine 21.0 mg of dinonylnaphthalene sulfonate (DNNS) from King Industries, Norwalk, Conn. with 300 mg of 2-nitrophenyloctyl ether (NPOE) from Fluka Chemika Biochemika, Ronkonkoma, N.Y. in a glass container. Then add 3.0 mg of tetradodecylammonium tetrakis (4-chlorophenyl) borate (ETH500) from Fluka Chemika Biochemika, Ronkonkoma, N.Y. and 80 mg of Terpolymer (PVC/PVA/polyhydroxypropyl acrylate) from Scientific Polymer Products, Ontario, New York into the same glass container. Next add 197 mg of the polyurethane described elsewhere in the present application and 395 mg of Pellethane 2363-AE from Dow Chemical, Midland, Mich. into the same glass container. Then add 5.68 ml cyclohexanone solvent and stir using a stirrer bar and a magnetic stirrer. Allow components to dissolve completely. Preferably, the resultant polymer solution will have no solids present and will have a viscosity of about 450 cp. If the viscosity of the polymer solution is too low, the polymer solution can be concentrated to raise the viscosity. If the viscosity of the polymer solution is too high, solvent can be added to the polymer solution to lower the viscosity.

The silver leads of a sensor are treated with 0.1 M 0.1 M $FeCl_3$ solution containing 0.5 M HCl for 5 min to form Ag/AgCl electrodes. The electrodes are then washed with de-ionized water and dried overnight in a fume hood at room temperature. One drop (3 μL) of the polymer solution is then applied on one electrode, for example the right hand side electrode. The other electrode or left hand side electrode is not coated and serves as a reference electrode. The polymer-covered sensors are placed in the fume hood and dried for 3 hours at room temperature. Additional applications of the polymer solution to the electrode followed by drying may be repeated as desired to achieve a desired membrane thickness. Following application of the last polymer coating step the electrodes are thoroughly dried, for example by placing the electrodes in fume hood at room temperature for 24 hours.

Preferably, the tip of the silver is completely covered by the membrane. The performance of the sensors is not affected if the side of the membrane coating (not the silver) is cut or has small bubbles. If the viscosity of the polymer solution is too low, the polymer may spread into a larger area and cover the reference electrode so that the sensor may be scrapped. On the other hand, if the viscosity of the polymer solution is too high, it will be difficult to get an optimum sized droplet. The sensors are generally acceptable if the tip of the silver is completely covered by the polymer membrane and the polymer does not cover the reference electrode.

Concentration ranges (in terms of weight percent) of membrane components for various embodiments of the protamine sensor are given below. The "specialized polyurethane" is the polyurethane illustrated in FIG. 28 and discussed in the associated text. ETH 500 is a lipophilic salt commonly used as an additive in polymeric sensor membrane to reduce the membrane impedance. The chemical name is tetradodecylammonium tetrakis (4-chlorophenyl)borate, purchased from Fluka Chemika Biochemika, Ronkonkoma, N.Y. Pellethane is a trademark of The Dow Chemical Company, it includes a group of polyurethanes. The pellethane used in the sensor membranes below is Pellethane 2363-80AE from Dow Chemical, Midland, Mich. More information may be currently found at the Dow website at http://www.dow.com/engineeringplastics/prod/na/pel.htm.

Terpolymer (PVC/PVA/polyhydroxypropyl acrylate) is available from Scientific Polymer Products, Ontario, New York. The composition is vinyl chloride 80%, vinyl acetate 5%, and hydroxylpropyl 15%.

First Composition:
DNNS (0.5-8%)
NPOE (15-60%)
ETH 500 (0.1-1%)
Terpolymer (2-15%)
Specialized Polyurethane (10-50%)
Pellethane (10-60%)
Second Composition:
DNNS (1-5%)
NPOE (20-40%)
ETH 500 (0.2-0.5%)
Terpolymer (5-12%)
Specialized Polyurethane (15-30%)
Pellethane (30-50%)
Third Composition:
DNNS (2%)
NPOE (30%)
ETH 500 (0.3%)
Terpolymer (8%)
Specialized Polyurethane (20%)
Pellethane (40%)

Self-Plasticizing Membranes

In one aspect of the invention, in an alternative embodiment, the ISE membrane/polymer is self-plasticizing. Plasticizers are typically used in ISE membranes and may form a considerable portion of (e.g. even half) of the membrane weight. The plasticizer allows the analyte to migrate through the ISE membrane. In some ISE membranes according to the present invention, there is no, or essential no unbound plasticizers in the ISE membranes. The membrane may be formulated from a polymer with a backbone, which may be an acrylate backbone and have a plurality of pendant lipophilic plasticizing groups.

The membrane can be formulated from a polymer having an acrylate backbone and a plurality of pendant lipophilic plasticizing groups to provide the polymer with a Tg of −10° C. or less. The Tg of the polymer can be measured directly using any suitable apparatus. The polymer Tg lies in the range from −10° C. to −70° C., or from −30° C. to −60° C., in some embodiments. The lipophilic plasticizing groups are C3-7 alkyl groups in some polymers used in the present invention. Use of C3-7 alkyl acrylates in the polymer can provide a polymer that is inherently soft and does not require added plasticizer, i.e. the polymer is in effect self-plasticizing.

Other Membrane Materials

Materials such as ceramics, metal-oxides, glass, and polymers could be used as part of the membrane carrying the ionophore in some alternate embodiments. In a less preferred embodiment, if porous glass or ceramic were used, the pores may be loaded with ion-selective cocktail or polymer solution. Some polymers can include polyurethane, PVC, and silicone rubber. Some polymers may not require a separate, added plasticizer. The polymer used according to the invention may have an acrylate backbone and may be a polymer or copolymer of one or more of the following monomers: propyl acrylate, butyl acrylate, pentyl acrylate, hexyl acrylate, heptyl acrylate. The polymer may be a homopolymer or may be a co-polymer including two or more different monomer units. The different monomer units may be derived from C3-7 alkyl acrylates as described above.

Example Titration Procedure Using Protamine Sensor

Heparin solutions containing 1,000 U/mL and 100 U/mL of heparin are prepared by serial dilution with phosphate buffered saline (PBS) (pH=7.4) of a heparin USP stock solution containing 10,000 U/mL. The 100 U/mL heparin stock solution is used to prepare the heparin samples required for titration in buffer, whole blood or pooled plasma (2, 4, 6 U/mL, etc.). A protamine solution is then prepared in saline (0.9%) from a stock solution of Protamine Sulfate USP Injectable, which contains 250 mg activity per 25 ml of solution. The final concentration of the protamine solution is 10 mg/ml. The stock solution is refrigerated. The protamine test solution is usually stable at room temperature for one week. PBS buffer solution is prepared by dissolving 1 foil pouch of dry PBS powder (Sigma-Aldrich) into 1 liter of de-ionized water. Citrated whole blood is prepared by mixing 5 ml of 3.4% sodium citrate per 50 ml of whole blood. Plasma is prepared by centrifuging citrated whole blood. Plasma (about 150 ml) may be stored at 20° C. in 10 mL centrifuge test tubes. The frozen plasma is generally stable for 24 weeks.

The sensor is connected to the appropriate hardware, e.g., an electric circuit board from Alberta Printed Circuits and an electronic control circuit from National Instruments. Make sure the electrode is placed in the correct position. Following connection of the sensor to the appropriate hardware and software, the sensor may be calibrated. When ready to calibrate the sensor, start running the data acquisition or control software (e.g., Labview Software) on an appropriate computer, e.g., a Toshiba satellite 2065 CDS laptop computer, connected to the appropriate hardware. The control software implements algorithms described in the present application. Alternatively, the titration could be performed manually. While running Labview, click on "STARTDAQ". The potential (EMF) response of the sensor will be shown in the window. The green line indicates the EMF change with time, while the red line shows the first differential of the EMF response (dEMF) change with time. When the baseline is stable, click "Start LEE-VALVE". The protamine will be dispensed into the sample as a titrant at 1 drop per second from a microdispensing valve with an integral nozzle (part number: INKA2437210H, VHS-LT valve, Lee Co., Essex, Conn.). The dispensing rate can be multiplied by 2, 5- or 10 times if clicking "S0", "S1" or both of them. Click "STOP DISPENSE", when the response curve reaches a stable maximum potential. Click "SAVE DATA" and give an appropriate file name. Repeat the steps for another titration. Exit LABVIEW when all the measurements are completed. The concentration of the heparin present in the solution and the amount of protamine needed to neutralize the heparin can be calculated by the calibration time and the response time from the heparin unknowns using the same Excel work sheet.

A calibration curve is made for each of the samples used, such as buffer, plasma or whole blood. The calibration time for plasma and whole blood is greater than that of the buffer solution. A minimum of 2 calibration curves/titration curves can be taken for each of the samples tested. The samples used for the calibration do not have any heparin in it. The time in seconds to reach the end point is used to calculate the heparin concentration of the unknown samples. One (1) minute incubation time is given for each of the sensors tested before running the experiment in whole blood or pooled plasma (no incubation time for buffer solution).

For a titration experiment, pipette one (1) ml of the fresh sample solution into a sample cup. Add a magnetic stirrer bar into the sample solution. The sample solution is then stirred at a constant speed (e.g. 600 rpm) using a magnetic stirrer (American Scientific Products) in order to achieve a rapid mixing of the solution. It is preferable to maintain a constant speed of mixing to get reliable data. Make sure the sensor is connected to the electric circuit board. Double check to confirm the electrode is placed in the correct position. Place the membrane end of the sensor in the sample solution. It should be placed in such a way that the sensor does not touch the magnetic stirrer and the polymer membrane is in the sample solution. Start an air pump (DP0105, Nitto Kohki, Co. Ltd.) and apply an air pressure of 300 mmHg (~5.9 psi) using a pressure regulator (Type 100, Controlair Inc.) around the liquid protamine pouch. In this case, the volume of one drop of protamine solution dispensed through Lee valve is 25 mL. Follow the procedures described above.

Each unit of heparin present in the sample solution prolongs the response time. (e.g.: Beef lung heparin I U/ml Heparin ~30 seconds, Porcine Mucosa Heparin ~25 seconds, LMWH Fragmin ~22.5 seconds, LMWH Normiflow ~35 seconds, LMWH Lovenox ~40 seconds The concentration of heparin present is calculated using the calibration time, titration end point for the unknown samples and the type of heparin. The amount of protamine required to neutralize the heparin can be calculated using the heparin protamine binding stoichiometry (1 mg of protamine reacts with 100 U of heparin).

All publications, patents and patent documents are incorporated by reference herein, as though individually incorporated by reference. The invention has been described with reference to various specific and preferred embodiments and techniques. However, it should be understood that many various modifications may be made while remaining within the spirit and scope of the invention.

What is claimed is:

1. A method for measuring heparin in a first blood sample, the method comprising:
    inactivating essentially ell the heparin in the first blood sample to create a reference sample;
    measuring the output of a first ion selective electrode pair exposed to the reference sample, the first electrode pair having a protamine ion selective electrode and a reference electrode;
    measuring the output of a second ion selective electrode pair exposed to a second blood sample, the second electrode pair having a protamine ion selective electrode and a reference electrode; and
    determining the second sample heparin amount including using the second electrode pair output adjusted by the first electrode pair output.

2. The method of claim 1, in which the first and second blood samples derive from a common blood sample.

3. The method of claim 2, in which the first blood sample is taken from a patient at a first point in time and the second blood sample is taken from the same patient at a second point in time subsequent to the first point in time.

4. The method of claim 2, in which the first and second electrode pairs measuring occurs substantially contemporaneously with each other.

5. The method of claim 2, in which the second electrode pair measuring occurs subsequent to the first electrode pair measuring.

6. The method of claim 5, further comprising measuring a third blood sample from the same patient using a third electrode pair.

7. The method of claim 1, in which the inactivating includes degrading the heparin using an enzyme.

8. The method of claim 1, in which the inactivating includes binding the heparin.

9. The method of claim 1, in which the inactivating includes binding the heparin to polycations immobilized on to a solid matrix.

10. The method of claim 1, in which the inactivating includes binding the heparin to polylysine immobilized on a solid matrix.

11. A method for determining a heparin concentration in a sample, the method comprising:
    adding the sample and a protamine amount sufficient to bind all the heparin expected in the sample to a sample chamber to mix the sample and protamine;
    obtaining a differential electrical potential between a reference electrode and a protamine sensitive electrode over time, where the electrodes are in contact with the mixed sample; and determining the heparin concentration at least in part as a function of the slope of the differential electrical potential over time in a substantially linear region of electrical potential versus time, wherein the log of the slopes of various different protamine concentrations versus heparin concentration is substantially linear.

12. A method for determining a heparin concentration in a sample, the method comprising:

adding the sample and a protamine amount sufficient to bind all the heparin expected in the sample to a sample chamber to mix the sample and protamine;

obtaining a differential electrical potential between a reference electrode and a protamine sensitive electrode over time, where the electrodes are in contact with the mixed sample;

obtaining calibration values to use in determining the heparin concentration by exposing a known protamine concentration solution to a similar, second reference and protamine sensitive electrode pair and obtaining the differential electrical potential over time for the second reference and protamine sensitive electrode pair; and determining the heparin concentration at least in part as a function of the slope of the differential electrical potential over time in a substantially linear region of electrical potential versus time.

\* \* \* \* \*

UNITED STATES PATENT AND TRADEMARK OFFICE
CERTIFICATE OF CORRECTION

PATENT NO.         : 8,801,918 B2
APPLICATION NO.    : 12/748918
DATED              : August 12, 2014
INVENTOR(S)        : Qin et al.

It is certified that error appears in the above-identified patent and that said Letters Patent is hereby corrected as shown below:

On the Title Page

In the Abstract
"... concentration slope values In some ..." should read -- "... concentration slope values. In some ..." --

In the Claims

In Claim 1, column 42, line 21
"... essentially ell the heparin in the first ..." should read -- "... essentially all the heparin in the first ..." --

Signed and Sealed this
Fourteenth Day of July, 2015

Michelle K. Lee
*Director of the United States Patent and Trademark Office*